United States Patent
Lyday

(10) Patent No.: US 11,357,795 B2
(45) Date of Patent: Jun. 14, 2022

(54) COMBINATION IMMUNOTHERAPIES FOR TREATMENT OF CANCER

(71) Applicant: PRIMEVAX IMMUNO-ONCOLOGY, INC., Orange, CA (US)

(72) Inventor: Bruce W. Lyday, Orange, CA (US)

(73) Assignee: PRIMEVAX IMMUNO-ONCOLOGY, INC., Orange, CA (US)

( * ) Notice: Subject to any disclaimer, the term of this patent is extended or adjusted under 35 U.S.C. 154(b) by 0 days.

(21) Appl. No.: 15/931,787

(22) Filed: May 14, 2020

(65) Prior Publication Data

US 2020/0276235 A1 Sep. 3, 2020

Related U.S. Application Data

(63) Continuation of application No. 16/413,444, filed on May 15, 2019, now Pat. No. 10,675,304, which is a continuation of application No. PCT/US2017/061810, filed on Nov. 15, 2017.

(60) Provisional application No. 62/423,119, filed on Nov. 16, 2016.

(51) Int. Cl.
| | |
|---|---|
| *A61P 35/00* | (2006.01) |
| *A61K 39/12* | (2006.01) |
| *C12N 7/00* | (2006.01) |
| *A61K 35/15* | (2015.01) |
| *A61K 31/713* | (2006.01) |
| *A61K 35/76* | (2015.01) |
| *C12N 5/0784* | (2010.01) |
| *C12N 15/113* | (2010.01) |
| *A61K 39/00* | (2006.01) |
| *A61P 35/04* | (2006.01) |
| *A61P 35/02* | (2006.01) |

(52) U.S. Cl.
CPC ............ *A61K 35/15* (2013.01); *A61K 31/713* (2013.01); *A61K 35/76* (2013.01); *A61K 39/0011* (2013.01); *A61K 39/12* (2013.01); *A61P 35/00* (2018.01); *A61P 35/02* (2018.01); *A61P 35/04* (2018.01); *C12N 5/0639* (2013.01); *C12N 7/00* (2013.01); *C12N 15/113* (2013.01); *A61K 2039/5154* (2013.01); *A61K 2039/5254* (2013.01); *A61K 2039/55588* (2013.01); *A61K 2039/585* (2013.01); *A61K 2039/70* (2013.01); *A61K 2300/00* (2013.01); *C12N 2310/141* (2013.01); *C12N 2310/531* (2013.01); *C12N 2501/24* (2013.01); *C12N 2770/24133* (2013.01); *Y02A 50/30* (2018.01)

(58) Field of Classification Search
None
See application file for complete search history.

(56) References Cited

U.S. PATENT DOCUMENTS

| | | |
|---|---|---|
| 6,048,686 A | 4/2000 | Lyday |
| 6,511,667 B1 | 1/2003 | Eckels et al. |
| 6,524,587 B1 | 2/2003 | Lyday |
| 7,217,418 B2 | 5/2007 | Eckels et al. |
| 8,415,152 B2 | 4/2013 | Muhlradt et al. |
| 8,889,118 B2 | 11/2014 | Okano et al. |
| 9,730,989 B2 | 8/2017 | Lyday |
| 9,849,167 B2 | 12/2017 | Lyday |
| 10,159,727 B2 | 12/2018 | Lyday |
| 10,357,553 B2 | 7/2019 | Lyday |
| 2002/0146396 A1 | 10/2002 | Albert et al. |
| 2007/0065467 A1 | 3/2007 | Krieg et al. |
| 2007/0082400 A1 | 4/2007 | Healey et al. |
| 2007/0087015 A1 | 4/2007 | Eckels et al. |
| 2013/0089567 A1 | 4/2013 | Whitehead et al. |
| 2015/0166532 A1 | 6/2015 | Gray et al. |
| 2016/0058852 A1 | 3/2016 | Ter et al. |
| 2017/0087233 A1 | 3/2017 | Lyday |
| 2019/0247479 A1 | 8/2019 | Lyday |

FOREIGN PATENT DOCUMENTS

| | | |
|---|---|---|
| WO | WO-0057705 A1 | 10/2000 |
| WO | WO-0156599 A2 | 8/2001 |
| WO | WO-2008022196 A2 | 2/2008 |
| WO | WO-2012160199 A1 | 11/2012 |
| WO | WO-2013188315 A1 | 12/2013 |
| WO | WO-2016179475 A1 | 11/2016 |
| WO | WO-2017004567 A1 | 1/2017 |
| WO | WO-2017053873 A1 | 3/2017 |
| WO | WO-2018093907 A1 | 5/2018 |
| WO | WO-2018129202 A1 | 7/2018 |
| WO | WO-2018232166 A1 | 12/2018 |

OTHER PUBLICATIONS

Andersen et al. Spontaneous immunity against Bcl-xL in cancer patients. J Immunol 175(4):2709-2714 (2005).
Angarone. Epidemiology and Prevention of Viral Infections in Patients with Hematologic Malignancies. Infect Disord Drug Targets 11(1):27-33 (2011).
Angsubhakorn et al. Neurovirulence detection of dengue virus using rhesus and cynomolgus monkeys. J Virol Methods 18(1):13-24 (1987).
Anguille et al. Clinical use of dendritic cells for cancer therapy. Lancet Oncol 15:e257-267 (2014).
Anikeeva et al. Mechanisms Controlling Granule-mediated Cytolytic Activity of Cytotoxic T Lymphocytes. Immunol Res 51(2-3):183-194 (2011).
Armstrong et al. Efficiency of dengue serotype 2 virus strains to infect and disseminate in Aedes aegypti. Am J Trap Med Hyg 68:539-544 (2003).

(Continued)

*Primary Examiner* — Stacy B Chen
(74) *Attorney, Agent, or Firm* — Greenberg Traurig, LLP

(57) ABSTRACT

Described herein are compositions and methods for treating a disease, particularly a cancer, with an immune checkpoint modulatory agent and a strain of an Arbovirus or a strain of an Alphavirus. Also provided herein are also methods for combination therapy comprising administration of an immune checkpoint modulatory agent, tumor antigen primed dendritic cells and an Alphavirus or an Arbovirus.

9 Claims, 10 Drawing Sheets

Specification includes a Sequence Listing.

(56) References Cited

OTHER PUBLICATIONS

Balmaseda et al. Serotype-Specific Differences in Clinical Manifestations of Dengue. Am J Trap Med Hyg 74(3):489-456 (2006).
Bente et al. Dengue Fever in Humanized NOD/SCID Mice. J Virol 79(21):13797-13799 (2005).
Bozza et al. Multiplex cytokine profile from dengue patients: MIP-1b and IFN-gamma as predictive factors for severity. BMC Infect Dis 8:86-93 (2008).
Cabrera et al. Analysis of HLA expression in human tumor tissues. Cancer Immunol Immunother 52:1-9 (2003).
Carreno et al. IL-12p70-producing patient DC vaccine elicits Tc1-polarized immunity. J Clin Invest 123(8):3383-3394 (2013).
Chakraborty et al. Emergence of regulatory CD4+ T cell responses to repetitive stimulation with antigen-presenting cells in vitro: implications in designing APC-based tumor vaccines. J Immunol 162:5576-5583 (1999).
Chalaem et al. Characterization of a Chikungunya virus strain isolated from banked patients' sera. Virol J 13(1):150 (2016).
Chang et al. Production of IL-1 by human monocytes exposed to dengue virus. J Infect Dis 170:811-817 (1994).
Chen et al. Activation of terminally differentiated human monocytes/macrophages by dengue virus: productive infection, hierarchical production of innate cytokines and chemokines, and the synergistic effect of lipopolysaccharide. J Virology 76:9877-9887 (2002).
Chiang et al. A dendritic cell vaccine pulsed with autologous hypochlorous acid-oxidized ovarian cancer lysate primes effective broad antitumor immunity: from bench to bedside. Clin Cancer Res 19(17):4801-4815 (2013).
Chiang et al. Optimizing parameters for clinical-scale production of high IL-12 secreting dendritic cells pulsed with oxidized whole tumor cell lysate. J Transl Med 14;9:198 (2011).
Crooks et al. The use of the Karnofsky Performance Scale in determining outcomes and risk in geriatric outpatients. J Gerontol 46:M139-M144 (1991).
De Haan et al. Measuring quality of life in stroke. Stroke 24:320-327 (1993).
Den Boer et al. Longevity of antigen presentation and activation status of APC are decisive factors in the balance between CTL Immunity Vs. Tolerance. J Immunol 167:2252-2258 (2001).
Dengue: Guidelines for Diagnosis, Treatment, Prevention and Control. World Health Organization (160 pgs) (2009).
Dequen et al. Systematic review and network meta-analysis of overall survival comparing 3 mg/kg Ipilimumab with alternative therapies in the management of pre-treated patients with unresectable Stage III or IV melanoma. Oncologist 17(11):1376-1385 (2012).
Diamond et al. Infection of human cells by dengue virus is modulated by different cell types and viral strains. J Virology 74(17):7814-7823 (2000).
Dillman et al. High-dose IL2 in metastatic melanoma: better survival in patients immunized with antigens from autologous tumor cell lines. Cancer Biother Radiopharm 29(2):53-57 (2014).
Dohnal et al. CD40 ligation restores type 1 polarizing capacity in TLR4-activated dendritic cells that have ceased interleukin-12 expression. J Cell Mol Med 13(8B):1741-1750 (2009).
Doyle et al. 9.1.1 Principles Governing The Use of Cancer Chemotherapy in Palliative Care. Oxford Textbook of Palliative Medicine, Oxford University Press, (p. 255) (1993).
Draghiciou et al. Therapeutic immunization and local low-dose tumor irradiation, a reinforcing combination. Int J Cancer 177(3):311-327 (2012).
Dudek et al. Inducers of Immunogenic Cancer Cell Death. Cytokine Growth Factor Rev 24(4):319-333 (2013).
Eckels et al. Isolation of a Temperature-Sensitive Dengue-2 Virus Under Conditions Suitable for Vaccine Development. Infect Immun 14(5):1221-1227 (1976).
Edelman et al. A live attenuated dengue-1 vaccine candidate (45AZ5) passaged in primary dog kidney cell culture is attenuated and immunogenic for humans. J Infect Dis. 170(6):1448-1455 (1994).
Ellem et al. The labyrinthine ways of cancer immunotherapy-T cell, tumor cell encounter: 'How do I lose thee? Let me count the ways'. Ad Cancer Res 75:203-249 (1998).
Endy. Human immune responses to dengue virus infection: lessons learned from prospective cohort studies. Front Immunol 5:183 (2014).
Flavell et al. The polarization of immune cells in the tumour environment by TGFβ. Nat Rev Immunol 10(8):554-567 (2010).
Fracol et al. Response to HER-2 pulsed DC1 vaccines is predicted by both HER-2 and estrogen receptor expression in DCIS. Ann Surg Oncol 20(10):3233-3239 (2013).
Franciszkiewicz et al. CD103 or LFA-1 engagement at the immune synapse between cytotoxic T cells and tumor cells promotes maturation and regulates T-cell effector functions. Cancer Res 73(2):617-628 (2013).
Gabrilovitch et al. Dendritic cells in antitumor immune responses. II. Dendritic cells grown from bone marrow precursors, but not mature DC from tumor-bearing mice, are effective antigen carriers in the therapy of established tumors. Cell Immunol 70(1):111-119 (1996).
Ganss et al. Combination of T-cell therapy and trigger of inflammation induces remodeling of the vasculature and tumor eradication. Cancer Research 62:1462-1470 (2002).
Genevive et al. CD40-CD40 Ligand Interaction between Dendritic Cells and CD8+ T Cells Is Needed to Stimulate Maximal T Cell Responses in the Absence of CD4+ T Cell Help. J Immunol 178(5):2844-2852 (2007).
George et al. Chapter 5: Clinical spectrum of dengue infection. Dengue and Dengue Hemorrhagic Fever (Gubler and Kuno, CAB International) (25 pgs) (1997).
Gervais et al. In vitro antitumor lymphocyte generation using dendritic cells and innate immunity mechanisms as tumor cell treatments. Anticancer Res 27(4B):2385-2392 (2007).
Gottardis et al. Estradiol-stimulated growth of MCF-7 tumors implanted in athymic mice: a model to study the tumoristatic action of tamoxifen. J Steroid Biochem 30: 311-314 (1988).
Gupta et al. Acute disseminated encephalomyelitits associated with dengue infection, a case report with literature review. J Neurol Sci 335(1-2):216-218 (2013).
Habaragamuwa et al. N-acetylcystein in dengue-associated severe hepatitis. Indian J Crit Care Med 18(3):181-184 (2014).
Hahn et al. Nucleotide sequence of dengue 2 RNA and comparison of the encoded proteins with those of other flaviviruses. Virology 162:167-180 (1988).
Halstead. Etiologies of the Experimental Dengues of Siler and Simmons. Am J Trap Med Hys 23:974-982 (1974) (http://www.ajtmh.org/content/23/5/974.long).
Harris et al. Rapid subtyping of dengue viruses by restriction site-specific (RSS)-PCR. Virology 253:86-95 (1999).
Heylmann et al. Radiation sensitivity of human and murine peripheral blood lymphocytes, stem, and progenitor cells. Biochim Biophys Acta 1846(1):121-129 (2014).
Hiroshi Fukuhara, et al., "Oncolytic virus therapy: A new era of cancer treatment at dawn", Cancer Science, vol. 107, No. 10, Sep. 9, 2016, pp. 1373-1379.
Hober et al. High levels of sTNFR p75 and TNF alpha in dengue-infected patients. Microbiol Immunol 40:569-573 (1996).
Hollen et al. Measurement of quality of life in patients with lung cancer in multicenter trials of new therapies. Cancer 73:2087-2098 (1994).
Hung. Fluid Management for dengue in children. Paediatrics and Child Health 32(S-1):39-42 (2012).
Islas-Rodríguez et al. Effect of in vitro infection with dengue virus (DEN-2) on various cellular immune response functions in the mouse. Archives de Investiga cion Medica 21(2):87-93 (1990) (English Abstract).
Janikashvili et al. Personalized dendritic cell-based tumor immunotherapy. Immunotherapy 2(1):57-68 (2010).
Jing et al. Combined immune checkpoint protein blockade and low dose whole body irradiation as immunotherapy for myeloma. J ImmunoTher Cancer 3(1):2 (15 pgs) (2015).

(56) References Cited

OTHER PUBLICATIONS

Kaka et al. Using Dendritic Cell Maturation and IL-12 Producing Capacity as Markers of Function: A Cautionary Tale. J Immunother 31(4):359-369 (2008).
Kawasaki et al. Toll-Like Receptor Signaling Pathways. Fron Immunol 5:461 (2014).
Kelley et al. Dengue Hemorrhagic Fever-Associated Immunomediators Induced via maturation of Dengue Virus Nonstructural 4B Protein in Monocytes Modulate Endothelial Cell Adhesion Molecules and Human Microvascular Endothelial Cells Permeability. Virology 422(2):326-337 (2012).
Khan et al. The Evolving Role of Radiation Therapy in the Management of Malignant Melanoma. Int J Radiat Oncol Biol Phys 80(3):645-654 (2011).
Kuo et al. Liver biochemical tests and dengue fever. Am J Trap Med Hyg 47:265-270 (1992).
Kurane et al. Activation of T lymphocytes in dengue virus infections. High levels of soluble interleukin 2 receptor, soluble CD4, soluble CD8, interleukin 2, and interferon-gamma in sera of children with dengue. J Clin Invest 88:1473-1480 (1991).
Kurane et al. Dengue virus infection of human skin fibroblasts in vitro production of IFN-Beta, IL-6, and GM-CSF. Arch Virol 124:21-30 (1992).
Kurlander et al. A functional comparison of mature human dendritic cells prepared in fluorinated ethylene-propylene bags or polystyrene flasks. Transfusion 46(9):1494-1504 (2006).
Kuss et a. Clinical significance of decreased zeta chain expression in peripheral blood lymphocytes of patients with head and neck cancer. Clin Cancer Res 5:329-334(1999).
Lambert et al. Intradermal vaccine delivery: will new delivery systems transform vaccine administration? Vaccine 26:3197-3208 (2008).
Lee et al. Acute myocarditis in dengue hemorrhagic fever: a case report and review of cardiac complications in dengue-affected patients. Int J Infect Dis 14:e919-e922 (2010).
Lee et al. Clinical characteristics, risk factors, and outcomes in adults experiencing DHF complicated with acute renal failure. Am J Trap Med Hyg 80(4): 651-655 (2009).
Leitmeyer et al. Dengue Virus structural changes that correlate with pathogenesis. J Virol 73:4738-4747 (1999).
Lesterhaus et al. Dendritic Cell vaccines in melanoma: from promise to proof? Crit Rev Oncol Hematol 66(2):118-134 (2008).
Linette et al. Cardiovascular toxicity and titin cross-reactivity of affinity-enhanced T cells in myeloma and melanoma. Blood 122(6):863-871 (2013).
Lizarraga et al. Dengue-associated kidney disease. J Nephropathol 3(2):57-62 (2014).
Lum et al. Dengue-associated adult respiratory distress syndrome. Ann Trap Paediatr 15(4):335-339 (1995).
Lutz et al. An advanced culture method for generating large quantities of highly pure dendritic cells from mouse bone marrow. J Immunol Methods 223:77-92 (1999).
Lövgren et al. Enhanced stimulation of human tumor-specific T cells by dendritic cells matured in the presence of interferon-γ and multiple toll-like receptor agonists. Cancer Immunol Immunother 66(10):1333-1344 (2017).
Lyday et al. Overcoming tumor immune evasion with an unique arbovirus. J Transl Med 13:3 (2015) (12 pgs).
Ma et al. The TLR7 agonists imiquimod and gardiquimod improve DC-based immunotherapy for melanoma in mice. Cell Mol Immunol 7(5):381-388 (2010).
MACS® GMP Cell Differentiation Bag. Miltenyi Biotec Product Insert. Issued: Aug. 2012 (2 pgs).
Malavige et al. T cell responses in dengue viral infections. J Clin Virol 58(4):605-611 (2013).
Malik et al. Dengue encephalopathy-still and enigma? J Infect Dev Ctries 8(8):1076-1078 (2014).
Markiewicz et al. IL-12 enhances CTL synapse formation and induces self-reactivity. J Immunol 182(3):1351-1361 (2009).
Matthew et al. Dominant recognition by human CD8+ CTL of dengue virus non-structural proteins NS3 and NS1.2a. J Clin Invest 98:1684-1691 (1996).
McKee et al. Lack of attenuation of a candidate Dengue-1 vaccine (45AZ5), in human volunteers. Am J Trap Med Hyg Mar. 36:435-442 (1987).
Media For Multiplitoplasma Viroids Is Not Rare—Causative Agent (available at https://www.alpfmedical.info/causative-agent/i-ptg.html) ALPF Medical Research (5 pgs) (updated Jul. 21, 2017).
Mettler et al. Virus Inoculation in Mice Bearing Ehrlich Ascitic Tumors: Antigen Prouction and Tumor Regression. Infect Immun 37(1):23-27 (1982).
Mittendorf et al. Final report of the phase I/II clinical trial of the E75 (nelipepimut-S) vaccine with booster inoculations to prevent disease recurrence in high-risk breast cancer patients. Ann Oncol 25(9):1735-1742 (2014).
Mizoguchi et al. Alterations in signal transduction molecules in T lymphocytes from tumor-bearing mice. Science 258:1795-1798 (1992).
Moore, Alice E., "Viruses With Oncolytic Properties and Their Adaptation to Tumors", Annals of the New York Academy of Sciences, (1952) vol. 54, Issue 6 pp. 945-952.
Morse et al. Migration of human DC after injection in Patients with Metastatic Malignancies. Cancer Res 59:56-58 (1999).
Nakai et al. Immunoregulatory T cells in the peripheral blood of melanoma patients treated with melanoma antigen-pulsed dendritic cell vaccination. J Dermatol Sci 54:31-37 (2009).
Napolitani et al. Selected Toll-like receptor agonist combinations synergistically trigger a T helper type 1-polarizing program in dendritic cells. Nat Immunol 6(8):769-776 (2005).
Nava et al. An optimized method for manufacturing a clinical-scale Dendritic Cell-based vaccine for the treatment of Glioblastoma. PLoS One 7(12):e52301 (2012).
Nielsen. The Relationship of intersecting immunological components in Dengue pathogenesis. Virol J 6:1-7 (2009).
Nocera et al. Restoring Lost Anti-HER-2 Th1 Immunity in Breast Cancer: A Crucial Role for Th1 Cytokines in Therapy and Prevention. Front Pharmacol 7:356 (2016).
Nunes et al. Emergence and potential for spread of Chikungunya virus in Brazil. BMC Medicine 13:102 (2015).
Oken et al. Toxicity And Response Criteria Of The Eastern Cooperative Oncology Group. Am J Clin Oncol 5:649-655 (1982).
Oleinika et al. Suppression, subversion, and escape: the role of regulatory T cells in cancer progression. Clin Exp Immunol 171:36-45 (2012).
Olszanski. Current and Future Roles of Targeted Therapy and Immunotherapy in Advanced Melanoma. J Manag Care Pharm 20(4):346-354 (2014).
Osborne et al. Effects of estrogens and antiestrogens on growth of human breast cancer cells in athymic nude mice. Cancer Res 45:584-590 (1985).
O'Toole et al. Evaluating cancer patients for rehabilitation potential. West J Med 155:384-387 (1991).
Park et al. Radiation-induced vascular damage in tumors: implications of vascular damage in ablative hypofractionated radiotherapy (SBRT and SRS). Radiat Res 177(3):311-327 (2012).
Pasca et al. Role of Interleukin-12 in patients with dengue hemorrhagic fever. FEMS Immunol Med Microbiol 28:151-155 (2000).
Paustian et al. Effect of multiple activation stimuli on the generation of Th1-polarizing dendritic cells. Hum Immuon 71(1):24-31 (2011).
PCT/US2016/040787 International Preliminary Report on Patentability dated Jan. 11, 2018.
PCT/US2016/040787 International Search Report and Written Opinion dated Sep. 22, 2016.
PCT/US2016/053554 International Preliminary Report on Patentability dated Apr. 5, 2018.
PCT/US2016/053554 International Search Report and Written Opinion dated Feb. 3, 2017.
PCT/US2016/053554 Invitation to Pay Additional Fees dated Nov. 28, 2016.
PCT/US2017/061810 International Search Report and Written Opinion dated Mar. 15, 2018.

(56) References Cited

OTHER PUBLICATIONS

PCT/US2017/061810 Invitation to Pay Additional Fees dated Jan. 22, 2018.
PCT/US2018/012408 International Search Report and Written Opinion dated Mar. 29, 2018.
PCT/US2018/037616 International Search Report and Written Opinion dated Nov. 29, 2018.
Pfeiffer. Dissertation—Generation of effective designer dendritic cells for therapeutic cancer vaccination using RNA electroporation. The Faculty of Science, University of Erlangen-Nuremberg (146 pgs) (2013) (w/English translation).
Prestwich et al. The case of oncolytic viruses versus the immune system: waiting on the judgment of Solomon. Hum Gene Ther 20(10):1119-1132 (2009).
Quatromonie et al. The timing of TGF-β inhibition affects the generation of antigen-specific CD8+ T cells. BMC Immunol 14:30 (2013).
Rajat et al. Unusual manifestations in dengue outbreak 2009, Delhi, India. J Communicable Dis 42(4):255-261 (2010).
Rigau-Perez et al. Dengue activity in Puerto Rico, 1990. Puerto Rico Health Science Journal 11(2):65-68 (1992).
Rouas et al. Dendritic cells generated in clinical grade bags strongly differ in immune functionality when compared with classical DCs generated in plates. J Immunother 33(4):352-363 (2010).
Santos et al. Dendritic Cell-Based Cancer Vaccines. J Immunol 200(2):443-449 (2018).
Schag et al. Karnofsky performance status revisited: Reliability, validity,and guidelines. J Clin Oncol 2:187-193 (1984).
Sharma et al. Guillain-Barre syndrome occurring during dengue fever. J Indian Med Assoc 109(9):675 and 682 (2011).
Sheikh et al. Sipuleucel-T immune parameters correlate with survival: an analysis of the randomized phase 3 clinical trials in men with castration-resistant prostate cancer. Cancer Immunol Immunother 62(1):137-147 (2013).
Shresta et al. Critical roles for both STAT1-dependent and STAT1-independent pathways in the control of primary dengue virus infection in mice. J Immunol 175:3946-3954 (2005).
Singhi et al. Dengue and Dengue Hemorrhagic Fever: management issues in an intensive care unit. J Pediatr (Rio J) 83(Supp 2):S22-S35 (2007).
Sinkovics et al. New Developments in the Virus Therapy of Cancer: A Historical Review. Intervirology 36:193-214 (1993).
Sondak et al. Allogeneic and autologous melanoma vaccines: where have we been and where are we going? Clin Cancer Res 12(7 Pt 2):2337s-2341s (2006).
Sorlie et al. Gene expression patterns of breast carcinomas distinguish tumor subclasses with clinical implications. PNAS USA 98:10869-10874 (2001).
Stanton et al. Clinical significance of tumor-infiltrating lymphocytes in breast cancer. J Immunother Cancer 4:59 (2016).
Straussman et al. Tumour micro-environment elicits innate resistance to RAF inhibitors through HGF secretion. Nature 487:500-504 (2012).
Taweechaisupapong et al. Langerhans cell density and serological changes following intradermal immunisation of mice with dengue 2 virus. J Med Microbiol 45:138-145 (1996).
Turcotte et al. Immunotherapy for metastatic solid cancers. Adv Surg 45:341-360 (2011).
Turnis et al. Enhancement of dendritic cells as vaccines for cancer. Immunotherapy 2(6):847-862 (2010).
U.S. Appl. No. 15/200,751 Office Action dated Feb. 7, 2017.
U.S. Appl. No. 15/275,073 Office Action dated Aug. 15, 2018.
U.S. Appl. No. 15/275,073 Office Action dated Aug. 30, 2019.
U.S. Appl. No. 15/275,073 Office Action dated Jan. 17, 2020.
U.S. Appl. No. 15/275,073 Office Action dated Jan. 28, 2019.
U.S. Appl. No. 15/275,073 Office Action dated Jul. 14, 2017.
U.S. Appl. No. 15/275,073 Office Action dated Mar. 31, 2017.
U.S. Appl. No. 15/639,632 Office Action dated Aug. 3, 2017.
U.S. Appl. No. 15/799,793 Office Action dated Dec. 13, 2017.
U.S. Appl. No. 15/799,793 Office Action dated May 25, 2018.
U.S. Appl. No. 16/172,487 Office Action dated Dec. 14, 2018.
U.S. Appl. No. 16/413,444 Office Action dated Aug. 19, 2019.
U.S. Appl. No. 16/413,444 Office Action dated Nov. 20, 2019.
Valerio et al. Hemorrhagic exanthema due to dengue virus induced by Acetylsalicylic acid. An Sist Sancit Navar 29(3):439-442 (2006).
Van Mierlo et al. Activation of dendritic cells that cross-present tumor-derived antigen licenses CD8+ CTL to cause tumor destruction. J Immunol 173:6753-6759 (2004).
Vaughn et al. Dengue viremia titer, Antibody Response Pattern, and Virus Serotype Correlate with Disease Sensitivity. J Infect Dis 181:2-9 (2000).
Verdijik et al. Limited amounts of DC migrate into the T-cell area of lymph nodes, but have high immune activating potential in melanoma patients. Clin Can Res 15(7):2531-2540 (2009).
Via et al. IL-12 stimulates the development of acute graft-versus-host disease in mice that normally would develop chronic, autoimmune graft-versus-host disease. J Immunol 153(9):4040-4047 (1994).
Wahid et al. A comparison of the pattern of liver involvement in Dengue Hemorrhagic Fever with classic Dengue Fever. Southeast Asian J Trap Med Public Health 31(2):259-263 (2000).
Wolchok et al. Guidelines for the evaluation of immune therapy activity in solid tumors: immune-related response criteria. Clin Cancer Res 15(23):7412-7420 (2009).
Wolchok et al. Nivolumab plus ipilimumab in advanced melanoma. N Eng J Med. 369:122-133(2013).
Wu et al. Human skin Langerhans cells are targets of dengue virus infection. Nature Medicine 6:816-820 (2000).
Xu et al. High-avidity antitumor T-cell generation by toll receptor 8-primed, myeloid-derived dendritic cells is mediated by IL-12 production. Surgery 140(2):170-178 (2006).
Yang et al. TGF-beta and immune cells: an important regulatory axis in the tumor microenvironment and progression. Trends Immunol 31(6):220-227 (2010).
Yeo et al. Lack of clinical manifestations in asymptomatic dengue infection is attributed to broad down-regulation and selective up-regulation of host defence response genes. PloS One 9(4):e92240 (2014).
Yu et al. New Immunotherapy Strategies in Breast Cancer. Int J Environ Res Public Health 14(1):pii:68 (2017).
Zellweger et al. Mouse models to study dengue virus immunology and pathogenesis. Front Imunol 10(5):151 (Apr. 2014).
Zitvogel et al. Therapy of murine tumors with tumor-peptide-pulsed dendritic cells: dependence on T cells, B7 costimulation, and T-helper cell-1 associated cytokines. J Exp Med 183:87-97 (1996).
Zobywalski et al. Generation of clinical grade dendritic cells with capacity to produce biologically active IL-12p70. J Transl Med 5:18 (2007).
Lyday, et al., "Triad Immunologies, LLC, Presents: Hyperthermia + Cytokine Cascade Dendritic Cell Vaccine for Solid Tumors"; Slides published May 1, 2011, pp. 1-40.
Zhao, Danhua et al.: "Live attenuated measles virus vaccine induces apoptosis and promotes tumor regression in lung cancer", Oncology Reports, 29:1, Oct. 29, 2012.
Sancho, D. et al., Tumor therapy in mice via antigen targeting to a novel, DC-restricted c-type lectin, J. Clin. Invest., 2008, vol. 118(6), pp. 2098-2110.
Fukuhara, Hiroshi et al., "Oncolytic virus therapy: A new era of cancer treatment at dawn". Cancer Science, vol. 107(10) Sep. 9, 2016, pp. 1373-1379.
Ya et al.,"Mouse Model for Pre-Clinical Study of Human Cancer Immunotherapy", Current protocols in immunology (2015), 108. 20.1.1-20.1.43. 10.1002/0471142735.im2001s108.
Fischer et al., "Vaccine-induced CD8 T cells are redirected with peptide-MHC class I-IgG antibody fusion proteins to eliminate tumor cells in vivo", (2020) mAbs, 12:1, DOI: 10.1080/19420862.2020.1834818.
Bergman, L. et al., "Uveal Melanoma: a Study on Incidence of Additional Cancers in the Swedish Population", Invest. Ophthalmol. Vis. Sci., 2006, vol. 47(1), pp. 72-77.
Bradford, P. T. et al., "Increased Risk of Second Primary Cancers After a Diagnosis of Melanoma", Arch. Dermatol., 2010, vol. 146(3), pp. 265-272.

(56) References Cited

OTHER PUBLICATIONS

Pandurengan, R. K. et al., Survival of Patients with Multiple Primarymalignancies: a Study of 783 Patients with Gastrointestinal Stromal Tumor, Ann. Oncol., 2010, vol. 21(10), pp. 2107-2111.

SEQUENCE LISTING

```
<160> NUMBER OF SEQ ID NOS: 34

<210> SEQ ID NO 1
<211> LENGTH: 288
<212> TYPE: PRT
<213> ORGANISM: Homo sapiens
```

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

```
Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 3
<211> LENGTH: 223
<212> TYPE: PRT
<213> ORGANISM: Homo sapiens

<400> SEQUENCE: 3

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
            130                 135                 140

Asn Gly Thr Gln Ile Tyr Val Ile Asp Pro Glu Pro Cys Pro Asp Ser
145                 150                 155                 160
```

```
Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 4
<211> LENGTH: 360
<212> TYPE: PRT
<213> ORGANISM: Homo sapiens

<400> SEQUENCE: 4

Met Trp Glu Ala Gln Phe Leu Gly Leu Leu Phe Leu Gln Pro Leu Trp
  1               5                  10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
```

| | | | | | | | | | | | |
|---|---|---|---|---|---|---|---|---|---|---|---|
| | | 305 | | | 310 | | | 315 | | | 320 |

Glu Asp Val Ser Gln Ala Gln Ala Gly Thr Tyr Thr Cys His Ile His
                            325                          330                          335

Leu Gln Glu Gln Gln Leu Asn Ala Thr Val Thr Leu Ala Ile Ile Thr
                            340                          345                          350

Gly Gln Pro Gln Val Gly Lys Glu
                            355                          360

<210> SEQ ID NO 5
<211> LENGTH: 534
<212> TYPE: PRT
<213> ORGANISM: Homo sapiens

<400> SEQUENCE: 5

Met Leu Arg Arg Arg Gly Ser Pro Gly Met Gly Val His Val Gly Ala
1                  5                       10                      15

Ala Leu Gly Ala Leu Trp Phe Cys Leu Thr Gly Ala Leu Glu Val Gln
                          20                         25                       30

Val Pro Glu Asp Pro Val Val Ala Leu Val Gly Thr Asp Ala Thr Leu
            35                      40                       45

Cys Cys Ser Phe Ser Pro Glu Pro Gly Phe Ser Leu Ala Gln Leu Asn
    50                          55                          60

Leu Ile Trp Gln Leu Thr Asp Thr Lys Gln Leu Val His Ser Phe Ala
65                 70                      75                      80

Glu Gly Gln Asp Gln Gly Ser Ala Tyr Ala Asn Arg Thr Ala Leu Phe
                        85                          90                       95

Pro Asp Leu Leu Ala Gln Gly Asn Ala Ser Leu Arg Leu Gln Arg Val
            100                    105                    110

Arg Val Ala Asp Glu Gly Ser Phe Thr Cys Phe Val Ser Ile Arg Asp
        115                    120                    125

Phe Gly Ser Ala Ala Val Ser Leu Gln Val Ala Ala Pro Tyr Ser Lys
    130                        135                    140

Pro Ser Met Thr Leu Glu Pro Asn Lys Asp Leu Arg Pro Gly Asp Thr
145                150                    155                    160

Val Thr Ile Thr Cys Ser Ser Tyr Gln Gly Tyr Pro Glu Ala Glu Val
                165                    170                    175

Phe Trp Gln Asp Gly Gln Gly Val Pro Leu Thr Gly Asn Val Thr Thr
            180                    185                    190

Ser Gln Met Ala Asn Glu Gln Gly Leu Phe Asp Val His Ser Ile Leu
        195                    200                    205

Arg Val Val Leu Gly Ala Asn Gly Thr Tyr Ser Cys Leu Val Arg Asn
    210                        215                    220

Pro Val Leu Gln Gln Asp Ala His Ser Ser Val Thr Ile Thr Pro Gln
225                230                    235                    240

Arg Ser Pro Thr Gly Ala Val Glu Val Gln Val Pro Glu Asp Pro Val
                245                    250                    255

Val Ala Leu Val Gly Thr Asp Ala Thr Leu Arg Cys Ser Phe Ser Pro
            260                    265                    270

Glu Pro Gly Phe Ser Leu Ala Gln Leu Asn Leu Ile Trp Gln Leu Thr
        275                    280                    285

Asp Thr Lys Gln Leu Val His Ser Phe Thr Glu Gly Arg Asp Gln Gly
    290                        295                    300

Ser Ala Tyr Ala Asn Arg Thr Ala Leu Phe Pro Asp Leu Leu Ala Gln
305                310                    315                    320

```
Gly Asn Ala Ser Leu Arg Leu Gln Arg Val Arg Val Ala Asp Glu Gly
            325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
            450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
            485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
            515                 520                 525

Asp Gly Gln Glu Ile Ala
            530

<210> SEQ ID NO 6
<211> LENGTH: 341
<212> TYPE: PRT
<213> ORGANISM: Homo sapiens

<400> SEQUENCE: 6

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
            35                  40                  45

Cys Trp Ser Asp Val Arg Phe Glu His Phe Leu Leu His Arg Glu Gly
50                  55                  60

Lys Tyr Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
            85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
            115                 120                 125

Pro Ser Leu Ser Ala Gln Pro Gly Pro Thr Val Leu Ala Gly Glu Ser
130                 135                 140

Val Thr Leu Ser Cys Ser Ser Arg Ser Ser Tyr Asp Met Tyr His Leu
145                 150                 155                 160
```

Ser Arg Glu Gly Glu Ala His Glu Arg Arg Phe Ser Ala Gly Pro Lys
            165                 170                 175

Val Asn Gly Thr Phe Gln Ala Asp Phe Pro Leu Gly Pro Ala Thr His
        180                 185                 190

Gly Gly Thr Tyr Arg Cys Phe Gly Ser Phe Arg Asp Ser Pro Tyr Glu
            195                 200                 205

Trp Ser Asn Ser Ser Asp Pro Leu Leu Val Ser Val Thr Gly Asn Pro
        210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Ile Ile Leu
                245                 250                 255

Phe Ile Leu Leu Leu Phe Phe Leu Leu His Arg Trp Cys Cys Asn Lys
            260                 265                 270

Lys Asn Ala Val Val Met Asp Gln Glu Pro Ala Gly Asn Arg Thr Val
        275                 280                 285

Asn Arg Glu Asp Ser Asp Glu Gln Asp Pro Gln Glu Val Thr Tyr Ala
        290                 295                 300

Gln Leu Asn His Cys Val Phe Thr Gln Arg Lys Ile Thr His Pro Ser
305                 310                 315                 320

Gln Arg Pro Lys Thr Pro Pro Thr Asp Ile Ile Val Tyr Thr Glu Leu
                325                 330                 335

Pro Asn Ala Glu Pro
            340

<210> SEQ ID NO 7
<211> LENGTH: 255
<212> TYPE: PRT
<213> ORGANISM: Homo sapiens

<400> SEQUENCE: 7

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu

```
                    180                 185                 190
Ala Leu Thr Ser Thr Ala Leu Leu Phe Leu Leu Phe Phe Leu Thr Leu
                195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 8
<211> LENGTH: 260
<212> TYPE: PRT
<213> ORGANISM: Homo sapiens

<400> SEQUENCE: 8

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 9
<211> LENGTH: 241
<212> TYPE: PRT
<213> ORGANISM: Homo sapiens
```

<400> SEQUENCE: 9

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

<210> SEQ ID NO 10
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
```

```
                100             105             110
Gly Thr Thr Val Thr Val Ser Ser Ala Ser Thr Lys Gly Pro Ser Val
            115             120             125

Phe Pro Leu Ala Pro Cys Ser Arg Ser Thr Ser Glu Ser Thr Ala Ala
            130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Lys Thr Tyr Thr Cys Asn Val Asp His Lys
            195             200             205

Pro Ser Asn Thr Lys Val Asp Lys Arg Val Glu Ser Lys Tyr Gly Pro
            210             215             220

Pro Cys Pro Pro Cys Pro Ala Pro Glu Phe Leu Gly Gly Pro Ser Val
225             230             235             240

Phe Leu Phe Pro Pro Lys Pro Lys Asp Thr Leu Met Ile Ser Arg Thr
            245             250             255

Pro Glu Val Thr Cys Val Val Val Asp Val Ser Gln Glu Asp Pro Glu
            260             265             270

Val Gln Phe Asn Trp Tyr Val Asp Gly Val Glu Val His Asn Ala Lys
            275             280             285

Thr Lys Pro Arg Glu Glu Gln Phe Asn Ser Thr Tyr Arg Val Val Ser
            290             295             300

Val Leu Thr Val Leu His Gln Asp Trp Leu Asn Gly Lys Glu Tyr Lys
305             310             315             320

Cys Lys Val Ser Asn Lys Gly Leu Pro Ser Ser Ile Glu Lys Thr Ile
            325             330             335

Ser Lys Ala Lys Gly Gln Pro Arg Glu Pro Gln Val Tyr Thr Leu Pro
            340             345             350

Pro Ser Gln Glu Glu Met Thr Lys Asn Gln Val Ser Leu Thr Cys Leu
            355             360             365

Val Lys Gly Phe Tyr Pro Ser Asp Ile Ala Val Glu Trp Glu Ser Asn
            370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
            405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser
            435             440

<210> SEQ ID NO 11
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Ile Val Leu Thr Gln Ser Pro Ala Thr Leu Ser Leu Ser Pro Gly
1               5               10              15
```

-continued

```
Glu Arg Ala Thr Leu Ser Cys Arg Ala Ser Lys Gly Val Ser Thr Ser
             20                  25                  30

Gly Tyr Ser Tyr Leu His Trp Tyr Gln Gln Lys Pro Gly Gln Ala Pro
         35                  40                  45

Arg Leu Leu Ile Tyr Leu Ala Ser Tyr Leu Glu Ser Gly Val Pro Ala
     50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 12
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Val Gln Leu Val Glu Ser Gly Gly Gly Val Val Gln Pro Gly Arg
1               5                  10                  15

Ser Leu Arg Leu Asp Cys Lys Ala Ser Gly Ile Thr Phe Ser Asn Ser
             20                  25                  30

Gly Met His Trp Val Arg Gln Ala Pro Gly Lys Gly Leu Glu Trp Val
         35                  40                  45

Ala Val Ile Trp Tyr Asp Gly Ser Lys Arg Tyr Tyr Ala Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
        210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
            Glu Asp Phe Ala Val Tyr Tyr Cys Gln Gln Ser Ser Asn Trp Pro Arg
                            85                  90                  95

Thr Phe Gly Gln Gly Thr Lys Val Glu Ile Lys Arg Thr Val Ala Ala
                            100                 105                 110

Pro Ser Val Phe Ile Phe Pro Pro Ser Asp Glu Gln Leu Lys Ser Gly
                            115                 120                 125

Thr Ala Ser Val Val Cys Leu Leu Asn Asn Phe Tyr Pro Arg Glu Ala
                            130                 135                 140

Lys Val Gln Trp Lys Val Asp Asn Ala Leu Gln Ser Gly Asn Ser Gln
            145                 150                 155                 160

Glu Ser Val Thr Glu Gln Asp Ser Lys Asp Ser Thr Tyr Ser Leu Ser
                            165                 170                 175

Ser Thr Leu Thr Leu Ser Lys Ala Asp Tyr Glu Lys His Lys Val Tyr
                            180                 185                 190

Ala Cys Glu Val Thr His Gln Gly Leu Ser Ser Pro Val Thr Lys Ser
                            195                 200                 205

Phe Asn Arg Gly Glu Cys
                            210

<210> SEQ ID NO 14
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
            1               5                   10                  15

Ser Leu Arg Leu Ser Cys Ala Ala Ser Gly Phe Thr Phe Ser Asp Ser
                            20                  25                  30

Trp Ile His Trp Val Arg Gln Ala Pro Gly Lys Gly Leu Glu Trp Val
                            35                  40                  45

Ala Trp Ile Ser Pro Tyr Gly Gly Ser Thr Tyr Tyr Ala Asp Ser Val
                50                  55                  60

Lys Gly Arg Phe Thr Ile Ser Ala Asp Thr Ser Lys Asn Thr Ala Tyr
            65                  70                  75                  80

Leu Gln Met Asn Ser Leu Arg Ala Glu Asp Thr Ala Val Tyr Tyr Cys
                            85                  90                  95

Ala Arg Arg His Trp Pro Gly Gly Phe Asp Tyr Trp Gly Gln Gly Thr
                            100                 105                 110

Leu Val Thr Val Ser Ser Ala Ser Thr Lys Gly Pro Ser Val Phe Pro
                            115                 120                 125

Leu Ala Pro Ser Ser Lys Ser Thr Ser Gly Gly Thr Ala Ala Leu Gly
                            130                 135                 140

Cys Leu Val Lys Asp Tyr Phe Pro Glu Pro Val Thr Val Ser Trp Asn
            145                 150                 155                 160

Ser Gly Ala Leu Thr Ser Gly Val His Thr Phe Pro Ala Val Leu Gln
                            165                 170                 175

Ser Ser Gly Leu Tyr Ser Leu Ser Ser Val Val Thr Val Pro Ser Ser
                            180                 185                 190

Ser Leu Gly Thr Gln Thr Tyr Ile Cys Asn Val Asn His Lys Pro Ser
                            195                 200                 205
```

```
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Ala Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 17
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Gly Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Phe Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210             215

<210> SEQ ID NO 18
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val His Gln Asp Trp Leu Asn Gly
305                 310                 315                 320
```

```
Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 20
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Glu Val Gln Leu Gln Gln Ser Gly Pro Glu Leu Lys Pro Gly Ala
1               5                   10                  15

Ser Val Lys Leu Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly His Ile Asp Pro Tyr Tyr Gly Asp Thr Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Val Lys Gly Gly Tyr Tyr Gly His Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 21
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Gly Pro Asp Gly Thr Ile Lys Arg Leu Ile
        35                  40                  45

Tyr Ala Thr Ser Ser Leu Asp Ser Gly Val Pro Lys Arg Phe Ser Gly
50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Val Ser Ser Pro Pro
                85                  90                  95

Thr Phe Gly Ala Gly Thr Lys Leu Glu Leu Lys Arg Ala Asp Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 450
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 22

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Phe Tyr
            20                  25                  30
Ala Ile Ser Trp Val Arg Gln Ala Pro Gly Gln Gly Leu Glu Trp Met
        35                  40                  45
Gly Gly Phe Ile Pro Ile Phe Gly Ala Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Asp Asp Thr Ala Val Tyr Tyr Cys
                85                  90                  95
Ala Arg Ile Pro Ser Gly Ser Tyr Tyr Tyr Asp Tyr Asp Met Asp Val
            100                 105                 110
Trp Gly Gln Gly Thr Thr Val Thr Val Ser Ser Ala Ser Thr Lys Gly
        115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
```

```
                385                 390                 395                 400
Leu Asp Ser Asp Gly Ser Phe Phe Leu Tyr Ser Arg Leu Thr Val Asp
                    405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 23
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Gln Trp Gly Ala Gly Leu Leu Lys Pro Ser Glu
```

-continued

```
1               5                   10                  15
Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
            35                  40                  45

Gly Glu Ile Asn His Gly Gly Tyr Val Thr Tyr Asn Pro Ser Leu Glu
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430
```

Leu His Asn His Tyr Thr Gln Lys Ser Leu Ser Leu Ser Gly Lys
        435                 440                 445

<210> SEQ ID NO 25
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 26
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Gly Asn Trp Gly Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln
            420

<210> SEQ ID NO 27
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 27

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gly Ser Arg Asn Gln Asp Trp Leu
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Ala Tyr Arg Tyr His Leu Leu
1               5

<210> SEQ ID NO 30
<211> LENGTH: 8
<212> TYPE: PRT
<213> ORGANISM: Gallus gallus

<400> SEQUENCE: 30
```

```
Ser Ile Ile Asn Phe Glu Lys Leu
1               5

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggatcccaag aagggggccat                                              20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggcagctcca tagattgct                                                19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtgttgctg cagatggaa                                                19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgtcacaga cagtgaggt                                                19
```

COMBINATION IMMUNOTHERAPIES FOR TREATMENT OF CANCER

CROSS REFERENCE

This application is a continuation of U.S. application Ser. No. 16/413,444, filed on May 15, 2019 which is a continuation of International Application No. PCT/US2017/061810, filed Nov. 15, 2017, which claims the benefit of U.S. Provisional Application No. 62/423,119, filed Nov. 16, 2016, which are herein incorporated by reference in their entirety.

SEQUENCE LISTING

The instant application contains a Sequence Listing which has been submitted electronically in ASCII format and is hereby incorporated by reference in its entirety. Said ASCII copy, created on Nov. 13, 2017, is named 48253-705_301_SL.txt and is 79,317 bytes in size.

BACKGROUND

Immunotherapy, unlike cytotoxic drugs, radiation, and surgery, stimulates the immune system to recognize and kill tumor cells. Numerous attempts have been made in stimulating the immune system to recognize and destroy tumor cells. These have been met with limited success due to the self-identity of peptides selected as target for immunotherapy, lack of immune activation, adverse events, and/or tumor immune evasion mechanisms.

BRIEF SUMMARY

Provided herein is a method for treatment or reduction of cancer, comprising: administering a strain of an Arbovirus or a strain of an Alphavirus to a subject in need thereof; and administering an immune checkpoint modulatory agent to the subject, wherein the combination of administrations provides for treatment or reduction of a cancer. Further provided is an Arbovirus that is a Dengue virus. Further provided here are methods wherein the Dengue virus is present in an amount of about $10^2$ to about $10^8$ plaque-forming units (PFU)/mL. Further provided here are methods wherein the Dengue virus is present in an amount of Dengue virus can be administered at about $10^5$ PFU/mL. Further provided here are methods wherein the Dengue virus is present in an amount of from about 10,000 to 90,000 PFU/mL. Further provided herein are methods wherein the amount of a Dengue virus can be about 30,000 PFU/mL. Further provided herein is a Dengue virus that is in a volume of about 0.01, 0.02, 0.03, 0.04, 0.05, or 0.1 mL. Further provided herein is a Dengue virus that is in a volume of 0.01 mL to 0.01 mL. Further provided herein is a Dengue virus that is a serotype of at least one of DENV-1, DENV-2, DENV-3, DENV-4, or DENV-5. Further provided is a Dengue virus that is DENV-2 strain #1710. Further provided is a Dengue virus that is 45AZ5, 1710, S16803, HON 1991 C, HON 1991 D, HON 1991 B, HON 1991 A, SAL 1987, TRI 1981, PR 1969, IND 1957, TRI 1953, TSV01, DS09-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750. Further provided is an Alphavirus that is Chikungunya virus. Further provided herein is a cancer that is from the subject. Further provided is an immune checkpoint modulatory agent that modulates the expression or activity of at least one of: CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. Further provided is an immune checkpoint modulatory agent that modulates the expression or activity of at least one of: A2aR, CD276, B7H4, BTLA, CTLA-4, IDO1, IDO2, KIR, LAG3, PD-1, PDL-1, PDL-2, PS, TIM3, or VISTA. Further provided is an immune checkpoint modulatory agent that increases the expression or activity of at least one of: CD122, CD137 (4-1BB), CD137L, CD27, CD28, CD40, CD70, CD80 (B7.1), CD86 (B7.2), GITR, GITRL, ICOS, ICOSL (B7H2), OX-40, or OX-40L. Further provided is an immune checkpoint modulatory agent that is at least one of an antibody, a nucleic acid encoding an antibody, an antigen binding fragment, a RNA interfering agent, a peptide, a peptidomimetic, a small molecule, or an aptamer. Further provided herein is an RNA interfering agent that is a small interfering RNA (siRNA), short hairpin RNA (shRNA), or a microRNA (miRNA). Further provided is an immune checkpoint modulatory agent that is administered in a pharmaceutically acceptable formulation.

Provided herein is a method for treatment or reduction of cancer in a subject in need thereof, comprising: administering a strain of an Arbovirus or a strain of an Alphavirus to a subject in need thereof; administering an immune checkpoint modulatory agent; and administering tumor antigen primed dendritic cells. Further provided herein are tumor antigen primed dendritic cells that target cancer cells. Further provided herein are tumor antigen primed dendritic cells that are cultured on a hard surface. Further provided herein are tumor antigen primed dendritic cells that are autologous or allogeneic. Further provided are primed dendritic cells that produce about 6.5 ng/mL to about 30 ng/mL of IL-12p70. Further provided herein is obtaining dendritic cells from the subject. Further provided herein are dendritic cells that are contacted with a tumor cell lysate, wherein the tumor cell lysate is from the subject, thereby generating tumor antigen primed dendritic cells. Further provided herein is an Arbovirus that is Dengue virus. Further provided here are methods wherein the Dengue virus is present in an amount of about $10^2$ to about $10^8$ plaque-forming units (PFU)/mL. Further provided here are methods wherein the Dengue virus is present in an amount of Dengue virus can be administered at about $10^5$ PFU/mL. Further provided here are methods wherein the Dengue virus is present in an amount of from about 10,000 to 90,000 PFU/mL. Further provided herein are methods wherein the amount of a Dengue virus can be about 30,000 PFU/mL. Further provided herein is a Dengue virus that is in a volume of about 0.01, 0.02, 0.03, 0.04, 0.05, or 0.1 mL. Further provided herein is a Dengue virus that is in a volume of 0.01 mL to 0.01 mL. Further provided is a Dengue virus that is a serotype of at least one of DENV-1, DENV-2, DENV-3, DENV-4, or DENV-5. Further provided is a Dengue virus that is DENV-2 strain #1710. Further provided is a Dengue virus is 45AZ5, 1710, S16803, HON 1991 C, HON 1991 D, HON 1991 B, HON 1991 A, SAL 1987, TRI 1981, PR 1969, IND 1957, TRI 1953, TSV01, DS09-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750. Further provided is an Alphavirus that is Chikungunya virus. Further provided are tumor antigen primed dendritic cells that produce at least about 6.5 ng/mL IL-12p70. Further provided is an immune checkpoint modulatory agent that modulates the expression or activity of at least one of: CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. Further provided is an immune checkpoint modulatory agent that modulates the expression or activity of at least one of: A2aR, CD276, B7H4, BTLA, CTLA-4, IDO1, IDO2, KIR, LAG3, PD-1, PDL-1, PDL-2, PS, TIM3, or VISTA. Further provided is an immune checkpoint modulatory agent that increases the expression or activity of at least one of CD122, CD137 (4-1BB), CD137L, CD27, CD28, CD40, CD70, CD80 (B7.1), CD86 (B7.2), GITR, GITRL, ICOS, ICOSL (B7H2), OX-40, or OX-40L. Further provided is an immune checkpoint modulatory agent that is at least one of an antibody, a nucleic acid encoding an antibody, an antigen binding fragment, a RNA interfering agent, a peptide, a peptidomimetic, a small molecule, or an aptamer. Further provided is an RNA interfering agent that is a small interfering RNA (siRNA), short hairpin RNA (shRNA), or a microRNA (miRNA). Further provided is an immune checkpoint modulatory agent that is administered in a pharmaceutically acceptable formulation.

Provided herein are methods for treatment or reduction of a cancer in a subject in need thereof, comprising: administering primed dendritic cells to target cancer cells; administering a strain of an Arbovirus or a strain of an Alphavirus to the subject; and administering an immune checkpoint modulatory agent to the subject. Further provided herein are methods, wherein the dendritic cells are cultured on a hard surface. Further provided herein are methods, wherein the Arbovirus is Dengue virus. Further provided herein are methods, wherein the Dengue virus is a serotype of at least one of DENV-1, DENV-2, DENV-3, DENV-4, or DENV-5. Further provided herein are methods, wherein the Dengue virus is DENV-2 strain #1710. Further provided herein are methods, wherein the Alphavirus is Chikungunya virus. Further provided herein are methods, wherein the dendritic cells are autologous or allogeneic. Further provided herein are methods, wherein the cancer cells are from the subject. Further provided herein are methods, wherein the primed dendritic cells produce at least about 6.5 ng/mL IL-12p70. Further provided herein are methods, wherein the immune checkpoint modulatory agent modulates the expression or activity of at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. Further provided herein are methods, wherein immune checkpoint modulatory agent is an immune checkpoint inhibitor that targets at least one of A2aR, CD276, B7H4, BTLA, CTLA-4, IDO1, IDO2, KIR, LAG3, PD-1, PDL-1, PDL-2, PS, TIM3, or VISTA. Further provided herein are methods, wherein an immune checkpoint modulatory agent activates at least one of CD122, CD137 (4-1BB), CD137L, CD27, CD28, CD40, CD70, CD80 (B7.1), CD86 (B7.2), GITR, GITRL, ICOS, ICOSL (B7H2), OX-40, or OX-40L. Further provided herein are methods, wherein the immune checkpoint modulatory agent is at least one of an antibody, a nucleic acid encoding an antibody, an antigen binding fragment, a RNA interfering agent, a peptide, a peptidomimetic, a small molecule, or an aptamer. Further provided herein are methods, wherein said RNA interfering agent is a small interfering RNA (siRNA), short hairpin RNA (shRNA), or a microRNA (miRNA). Further provided herein are methods, wherein said immune checkpoint modulatory agent is administered in a pharmaceutically acceptable formulation.

Provided herein are methods for treatment or reduction of cancer in a subject in need thereof, comprising: obtaining dendritic cells from a subject; contacting the dendritic cells with the lysate, thereby generating primed dendritic cells; administering the primed DCs to the subject; administering a strain of an Arbovirus or a strain of an Alphavirus to the subject in need thereof, and administering an immune checkpoint modulatory agent. Further provided herein are methods wherein the hard surface is a hard plastic surface. Further provided herein are methods, wherein the hard plastic surface is a polystyrene surface. Further provided herein are methods, wherein the Arbovirus is Dengue virus. Further provided herein are methods, wherein the Dengue virus is a serotype of at least one of DENV-1, DENV-2, DENV-3, DENV-4, or DENV-5. Further provided herein are methods, wherein the Dengue virus is DENV-2 strain #1710. Further provided herein are methods, wherein the Alphavirus is Chikungunya virus. Further provided herein are methods, wherein the cancer cells are from the subject. Further provided herein are methods, wherein the primed dendritic cells produce at least about 6.5 ng/mL IL-12p70. Further provided herein are methods, wherein the immune checkpoint modulatory agent modulates the expression or activity of at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. Further provided herein are methods, wherein immune checkpoint modulatory agent is an immune checkpoint inhibitor that targets at least one of A2aR, CD276, B7H4, BTLA, CTLA-4, IDO1, IDO2, KIR, LAG3, PD-1, PDL-1, PDL-2, PS, TIM3, or VISTA. Further provided herein are methods, wherein wherein an immune checkpoint modulatory agent activates at least one of CD122, CD137 (4-1BB), CD137L, CD27, CD28, CD40, CD70, CD80 (B7.1), CD86 (B7.2), GITR, GITRL, ICOS, ICOSL (B7H2), OX-40, or OX-40L. Further provided herein are methods, wherein the immune checkpoint modulatory agent is at least one of an antibody, a nucleic acid encoding an antibody, an antigen binding fragment, a RNA interfering agent, a peptide, a peptidomimetic, a small molecule, or an aptamer. Further provided herein are methods, wherein said RNA interfering agent is a small interfering RNA (siRNA), short hairpin RNA (shRNA), or a microRNA (miRNA). Further provided herein are methods, wherein said immune checkpoint modulatory agent is administered in a pharmaceutically acceptable formulation.

Provided herein are methods for clearing cancer cells in a subject, comprising: administering a strain of an Arbovirus or a strain of an Alphavirus to a subject in need thereof; administering an immune checkpoint modulatory agent; priming dendritic cells, wherein priming comprises: exposing the dendritic cells to a lysate to produce primed dendritic cells, wherein the lysate comprises a plurality of cancer cells, each cancer cell comprising an antigen present on the surface of said cancer cell; and administering the primed dendritic cells to the subject, wherein the administration provides for clearance of 33% or more of a cancer cell population in the subject. Further provided herein are methods, wherein the administration provides for clearance of 33% of the cancer cell population in the subject. Further provided herein are methods, wherein the Arbovirus is Dengue virus. Further provided herein are methods, wherein the Dengue virus is a serotype of at least one of DENV-1, DENV-2, DENV-3, DENV-4, or DENV-5. Further provided herein are methods, wherein the Dengue virus is DENV-2 strain #1710. Further provided herein are methods, wherein the Alphavirus is Chikungunya virus. Further provided herein are methods, further comprising intravenously administering the Dengue virus serotype 2 and intravenously administering the population of primed dendritic cells. Further provided herein are methods, wherein the plurality of cancer cells are from the subject. Further provided herein are methods, wherein the immune checkpoint modulatory agent is at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. Further provided herein are methods, wherein immune checkpoint modulatory agent is an immune checkpoint inhibitor that targets at least one of A2aR, CD276, B7H4, BTLA, CTLA-4, IDO1, IDO2, KIR, LAG3, PD-1, PDL-1, PDL-2, PS, TIM3, or VISTA. Further provided herein are methods, wherein an immune checkpoint modulatory agent activates at least one of CD122, CD137 (4-1BB), CD137L, CD27, CD28, CD40, CD70, CD80 (B7.1), CD86 (B7.2), GITR, GITRL, ICOS, ICOSL (B7H2), OX-40, or OX-40L. Further provided herein are methods, wherein the immune checkpoint modulatory agent is at least one of an antibody, a nucleic acid encoding an antibody, an antigen binding fragment, a RNA interfering agent, a peptide, a peptidomimetic, a small molecule, or an aptamer. Further provided herein are methods, wherein said RNA interfering agent is a small interfering RNA (siRNA), short hairpin RNA (shRNA), or a microRNA (miRNA). Further provided herein are methods, wherein said immune checkpoint modulatory agent is administered in a pharmaceutically acceptable formulation.

DETAILED DESCRIPTION

Figure 1:
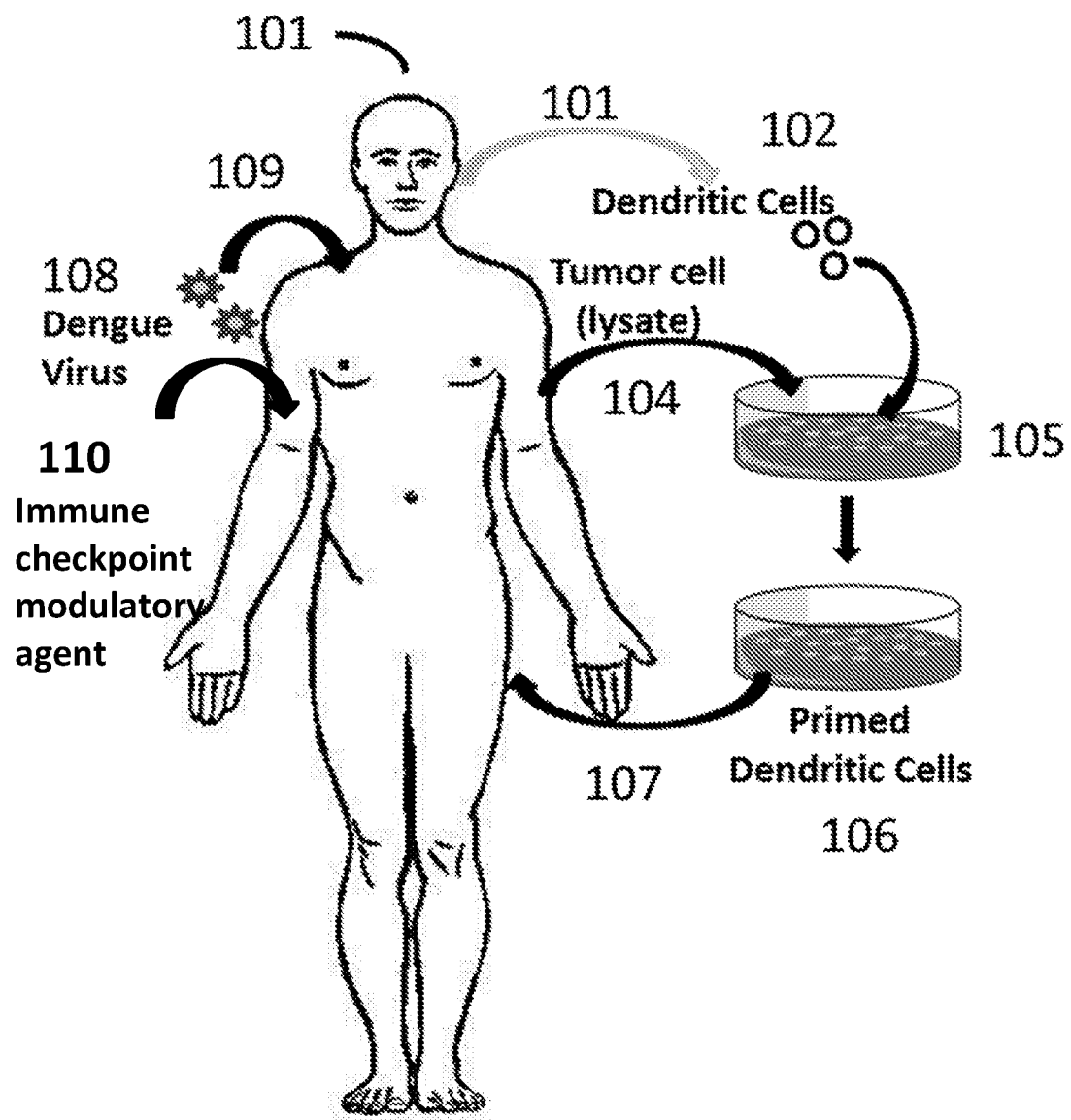
FIG. 1 depicts an exemplary method of treatment with Dengue virus, an immune checkpoint modulatory agent, and primed dendritic cells.
Figure 2:
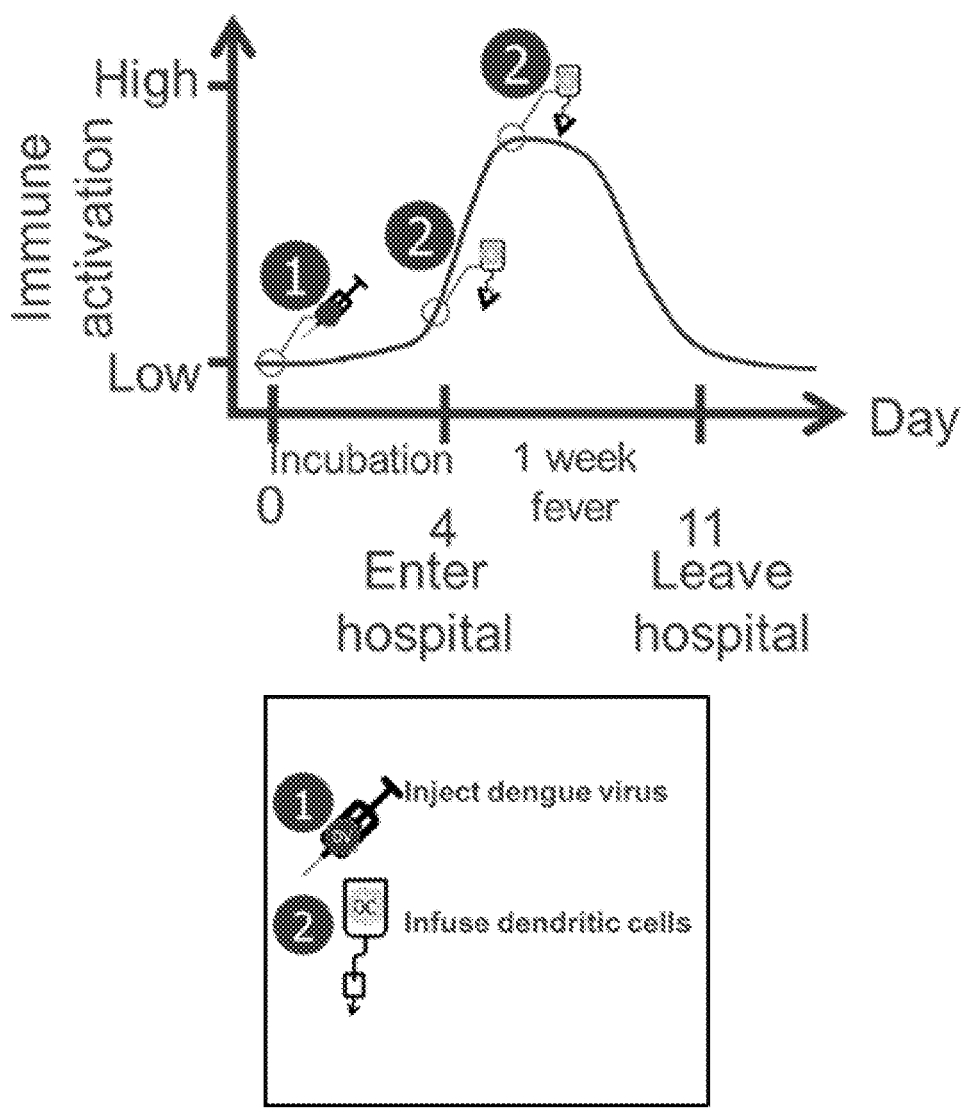
FIG. 2 depicts an exemplary treatment timeline with Dengue virus and primed dendritic cells.
Figure 3A:
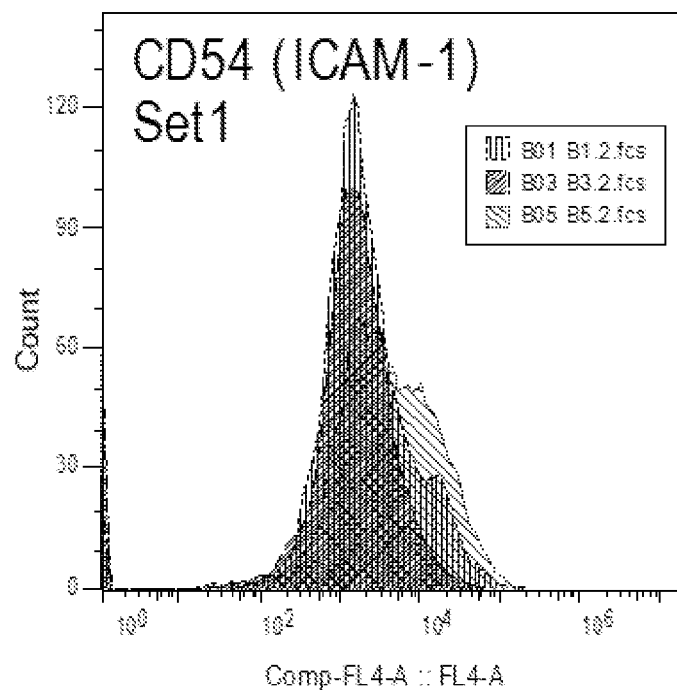
FIG. 3A depicts a histogram of ICAM-1 expression in A549 lung cancer cells with and without Dengue virus supernatant. Light orange represents addition of Dengue virus supernatant. Red represents Dengue virus supernatant mock (PBMC with no virus, but with contact-activation of monocyte cells). Blue represents control.
Figure 3B:
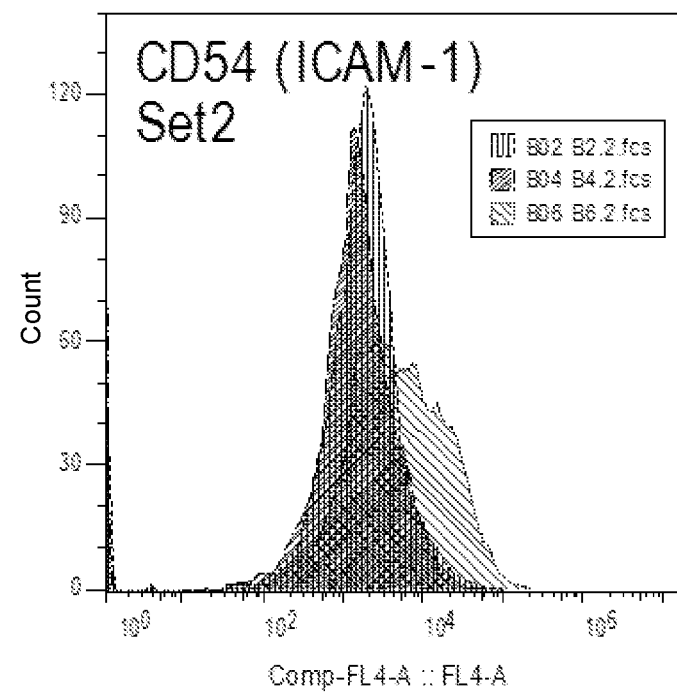
FIG. 3B depicts a second run of a histogram of ICAM-1 expression in A549 lung cancer cells with and without Dengue virus supernatant. Light orange represents addition of Dengue virus supernatant. Red represents Dengue virus supernatant mock (PBMC with no virus, but with contact-activation of monocyte cells). Blue represents control.
Figure 4A:
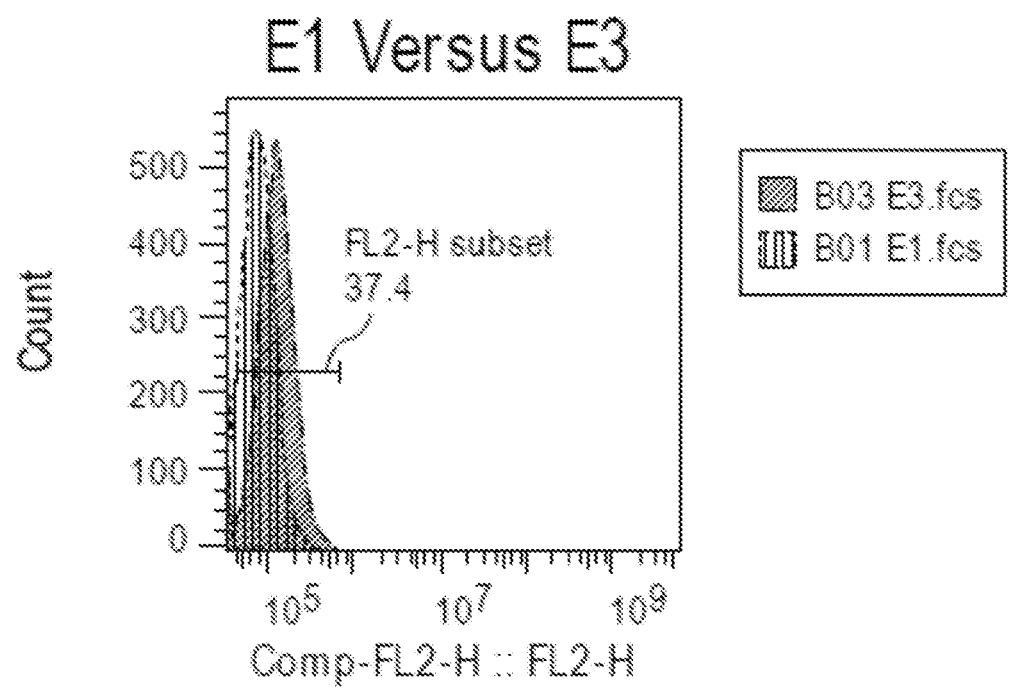
FIG. 4A depicts surface expression of MHC-1 on 624.28 alone (E1) or 624.28 treated with Dengue Virus supernatant (E3) at MOI of 2. The histogram of HLA A/B/C expression after application of Dengue virus supernatant to 624.28 melanoma cells shows up-regulation of Class I MHC along both X and Y axes. The blue histogram up-regulation represents Dengue virus supernatant at 30 uL. The red histogram up-regulation represents control.
Figure 4B:
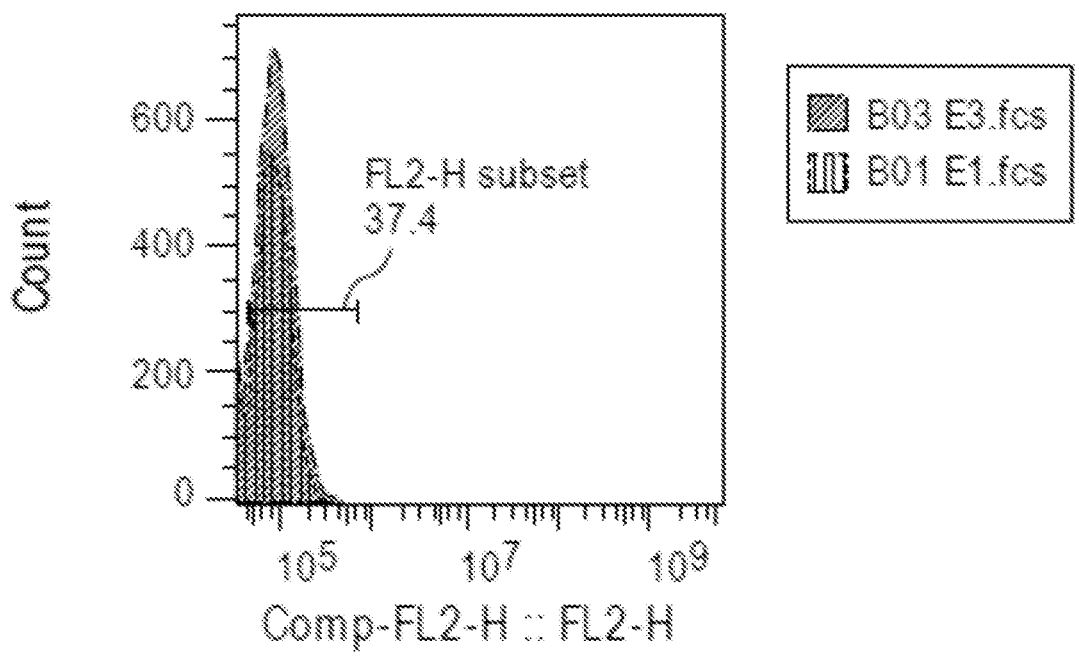
FIG. 4B depicts a high HLA-expression tumor cell line, FEMX, as a control group. As expected, the FEMX control cells already showed high HLA expression; Dengue virus supernatants raised HLA expression levels 1.32-fold over controls. The blue flow area represents Dengue virus supernatant at 30 uL. The red flow area represents control.
Figure 5A:
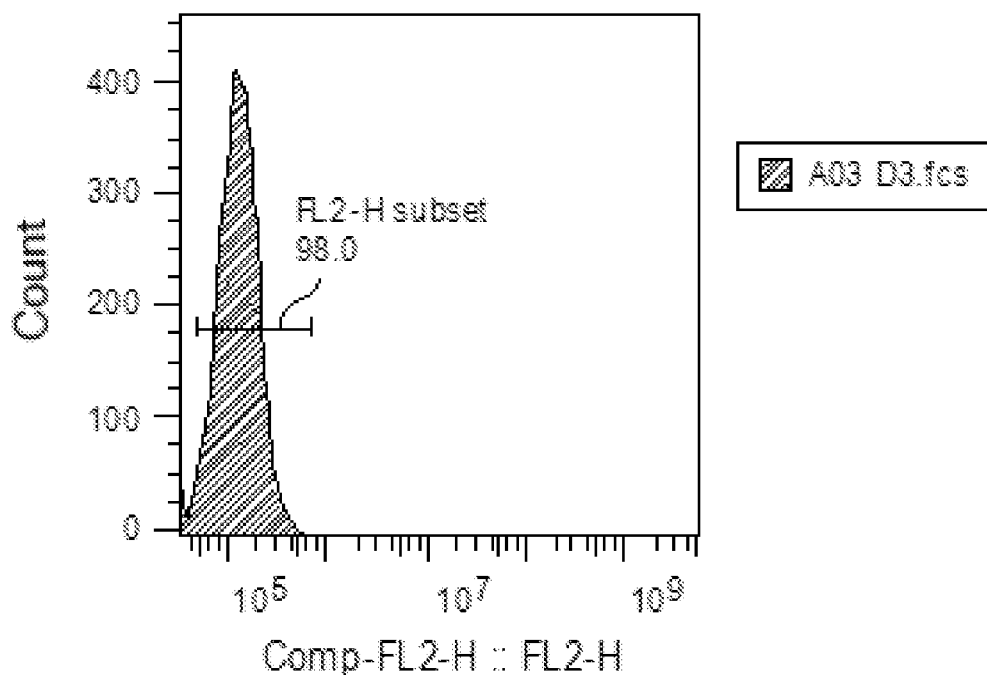
FIG. 5A shows a FACs plot of HLA-A, B, C expression on FEMX.
Figure 5B:
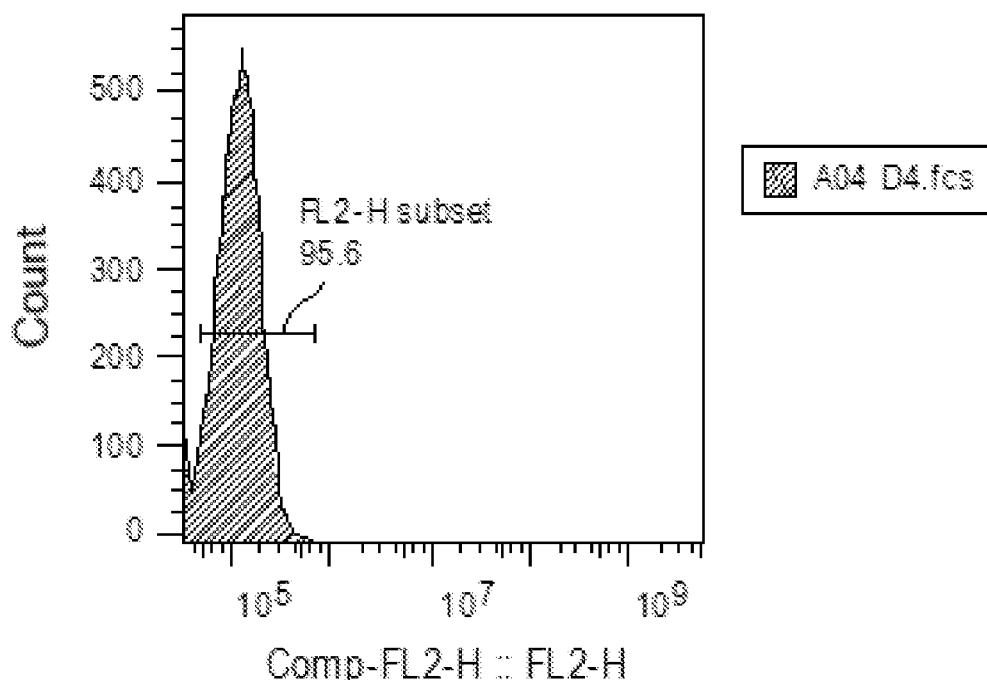
FIG. 5B shows a duplicate FACs plot of HLA-A, B, C expression on FEMX.
Figure 5C:
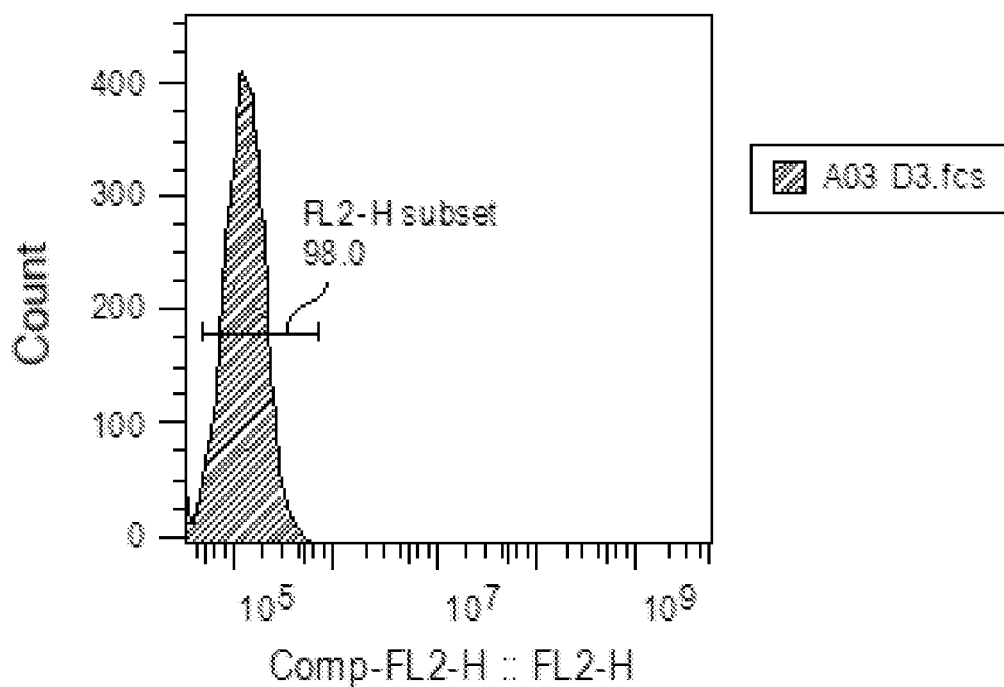
FIG. 5C shows a FACs plot of HLA-A, B, C expression on FEMX to which Dengue virus has been added at MOI of 2.
Figure 5D:
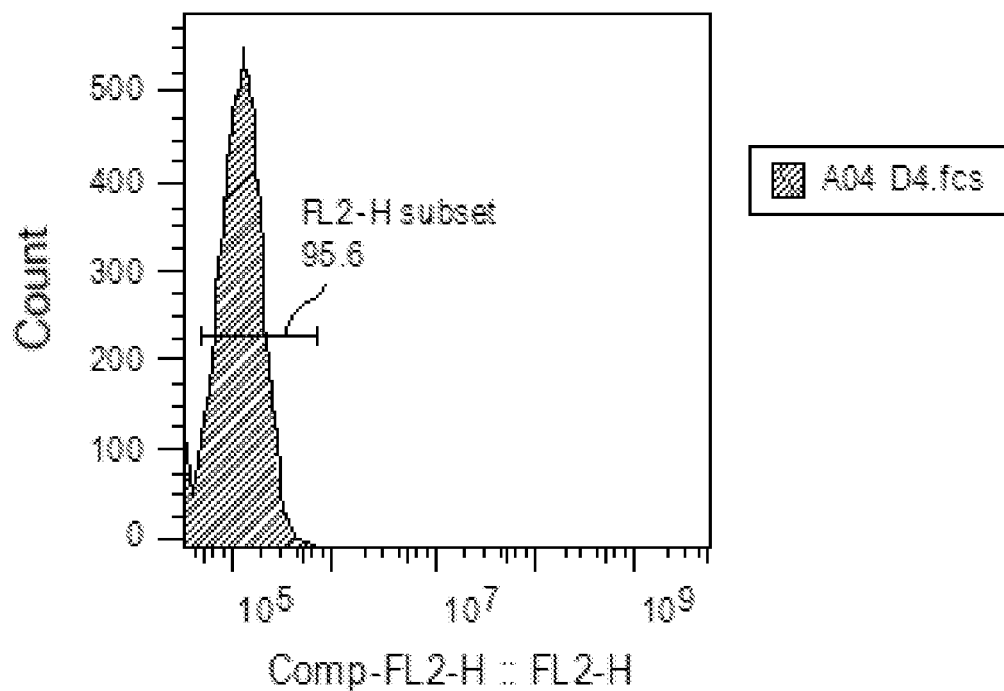
FIG. 5D shows a duplicate FACs plot of HLA-A, B, C expression on FEMX to which Dengue virus has been added at MOI of 2.
Figure 5E:
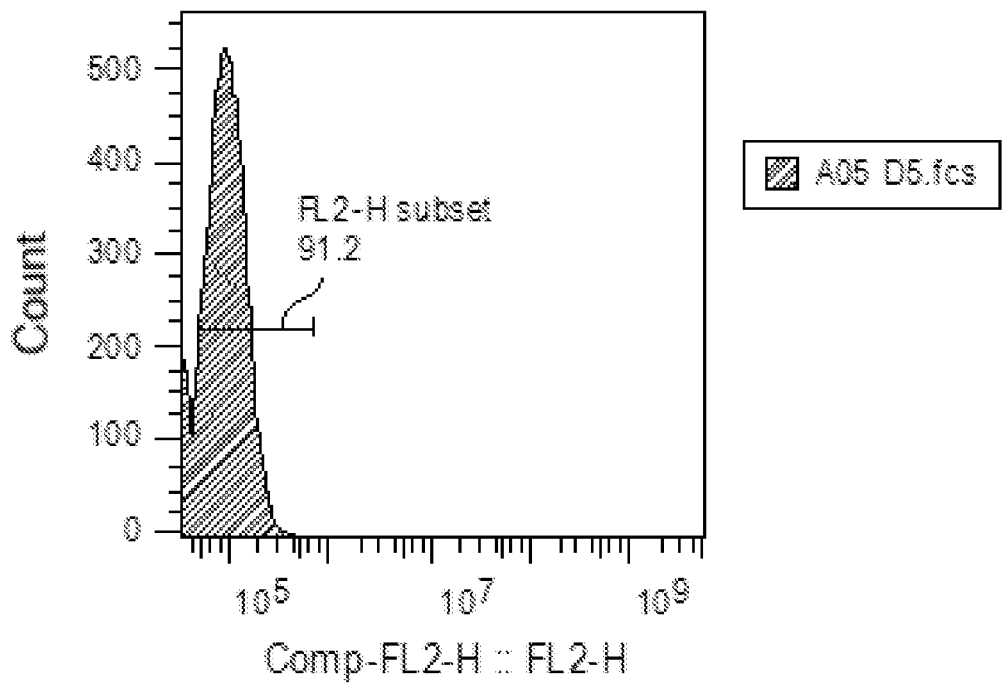
FIG. 5E shows a FACs plot of HLA-A, B, C expression on FEMX to which no Dengue virus has been added, mock.
Figure 5F:
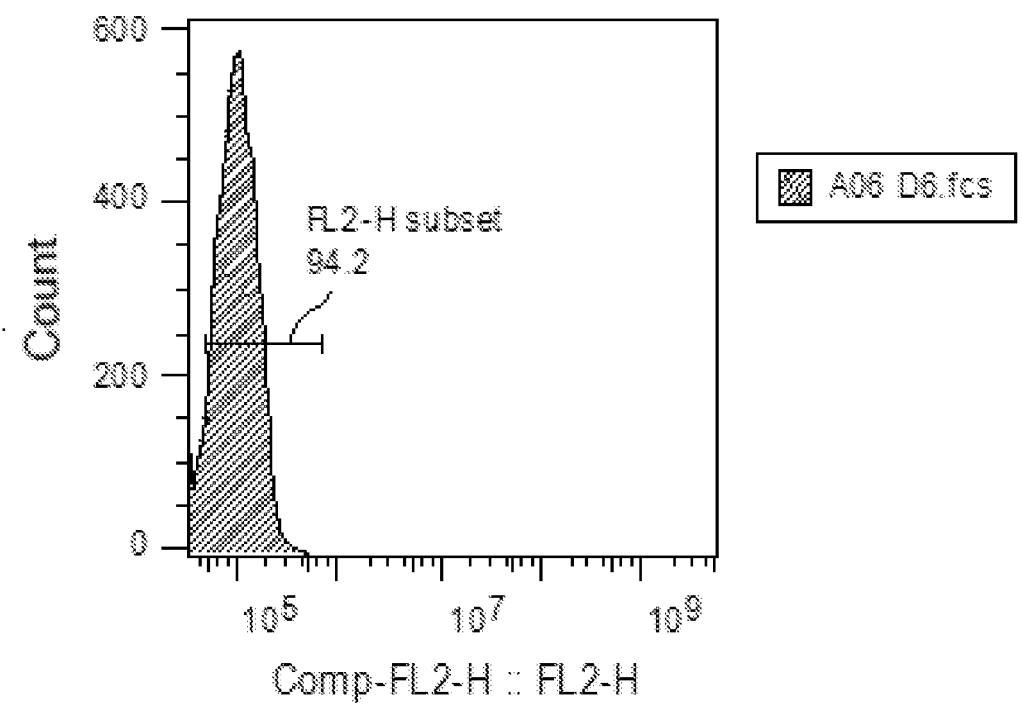
FIG. 5F shows a duplicate FACs plot of HLA-A, B, C expression on FEMX to which no Dengue virus has been added, mock.
Figure 5G:
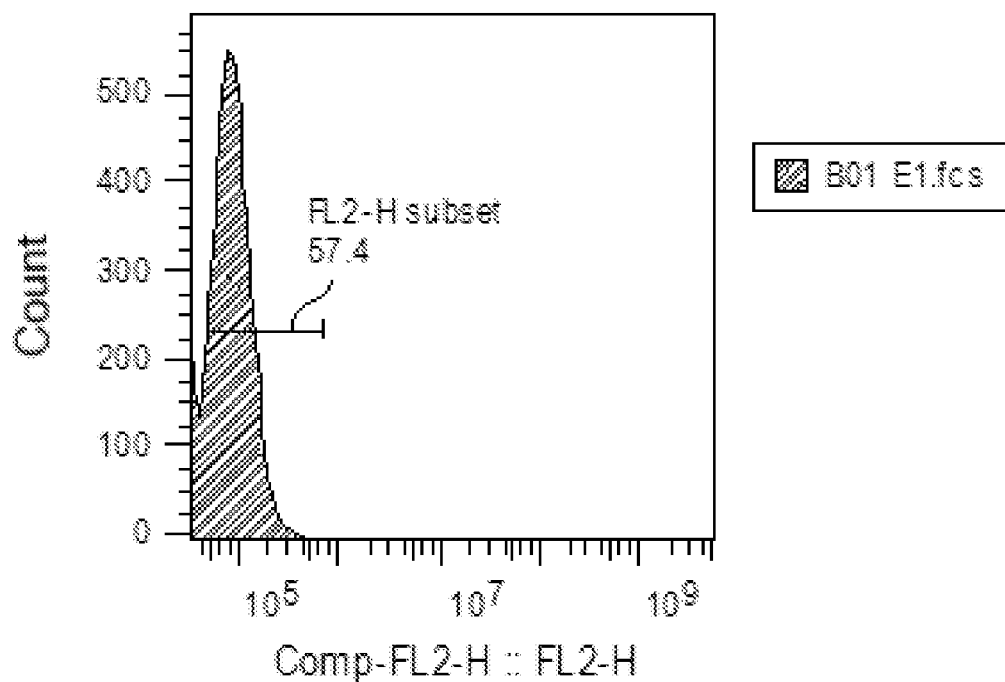
FIG. 5G shows a FACs plot of HLA-A, B, C expression on 624.28.
Figure 5H:
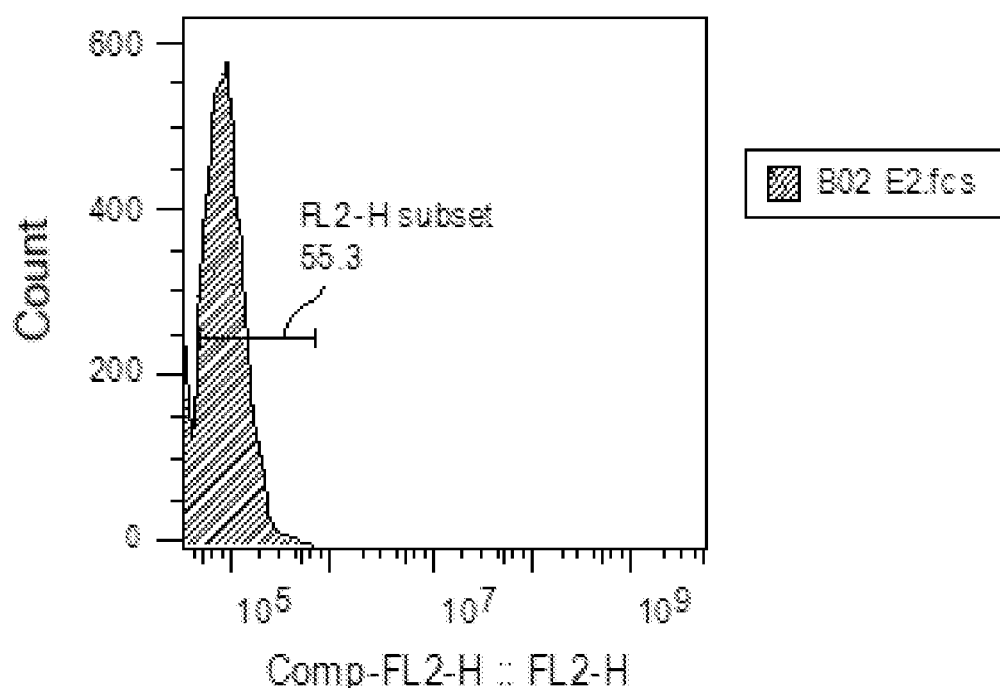
FIG. 5H shows a duplicate FACs plot of HLA-A, B, C expression on 624.28.
Figure 5I:
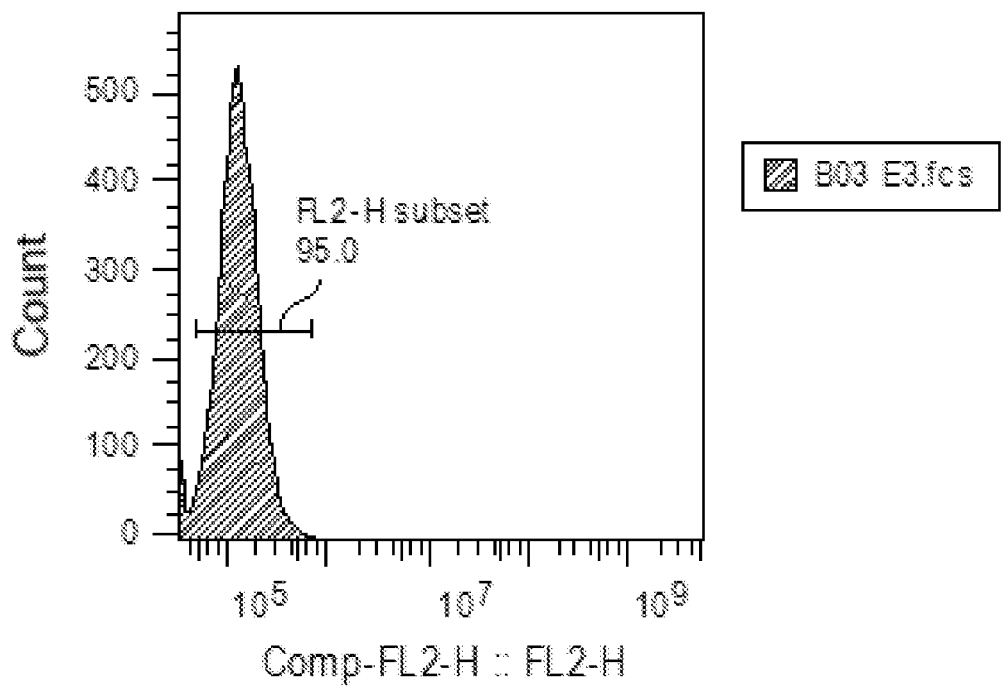
FIG. 5I shows a FACs plot of HLA-A, B, C expression on 624.28 to which Dengue virus has been added at MOI of 2.
Figure 5J:
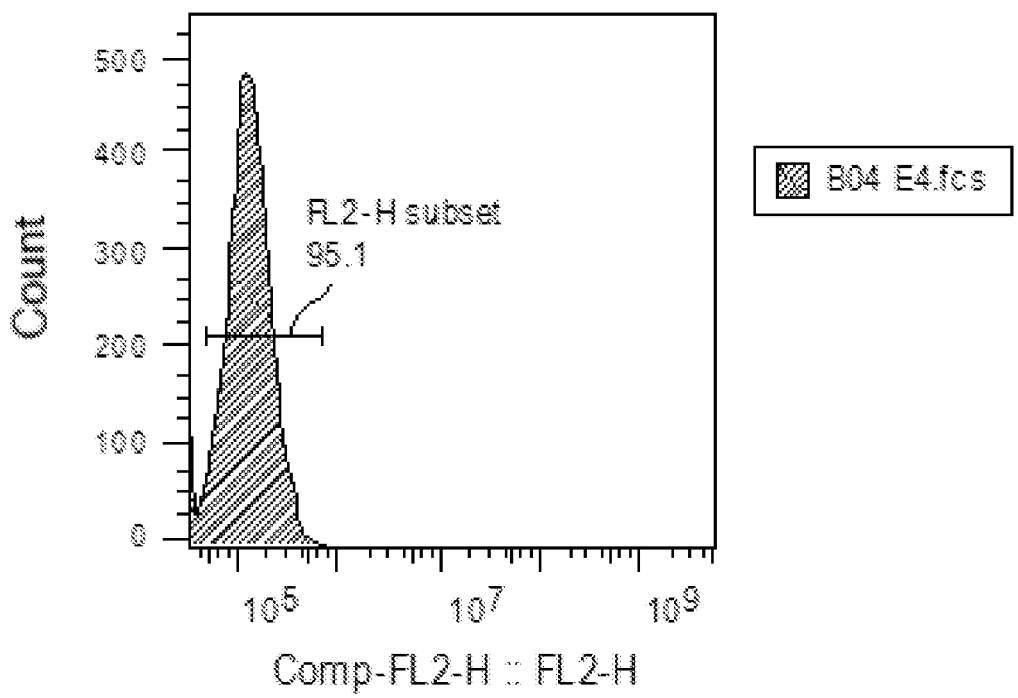
FIG. 5J shows a duplicate FACs plot of HLA-A, B, C expression on 624.28 to which Dengue virus has been added at MOI of 2.
Figure 5K:
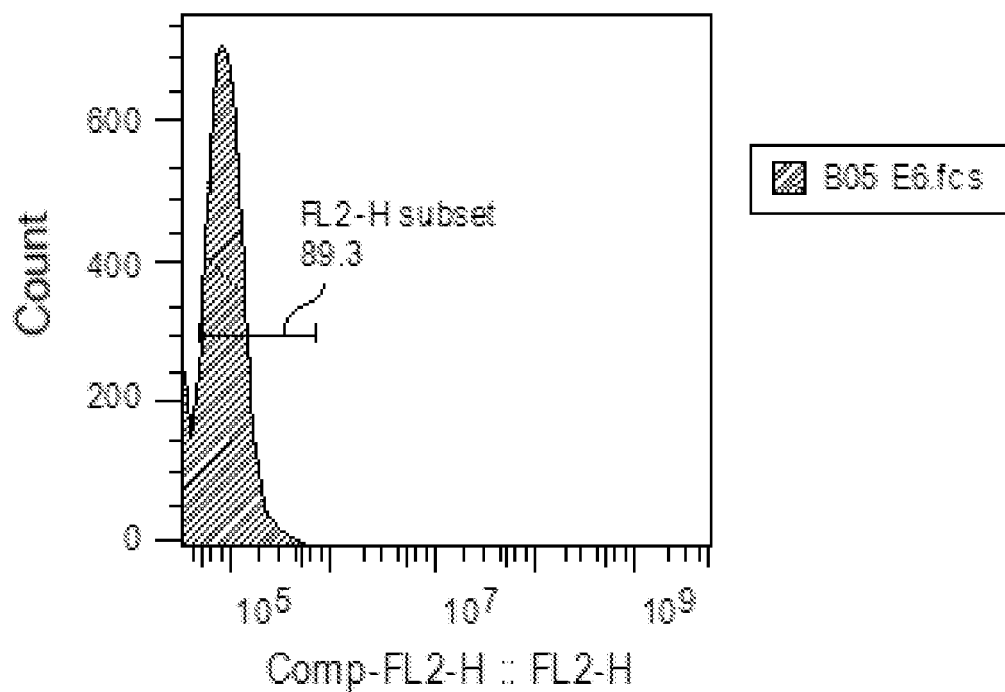
FIG. 5K shows a FACs plot of HLA-A, B, C expression of 624.28 to which no Dengue virus has been added, mock.
Figure 5L:
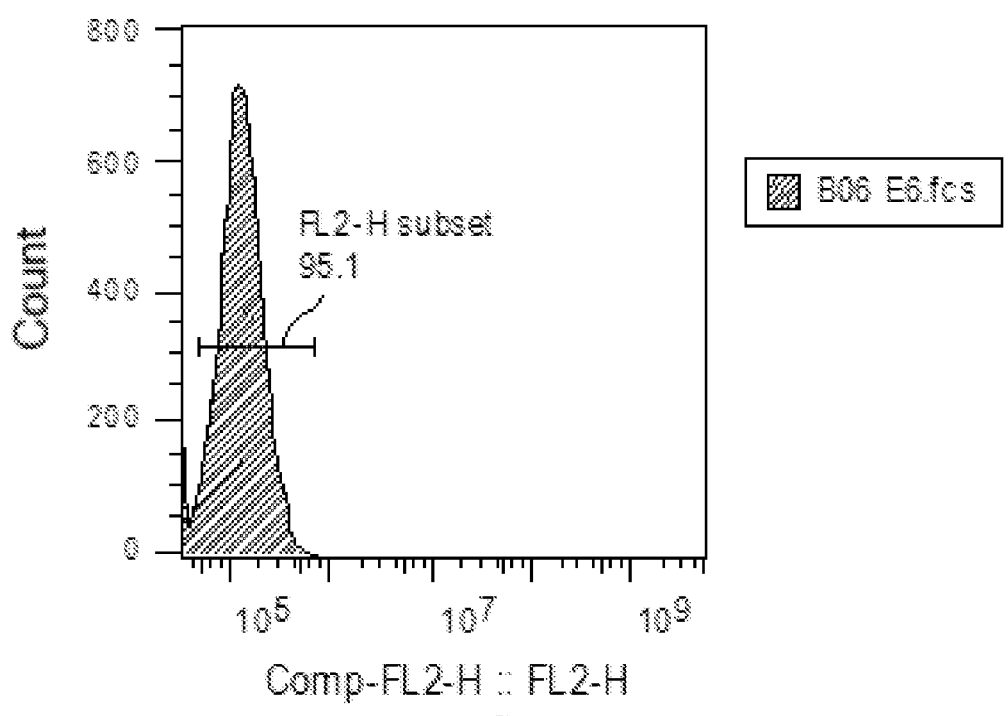
FIG. 5L shows a duplicate FACs plot of HLA-A, B, C expression of 624.28 to which no Dengue virus has been added, mock.

Provided herein are methods and compositions for combination therapy for treating cancer comprising administering an immune checkpoint modulatory agent and a strain of an Arbovirus or a strain of an Alphavirus to a subject. A method can also comprise priming dendritic cells (DCs) to target cancer antigens. Further provided herein can be a combination therapy for treating cancer comprising administering a strain of an Arbovirus or a strain of an Alphavirus. A combination therapy may be used to overcome tumor immune evasion mechanisms and deplete tumor cells in the subject.

Provided herein are methods for preparation of primed dendritic cells (DCs). Further provided herein are methods for exposing the primed dendritic cells to antigens associated with a disease state, e.g., tumor antigens, resulting primed dendritic cells capable of inducing specific and robust responses from cytotoxic T lymphocyte (CTL) toward cancer cells. Further provided herein are methods for administering such DCs into a subject for treatment of a disorder linked to the disease state. In some instances, the disorder is cancer. In some instances, the disorder is an autoimmune disorder, e.g., rheumatoid arthritis and multiple sclerosis. In some instances, the disorder is a human immunodeficiency virus (HIV) infection or an acquired immunodeficiency syndrome. In some instances, a strain of an Arbovirus or a strain of an Alphavirus is a Dengue virus or a Chikungunya virus. In some instances, the subject is administered a Dengue Virus prior to administration of the primed DCs. In some instances, the subject is administered a Chikungunya virus prior to administration of the primed DCs. In some cases, an immune modulatory agent is administered prior, during, or following administration of a Dengue virus. In some cases, an immune modulatory agent is administered prior, during, or following administration of a Chikungunya virus Priming the dendritic cells generally involves contacting the dendritic cells with one or more tumor antigens that are present on target cancer cells. In some cases, the dendritic cells are primed with the tumor antigen alone, the tumor antigen having been synthesized, isolated or purified. Alternatively or additionally, the dendritic cells are primed with a tumor cell lysate, wherein the tumor cell lysate contains the tumor antigen. In some cases, the dendritic cell is primed with a whole cancer cell expressing the tumor antigen. The dendritic cell is then administered to the subject, where it will present the tumor antigen to the CTL, and thus, tailor the CTL for recognition and destruction of target cancer cells.

Provided herein are methods which limit dendritic cells exposure to polymers contained in plastic container material. For example, in the case of soft plastic bags, polymers may leach into the media solution and impact DC activity. Instead, dendritic cells may be cultured, stored and shipped in and on a hard container, such as a polystyrene tissue culture plate. This avoids a reduction in dendritic cell immunostimulatory activity that can be caused by exposure to polymers contained in soft plastic bags. For example, these polymers can reduce the amount of IL-12 produced by the dendritic cells, thereby reducing their capacity to induce a robust CTL response. Examples provided herein demonstrate that primed dendritic cells generated by the methods disclosed herein are capable of secreting at least about 6.5 pg/mL of IL-12p70, whereas dendritic cells produced by standard methods typically only produce 4-6 pg/mL of IL-12p70.

In some cases, it is desirable or advantageous to prime the dendritic cells with a tumor lysate. Notably, the methods disclosed herein utilize a gentle cell lysis protocol that preserves the integrity of the tumor antigen. This gentle lysis may be achieved by exposing the tumor or cancer cells to a calcium or sodium hypochlorite solution for no more than about 30-60 minutes. Similarly, any tumor cells used to prime dendritic cells are disassociated gently, for instance, by a Miltenyi GentleMACS system, or the like.

Primed dendritic cells prepared by the methods disclosed herein may be administered to the subject along with an agent that will boost the subject's immune system. For example, the primed dendritic cells may be administered to the subject after infecting the subject with a virus. By way of example, the methods and examples disclosed herein use a Dengue virus, particularly Dengue virus serotype 2 strain #1710, which is relatively safe (e.g., no known occurrence of lethality or serious adverse events). This virus provides for the activation of a suppressed immune system (e.g., by producing a TH1 polarity shift), and improving targeting specificity, thereby providing higher efficacy and safety relative to current cellular therapies. The combination of primed dendritic cells with a viral infection provides for an effective treatment with minimal administration, possibly as few as one time, which avoids the challenge of subject adherence to therapy. The primed dendritic cells may be autologous, meaning derived from a subject's own cells, or allogenic, derived from another subject with a similar tissue type.

Immune Checkpoints

Provided herein are methods for combination therapy. In some instances, the combination therapy comprises administration of an immune checkpoint modulatory agent with an Arbovirus. In some cases, the combination therapy comprises administration of an immune checkpoint modulatory agent with an Alphavirus. In some cases, the Arbovirus is Dengue virus (DV). In some instances, the Alphavirus is Chikungunya virus (CV).

In some instances, an immune checkpoint modulatory agent is administered prior to administration of DV. In some cases, an immune checkpoint modulatory agent is co-administered with DV. In some instances, an immune checkpoint modulatory agent is administered following administration of DV. In some cases, an immune checkpoint modulatory agent is at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. The immune checkpoint modulatory agent can be at least one of B7H3, CD137 (41BB), CD27, CTLA4, GITR, KIR, LAG3, PD-1, PDL-1 (B7H1, CD274), or PS. Exemplary amino acid sequences for immune checkpoint modulatory agents, without limitation, are provided in Table 1. Amino acid sequences for immune checkpoint modulatory agents can be at least about 40%, about 45%, about 50%, about 55%, about 60%, about 65%, about 70%, about 75%, about 80%, about 85%, about 90%, about 95%, or about 100% similar in homology to a sequence of Table 1.

In some instances, an immune checkpoint modulatory agent is administered prior to administration of CV. In some cases, an immune checkpoint modulatory agent is co-administered with CV. In some instances, an immune checkpoint modulatory agent is administered following administration of CV. In some cases, an immune checkpoint modulatory agent is at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA. The immune checkpoint modulatory agent can be at least one of B7H3, 41BB, CD27, CTLA4, GITR, KIR, LAG3, PD-1, PDL-1, or PS. Exemplary amino acid sequences for immune checkpoint modulatory agents, without limitation, are provided in Table 1. In some cases, from about 50%, 60%, 70%, 80%, 90%, 95%, 96%, 97%, 98%, 99% or up to about 100% homology to any one of SEQ ID NO: 1 to SEQ ID NO: 9 can be utilized herein.

Table 1. Amino Acid Sequence of Immune Checkpoint Modulatory Agents

TABLE 1

Amino Acid Sequence of Immune Checkpoint Modulatory Agents

| Target | GenBank Accession Number | SEQ ID NO: | Amino Acid Sequence |
|---|---|---|---|
| PD-1 | NP_005009 | 1 | MQIPQAPWPVVWAVLQLGWRPGWFLDSPDRPWN PPTFSPALLVVTEGDNATFTCSFSNTSESFVLNWYR MSPSNQTDKLAAFPEDRSQPGQDCRFRVTQLPNGR DFHMSVVRARRNDSGTYLCGAISLAPKAQIKESLR AELRVTERRAEVPTAHPSPSPRPAGQFQTLVVGVV GGLLGSLVLLVWVLAVICSRAARGTIGARRTGQPL KEDPSAVPVFSVDYGELDFQWREKTPEPPVPCVPE QTEYATIVFPSGMGTSSPARRGSADGPRSAQPLRPE DGHCSWPL |
| PDL-1 | AAI13735.1 | 2 | MRIFAVFIFMTYWHLLNAFTVTVPKDLYVVEYGSN MTIECKFPVEKQLDLAALIVYWEMEDKNIIQFVHGE EDLKVQHSSYRQRARLLKDQLSLGNAALQITDVKL QDAGVYRCMISYGGADYKRITVKVNAPYNKINQRI LVVDPVTSEHELTCQAEGYPKAEVIWTSSDHQVLS GKTTTTNSKREEKLFNVTSTLRINTTTNEIFYCTFRR LDPEENHTAELVIPELPLAHPPNERTHLVILGAILLC LGVALTFIFRLRKGRMMDVKKCGIQDTNSKKQSDT HLEET |
| CTLA-4 | AAH74893 | 3 | MACLGFQRHKAQLNLATRTWPCTLLFFLLFIPVFCK AMHVAQPAVVLASSRGIASFVCEYASPGKATEVRV TVLRQADSQVTEVCAATYMMGNELTFLDDSICTGT SSGNQVNLTIQGLRAMDTGLYICKVELMYPPPYYL GIGNGTQIYVIDPEPCPDSDFLLWILAAVSSGLFFYS FLLTAVSLSKMLKKRSPLTTGVYVKMPPTEPECEK QFQPYFIPIN |
| LAG3 | AAH52589 | 4 | MWEAQFLGLLFLQPLWVAPVKPLQPGAEVPVVWA QEGAPAQLPCSPTIPLQDLSLLRRAGVTWQHQPDSG PPAAAPGHPLAPGPHPAAPSSWGPRPRRYTVLSVGP GGLRSGRLPLQPRVQLDERGRQRGDFSLWLRPARR ADAGEYRAAVHLRDRALSCRLRLRLGQASMTASPP GSLRASDWVILNCSFSRPDRPASVHWFRNRGQGRV PVRESPHHHLAESFLFLPQVSPMDSGPWGCILTYRD GFNVSIMYNLTVLGLEPPTPLTVYAGAGSRVGLPCR LPAGVGTRSFLTAKWTPPGGGPDLLVTGDNGDFTL RLEDVSQAQAGTYTCHIHLQEQQLNATVTLAIITGQ PQVGKE |
| B7H3 | Q5ZPR3 | 5 | MLRRRGSPGMGVHVGAALGALWFCLTGALEVQVP EDPVVALVGTDATLCCSFSPEPGFSLAQLNLIWQLT DTKQLVHSFAEGQDQGSAYANRTALFPDLLAQGN ASLRLQRVRVADEGSFTCFVSIRDFGSAAVSLQVAA PYSKPSMTLEPNKDLRPGDTVTITCSSYQGYPEAEV FWQDGQGVPLTGNVTTSQMANEQGLFDVHSILRV VLGANGTYSCLVRNPVLQQDAHSSVTITPQRSPTG AVEVQVPEDPVVALVGTDATLRCSFSPEPGFSLAQL NLIWQLTDTKQLVHSFTEGRDQGSAYANRTALFPD LLAQGNASLRLQRVRVADEGSFTCFVSIRDFGSAA VSLQVAAPYSKPSMTLEPNKDLRPGDTVTITCSSYR GYPEAEVFWQDGQGVPLTGNVTTSQMANEQGLFD VHSVLRVVLGANGTYSCLVRNPVLQQDAHGSVTIT GQPMTFPPEALWVTVGLSVCLIALLVALAFVCWRK IKQSCEEENAGAEDQDGEGEGSKTALQPLKHSDSK EDDGQEIA |
| KIR | CDM87328.1 | 6 | MSLMVVSMACVGFFLLQGAWPHEGVHRKPSLLAH PGPLVKSEETVILQCWSDVRFEHFLLHREGKYKDTL HLIGEHHDGVSKANFSIGPMMQDLAGTYRCYGSVT HSPYQLSAPSDPLDIVITGLYEKPSLSAQPGPTVLAG ESVTLSCSSRSSYDMYHLSREGEAHERRFSAGPKVN |

TABLE 1-continued

Amino Acid Sequence of Immune Checkpoint Modulatory Agents

| Target | GenBank Accession Number | SEQ ID NO: | Amino Acid Sequence |
|---|---|---|---|
| | | | GTFQADFPLGPATHGGTYRCFGSFRDSPYEWSNSS DPLLVSVTGNPSNSWPSPTEPSSKTGNPRHLHVLIG TSVVIILFILLLFFLLHRWCCNKKNAVVMDQEPAGN RTVNREDSDEQDPQEVTYAQLNHCVFTQRKITHPS QRPKTPPTDIIVYTELPNAEP |
| CD137 | AAH06196.1 | 7 | MGNSCYNIVATLLLVLNFERTRSLQDPCSNCPAGTF CDNNRNQICSPCPPNSFSSAGGQRTCDICRQCKGVF RTRKECSSTSNAECDCTPGFHCLGAGCSMCEQDCK QGQELTKKGCKDCCFGTFNDQKRGICRPWTNCSLD GKSVLVNGTKERDVVCGPSPADLSPGASSVTPPAP AREPGHSPQIISFFLALTSTALLFLLFFLTLRFSVVKR GRKKLLYIFKQPFMRPVQTTQEEDGCSCRFPEEEEG GCEL |
| CD27 | AAH12160.1 | 8 | MARPHPWWLCVLGTLVGLSATPAPKSCPERHYWA QGKLCCQMCEPGTFLVKDCDQHRKAAQCDPCIPG VSFSPDHHTRPHCESCRHCNSGLLVRNCTITANAEC ACRNGWQCRDKECTECDPLPNPSLTARSSQALSPH PQPTHLPYVSEMLEARTAGHMQTLADFRQLPARTL STHWPPQRSLCSSDFIRILVIFSGMFLVFTLAGALFL HQRRKYRSNKGESPVEPAEPCRYSCPREEEGSTIPIQ EDYRKPEPACSP |
| GITR | AAI52382.1 | 9 | MAQHGAMGAFRALCGLALLCALSLGQRPTGGPGC GPGRLLLGTGTDARCCRVHTTRCCRDYPGEECCSE WDCMCVQPEFHCGDPCCTTCRHHPCPPGQGVQSQ GKFSFGFQCIDCASGTFSGGHEGHCKPWTDCTQFG FLTVFPGNKTHNAVCVPGSPPAEPLGWLTVVLLAV AACVLLLTSAQLGLHIWQLRSQCMWPRETQLLLEV PPSTEDARSCQFPEEERGERSAEEKGRLGDLWV |

Immune Modulatory Agent Inhibitors

In some instances, an immune checkpoint modulatory agent for administration in a method described herein is an inhibitor that targets at least one of A2aR, B7H3, B7H4, BTLA, CTLA-4, IDO1, IDO2, KIR, LAG3, PD-1, PDL-1, PDL-2, PS, TIM3, or VISTA. In some cases, the inhibitor targets A2aR. In some cases, the inhibitor targets B7H3. In some cases, the inhibitor targets B7H4. In some cases, the inhibitor targets BTLA. In some instances, the inhibitor targets CTLA4. In some cases, the inhibitor targets IDO1. In some cases, the inhibitor targets IDO2. In some instances, the inhibitor is directed to KIR. In some instances, the inhibitor is directed to LAG3. In some instances, the inhibitor is directed to PD-1. In some cases, the inhibitor is directed to PDL-1. In some cases, the inhibitor targets PDL-2. In some cases, the inhibitor is directed to PS. In some instances, the inhibitor targets TIM3. In some cases, the inhibitor targets VISTA. In some instances, the immune checkpoint modulatory agent binds directly to a target described herein. In some instances, the immune checkpoint modulatory agent binds indirectly to a target described herein.

In some cases, the immune checkpoint inhibitor is an antibody against at least one of B7H3, CTLA4, KIR, LAG3, PD-1, PDL-1, or PS. In some instances, the antibody is at least one of monoclonal antibodies, synthetic antibodies, polyclonal antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv) or epitope-binding fragments thereof. In some cases, the antibodies are immunoglobulin molecules or immunologically active portions of immunoglobulin molecules. In some instances, the antibodies are animal in origin including birds and mammals. In some cases, the antibodies are human or humanized monoclonal antibodies.

In some cases, the antibody against B7H3 is Enoblituzumab (e.g., MGA271). In some instances, the antibody against CTLA-4 is selected from Ipilimumab (e.g., BMS-734016, MDX-010) and Tremelimumab (e.g., CP-675, CP-675,206). In some cases, the KIR antibody is Lirilumab (e.g., BMS-986015, IPH2102). In some cases the antibody against LAG3 is BMS986016. In some instances, the antibody against PD-1 is selected from Pembrolizumab (e.g., MK-3475, SCH 900475), Nivolumab (e.g., BMS-936558, MDX-1106, ONO-4538), and Pidilizumab (e.g., CT-011, MDV9300). In some cases, the antibody against PDL1 is selected from anti-PDL1 monoclonal antibody MDX-1105, Atezolizumab (e.g., MPDL3280A, RG7446, RO5541267), and BMS-936559 (e.g., MDX-1105). In some instances, the antibody against PS is Bavituximab. In some cases, the inhibitor is an IgG fusion protein. In some cases, the fusion protein directed against PD-1 is AMP-224. In some instances, the IgG protein directed against LAG3 is IMP321. In some instances, a combination of antibodies to several immune checkpoint inhibitors is administered in a method described herein.

In some instances, immune checkpoint inhibitor described herein comprises an RNA interfering agent. In some cases, the RNA interfering agent inhibits the expression of at least one of A2aR, B7H3, B7H4, BTLA, CTLA-4, IDO1, IDO2, KIR, LAG3, PD-1, PDL-1, PDL-2, PS, TIM3, or VISTA. In some instances, the RNA interfering agent is at least one of a small interfering RNA (siRNA), small hairpin RNA (shRNA), or a microRNA (miRNA). In some cases, an oligonucleotide complementary to at least one A2aR, B7H3, B7H4, BTLA, CTLA-4, IDO1, IDO2, KIR, LAG3, PD-1, PDL-1, PDL-2, PS, TIM3, or VISTA is used. In some instances, the immune checkpoint inhibitor is at least one of a small molecule, a peptide, a peptidomimetic, or a soluble version of the immune checkpoint.

In some instances, an immune checkpoint modulatory agent described herein reduces the expression of the immune checkpoint target. The expression of the immune checkpoint may be decreased by about 5-100, 10-90, 20-80, 30-70, 40-60, 50-95, 65-85, or 75-95%. The expression may be decreased by at least 5, 10, 15, 20, 25, 30, 35, 40, 45, 50, 55, 60, 65, 70, 76, 80, 85, 90, 95, 99, or 100%. The expression may be decreased by at least 5%. The expression may be decreased by at least 10%. The expression may be decreased by at least 30%. The expression may be decreased by at least 50%. The expression may be decreased by at least 70%. The expression may be decreased by at least 90%.

In some instances, an immune checkpoint modulatory agent described herein reduces the activity of the immune checkpoint target. The activity of the immune checkpoint may be decreased by about 5-100, 10-90, 20-80, 30-70, 40-60, 50-95, 65-85, or 75-95%. The activity may be decreased by at least 5, 10, 15, 20, 25, 30, 35, 40, 45, 50, 55, 60, 65, 70, 76, 80, 85, 90, 95, 99, or 100%. The activity may be decreased by at least 5%. The activity may be decreased by at least 10%. The activity may be decreased by at least 30%. The activity may be decreased by at least 50%. The activity may be decreased by at least 70%. The activity may be decreased by at least 90%. Exemplary activities include, without limitation, binding activity, phosphorylation, dephosphorylation, cell growth, cellular differentiation, cell migration and metabolic activity.

In some instances, an immune checkpoint modulatory agent described herein reduces the interaction between PD-1 and its ligands PDL-1 or PDL-2. In some instances, the immune checkpoint modulatory agent reduces the interaction between KIR and its ligand. In some cases, the immune checkpoint modulatory agent inhibits activation. In some cases, the immune checkpoint modulatory agent inhibits downstream signaling.

Immune Modulatory Agent Activators

In some instances, an immune checkpoint modulatory agent described herein activates the immune checkpoint target. In some cases, the immune checkpoint modulatory agent targets at least one of CD122, CD137, CD137L, CD27, CD28, CD40, CD70, CD80, CD86, GITR, GITRL, ICOS, ICOSL, OX-40, or OX-40L. In some cases, the immune checkpoint modulatory agent targets CD122. In some cases, the immune checkpoint modulatory agent targets CD137. In some cases, the immune checkpoint modulatory agent targets CD137L. In some instances, the immune checkpoint modulatory agent targets CD27. In some instances, the immune checkpoint modulatory agent targets CD28. In some instances, the immune checkpoint modulatory agent targets CD40. In some cases, the immune checkpoint modulatory agent targets CD40. In some cases, the immune checkpoint modulatory agent targets CD70. In some instances, the immune checkpoint modulatory agent targets CD80. In some cases, the immune checkpoint modulatory agent targets CD86. In some instances, the immune checkpoint modulatory agent targets GITR. In some cases, the immune checkpoint modulatory agent targets GITRL. In some instances, the immune checkpoint modulatory agent targets ICOS. In some cases, the immune checkpoint modulatory agent targets ICOSL. In some instances, the immune checkpoint modulatory agent targets OX-40. In some cases, the immune checkpoint modulatory agent targets OX-40L.

In some instances, an immune checkpoint modulatory agent described herein is an antibody directed to at least one of CD137, CD27, and GITR. In some instances, the antibody is at least one of monoclonal antibodies, synthetic antibodies, polyclonal antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), or epitope-binding fragments thereof. In some cases, the antibodies are immunoglobulin molecules or immunologically active portions of immunoglobulin molecules. In some instances, the antibodies are animal in origin including birds and mammals. In some cases, the antibodies are human or humanized monoclonal antibodies. In some instances, the antibody directed towards CD137 is Urelumab (e.g., BMS-663513). In some cases, the antibody is directed towards CD27 is Varlilumab (e.g., CDX-1127). In some instances, the antibody is directed towards GITR is TRX518.

In some instances, an immune checkpoint modulatory agent described herein activates an immune checkpoint. In some cases, the immune checkpoint modulatory agent targets at least one of CD122, CD137, CD137L, CD27, CD28, CD40, CD70, CD80, CD86, GITR, GITRL, ICOS, ICOSL, OX-40, or OX-40L. In some cases, the immune checkpoint modulatory agent is at least one of a small molecule, a peptide, a peptidomimetic, or a soluble version of the immune checkpoint modulatory agent.

In some cases, an immune checkpoint modulatory agent described herein increases the expression of an immune checkpoint pathway component. The expression of the immune checkpoint pathway component may be increased by about 5-100, 10-90, 20-80, 30-70, 40-60, 50-95, 65-85, or 75-95%. The expression may be increased by at least 5, 10, 15, 20, 25, 30, 35, 40, 45, 50, 55, 60, 65, 70, 76, 80, 85, 90, 95, 99, or 100%. The expression may be increased by at least 5%. The expression may be increased by at least 10%. The expression may be increased by at least 30%. The expression may be increased by at least 50%. The expression may be increased by at least 70%. The expression may be increased by at least 90%.

In some cases, the immune checkpoint modulatory agent increases the activity of the immune checkpoint target. The activity of the immune checkpoint may be increased by about 5-100, 10-90, 20-80, 30-70, 40-60, 50-95, 65-85, or 75-95%. The activity may be increased by at least 5, 10, 15, 20, 25, 30, 35, 40, 45, 50, 55, 60, 65, 70, 76, 80, 85, 90, 95, 99, or 100%. The activity may be increased by at least 5%. The activity may be increased by at least 10%. The activity may be increased by at least 30%. The activity may be increased by at least 50%. The activity may be increased by at least 70%. The activity may be increased by at least 90%.

Methods of Isolating and Priming Dendritic Cells (DC)

Provided herein are methods for priming DCs and administering the primed DCs to a subject in need thereof, wherein the DC induce a response from cytotoxic T lymphocytes (CTL) resulting in cytotoxicity of target cells. The DCs may comprise allogeneic dendritic cells or autologous dendritic cells. In some instances, the methods described herein comprise administering allogeneic primed dendritic cells to a subject. In some instances, the methods described herein comprise administering autologous primed dendritic cells to a subject. The methods disclosed herein comprising administering primed DCs to the subject may be referred to herein as "dendritic cell vaccination."

In some instances, methods described herein comprise obtaining dendritic cells from CD34+ progenitor cells in the bone marrow. In some instances, methods described herein comprise obtaining dendritic cells from CD1+CD14+ immature monocytes in the peripheral blood. In some instances, obtaining the dendritic cells comprises leukapheresis. In some instances, leukapheresis comprises withdrawing a unit of blood from the subject or a donor, separating a series of blood-components: red cells, platelets, and most of the plasma factors, which are returned to the subject, with the white blood cells remaining. In some instances, methods described herein comprise assessing the white blood cells for sterility, shipping or storing them cold (4° C.), and or processing the DCs from the apheresis product.

Methods of DCs production disclosed herein may comprise separating monocytes in the unit of blood from other white cells, including, but not limited to, T cells, B cells, NK cells, Eosinophils and Basophils. This may be accomplished with immuno-magnetic selection or by adherence properties. Immuno-magnetic selection involves contacting white blood cells from the unit of blood with a sterile plastic column with plastic beads coated with antibodies for immune cells, such as, by way of non-limiting example, CD surface proteins: (CD4, CD8, CD56, etc.). Unwanted (non-monocyte) cells will adhere to the beads, leaving the monocytes to pass through and be collected. In positive selection, magnetic beads may be coated with antibodies for CD1 and/or CD14 to capture monocytes, a magnet is placed against the column, and unwanted cells are flushed out of the column with a buffered saline solution or cell-viable media. The monocytes are then washed off the beads and collected in a following step. In adherence selection, the properties of monocytes to stick to certain surfaces are used to separate them by running the apheresis product down a slanted column.

Provided herein are methods for cell collection which may comprise collecting only a few thousand monocytes from the unit of blood. Effective immunotherapy generally requires DC doses in the range of 50 million. Thus, methods disclosed herein may comprise expanding monocytes, as well as any precursors thereof, and any cells differentiated therefrom (e.g., DCs). Expanding cells may comprise contacting cells with factors such as growth factors, colony-stimulation factors, cytokines, or any other proliferation or growth inducing factors, and combinations thereof. By way of non-limiting example, the recombinant human growth factors rhuInterleukin-4 (IL-4), and rhuGranulocyte-Macrophage-Colony-Stimulation Factor (GM-CSF), may be used to accomplish the expansion of DC numbers. In addition, IL-4 and GM-CSF may be required to develop mature DCs from monocytes, which have poor antigen-uptake and CTL-stimulating ability, compared to mature DCs. Thus, IL-4 and GM-CSF may expand the number and the development of mature-DC markers. DC markers may include, but are not limited to CD11, CD80, and CD83, as well as increased expression of both Class I (for presentation of short peptides to CD8+ cells), and Class II (for presentation of longer peptides to CD4+Helper-Inducer T lymphocytes) MHC complexes. Expanding cells may produce mature D DCs C in the tens of millions within about 2 days. Expanding cells may produce mature DCs in the tens of millions within about 3 days. Expanding cells may produce mature DCs in the tens of millions within about 4 days. Expanding cells may produce mature DCs in the tens of millions within about 5 days. Expanding cells may produce mature DCs in the tens of millions within about one week.

In some instances, methods described herein comprise contacting or pulsing DCs with peptides/antigens, tumor cells, tumor supporting cells, tumor cell lysate and/or tumor supporting cell lysate. The term "pulsing," as used herein, generally refers to contacting the cells more than once at one or more intervals, and may be used interchangeably with contacting, unless specified otherwise. In some instances, the methods comprise contacting or pulsing DCs with a peptide that binds MHC Class I molecules ("MHC Class I peptide"). In some instances, methods described herein comprise contacting or pulsing DC with a peptide that binds MHC Class II molecules ("MHC Class II peptides"). In some instances, methods described herein comprise contacting or pulsing DC with MHC Class I peptides and MHC Class II peptides. In some instances, the contacting or pulsing makes the DCs competent to prime CTL and target CTL to tumors. In some instances, methods described here comprise contacting or pulsing DC with manufactured/synthetic Class I and/or Class II peptides. In some instances, the Class I and/or class II peptides are manufactured, then added to the DC medium, optionally in in microgram quantities or less. In some instances, methods described herein include Class II peptides for a sustained immune response. In some instances, methods described herein comprise DNA or RNA sequencing of the peptide (i.e. tumor antigen) and/or using electroporation to insert the DNA or RNA into the DCs to trigger antigen processing. In some instances, methods described herein do not require HLA matching of DCs. In some instances, the peptide or portion thereof is represented by an amino acid sequence selected from EGSRNQDWL (SEQ ID NO: 28), (TAYRYHLL) (SEQ ID NO: 29), or combinations thereof.

Class I peptides may by manufactured, then added to the DC medium in microgram quantities. However, this technique is costly, because the peptides must be matched to the subject's HLA type, and if the tumor cell does not present that antigen, it can evade detection and lysis. The lack of Class II peptides to activate CD4+ help leads to rapid decline of immune response power. Other methods may comprise RNA sequencing of common tumor antigens, then using electroporation to insert the RNA into the DCs to trigger antigen processing. This method does not require HLA matching, and includes Class II peptides for a sustained immune response. However, RNA sequencing may be technically complex, and may only present a limited number of antigens of thousands of potential gene products. For these reasons, autologous whole-tumor cells or their lysate have the advantages of low cost, ready availability by biopsy (1-2 gm sufficient), and contain the full array of potential antigens for a broad and deep immune response.

Methods for dendritic cell priming described herein may comprise obtaining whole tumor cells and/or lysates thereof. Tumor cells may be killed by radiation or other means and preparing lysate by various methods. In some instances, lysing the tumor cells does not comprise trypsin enzyme digestion and freeze-thaw cycles, which are simple and fast, but can damage the delicate peptides within. The methods disclosed herein may employ an automated cell processor (e.g. the Miltenyi GentleMACS system), which allows the sample to be manually minced, suspended in PBS solution, then a pre-selected tissue-specific software-controlled rotor system separates the tumor cells. The single-cell suspension may be membrane-lysed with minimal damage to tumor peptides.

Methods for dendritic cell priming described herein may comprise contacting the dendritic cells with autologous tumor cells or lysates thereof. In some instances, methods described herein comprise contacting the dendritic cells with autologous whole-tumor cells (e.g. tumor cells and tumor supporting cells) or lysates thereof which contain the full array of potential antigens for a broad and deep immune response. Methods for dendritic cell priming described herein may comprise contacting the dendritic cells with tumor cell lysate comprising apoptotic or necrotic bodies. In further instances, the tumor cell lysate comprises tumor antigens from the microenvironment surrounding the tumor cells, such as extracellular matrix proteins.

Methods for dendritic cell priming described herein may comprise contacting the DCs with an augmenting agent that will augment the priming, proliferation or viability of the DCs. By way of non-limiting example, the augmenting agent may be selected from lymphokines, monokines, cytokines, growth factors, cells, cell fragments, (non-protein) small molecules, antibodies, antibody fragments, nucleic acids, and combinations thereof.

Methods for preparing cells and antigens for DC priming may comprise rendering the target cells (e.g., cancer cells) incapable of cell division. For example, the methods may comprise treating cells with mytomycin C or radiation to render cells incapable of cell division. These may include cells that are added as augmenting agents or cells used to pulse DCs (e.g., tumor cells).

In some instances, methods described herein comprise pulsing the DCs from about 1 hour to about 24 hours. In some instances, methods described herein comprise pulsing the DCs from about 12 hours to about 48 hours. In some instances, methods described herein comprise pulsing the DCs from about 8 hours to about 24 hours. In some instances, methods described herein comprise pulsing the DCs for about 18 hours. Pulsing may comprise contacting the DCs at least once with the peptides/antigens, tumor cells, tumor supporting cells, tumor cell lysate and/or tumor supporting cell lysate. Pulsing may comprise contacting the DCs at least twice with the peptides/antigens, tumor cells, tumor supporting cells, tumor cell lysate and/or tumor supporting cell lysate. Pulsing may comprise contacting the DCs at least three times with the peptides/antigens, tumor cells, tumor supporting cells, tumor cell lysate and/or tumor supporting cell lysate. Pulsing may comprise contacting the DCs less than two times, less than three times, less than four times, less than five times, or less than 10 times with the peptides/antigens, tumor cells, tumor supporting cells, tumor cell lysate and/or tumor supporting cell lysate. Pulsing may comprise adding the peptides/antigens, tumor cells, tumor supporting cells, tumor cell lysate and/or tumor supporting cell lysate to the DC more than once, such that the peptides/antigens, tumor cells, tumor supporting cells, tumor cell lysate and/or tumor supporting cell lysate accumulates in the DC culture media. Pulsing may comprise washing the cells or removing the DC culture media between one or more pulses.

Methods described herein may comprise contacting DC with a maturing agent to enhance, complete or finalize the maturation of the DC. In some instances, the maturing agent also acts as a "danger signal." Without this danger signal, the tumor antigen may induce Treg production or activity, which will ultimately lower CTL activity. In some cases, the maturing agent/danger signal is an inflammatory signal. The inflammatory signal may also be referred to as an inflammatory mediator. Inflammatory mediators may include cytokines, as well as other factors (e.g., chemokines, adhesion molecules, etc.), that may not be classified by those in the art as cytokines, but affect inflammation either directly or indirectly. In some instances, the inflammatory mediator is selected from a chemokine, a cytokine, a pathogen, a non-peptidic small molecule, a compound, an antibody, a peptide, fragments thereof, portions thereof, and combinations thereof. In some instances, the inflammatory signal is a modulator of a pattern recognition receptor (PRR) or pathway thereof.

In some cases, inflammatory signals are selected from an interferon, a toll-like receptor signaling modulator, and combinations thereof. By way of non-limiting example, the interferon may be interferon-gamma. In some instances, the inflammatory signal is a toll-like receptor signaling pathway modulator.

In some cases, the inflammatory signal is a toll-like receptor (TLR) signaling pathway regulator. By way of non-limiting example, the toll-like receptor signaling pathway regulator may be lipopolysaccharide (LPS), a polysaccharide from bacterial cell walls.

The toll-like receptor signaling pathway regulator may be selected from a toll-like receptor signaling pathway regulator that regulates TLR1, TLR2, TLR3, TLR4, TLR5, TLR6, TLR7, TLR8, TLR9 and TLR 10. The toll-like receptor signaling pathway regulator may be a ligand, a binding protein, an antibody, an agonist or an antagonist, of a TLR. The toll-like receptor signaling pathway regulator may be selected from a peptide, a protein, a cell fragment, a cell-wall component, a lipoprotein, a peptidoglycan, a polysaccharide, a monosaccharide, and a small molecule compound. The toll-like receptor signaling pathway regulator may be a portion of an animal cell, a plant cell, a bacterial cell, a yeast cell, a fungal cell, and combinations thereof. The toll-like receptor signaling pathway regulator may be a TLR2 signaling pathway regulator. By way of non-limiting example, the TLR2 signaling pathway regulator may be lipoteichoic acid, MALP-2, MALP-4, OspA, Porin, LcrV, lipomannan, GPI anchor, lysophosphatidylserine, lipophosphoglycan, glycophosphatidylinositol, zymosan, hsp60, and hemagglutinin. The toll-like receptor signaling pathway regulator may be a TLR4 signaling pathway regulator. By way of non-limiting example, the TLR4 signaling pathway regulator may be buprenorphine, carbamazepine, ethanol, fentanyl, levorphanol, LPS, methadone, morphine, oxcarbazepine, oxycodone, pethidine, and glucuronoxylomannan. The toll-like receptor signaling pathway regulator may be a TLR7 signaling pathway regulator. By way of non-limiting example, the TLR7 signaling pathway regulator may be a single stranded RNA or an imidazoquinoline compound. The toll-like receptor signaling pathway regulator may be a TLR8 signaling pathway regulator. By way of non-limiting example, the TLR8 signaling pathway regulator may be a single stranded RNA, a G-rich oligonucleotide or an imidazoquinoline compound. The imidazolquinoline compound may be R848.

After exposure to the inflammatory signal, the DC may up-regulate their CD80/CD83+activation markers, increase production of IL-12p70 to induce a Type 1 CTL response, and become resistant to further antigen uptake and processing.

Methods for producing primed dendritic cells described herein may comprise contacting primed dendritic cells with interferon gamma. In some instances, the methods comprise culturing the primed dendritic cells in a culture media with a concentration of interferon gamma selected from about 100 U/mL to about 10,000 U/mL, about 500 U/mL to about 5000 U/mL, and about 500 U/mL to about 2,000 U/mL. In some cases, the methods comprise culturing the primed dendritic cells in a culture media with a concentration of interferon gamma of about 500 U/mL. In some cases, the methods comprise culturing the primed dendritic cells in a culture media with a concentration of interferon gamma of about 1000 U/mL. In some instances, the methods comprise culturing the primed dendritic cells in a culture media with a concentration of interferon gamma of about 2000 U/mL.

Methods for producing primed dendritic cells described herein may comprise contacting primed dendritic cells with TLR8 agonist R848. In some cases, the methods comprise culturing the primed dendritic cells in a culture media with a concentration of R848 selected from about 0.1 µg/mL to about 50 µg/mL, about 1 µg/mL to about 20 µg/mL, and about 1 µg/mL to about g/mL. In some cases, the methods comprise culturing the primed dendritic cells in a culture media with a concentration of R848 of about 1 µg/mL. In some cases, the methods comprise culturing the primed dendritic cells in a culture media with a concentration of R848 of about 5 g/mL. In some cases, the methods comprise culturing the primed dendritic cells in a culture media with a concentration of R848 of about 10 µg/mL.

Methods for producing primed dendritic cells described herein may comprise contacting primed dendritic cells with lipopolysaccharide. In some instances, the methods comprise culturing the primed dendritic cells in a culture media with a concentration of lipopolysaccharide selected from about 1 ng/mL to about 100 ng/mL, about 1 ng/mL to about 50 ng/mL, and about 1 ng/mL to about 25 ng/mL. In some instances, the methods comprise culturing the primed dendritic cells in a culture media with a concentration of lipopolysaccharide of about 5 ng/mL. In some instances, the methods comprise culturing the primed dendritic cells in a culture media with a concentration of lipopolysaccharide of about 10 ng/mL. In some instances, the methods comprise culturing the primed dendritic cells in a culture media with a concentration of lipopolysaccharide of about 15 ng/mL.

Methods described herein may comprise sterility, specificity, and viability assessment of the DCs. The testing may occur before shipping or storing the DCs. The testing may occur after shipping or storing the DCs. The methods may comprise measuring expression level of IL-12p70 in DCs, either at the RNA or protein level. IL-12p70 is an independent predictor of clinical response, tested across numerous trials in the last two decades, some with about 40% response rates. The expression level of IL-12p70 in primed DCs produced by the methods disclosed herein may be at least about two times greater than primed DCs produced/stored/shipped by traditional methods. The expression level of IL-12p70 in primed DCs produced by the methods disclosed herein may be at least about two times greater than primed DCs produced/stored/shipped by traditional methods ("traditional primed DC"). The expression level of IL-12p70 in primed DCs may be at least about 10%, at least about 20%, at least about 30%, at least about 40%, at least about 50%, at least about 60%, at least about 70%, at least about 80%, at least about 90%, or at least about 100% greater than traditional primed DCs. The expression level of IL-12p70 in primed DCs may be at least about three times greater than traditional primed DCs. The expression level of IL-12p70 in primed DCs may be at least about four times greater than traditional primed DCs. The expression level of IL-12p70 in primed DCs produced by the methods disclosed herein may be about two to about twenty times greater than traditional primed DCs.

Provided herein are dendritic cells that produce more than 6 ng/mL of IL-12p70. In some instances, provided herein are dendritic cells that produce at least about 6.5 ng/mL of IL-12p70. In some instances, provided herein are dendritic cells that produce more than 10 ng/mL of IL-12p70. In some instances, DCs produced by methods described herein produce at least about 10 ng/mL IL-12p70, at least about 12 ng/mL IL-12p70, at least about 14 ng/mL IL-12p70, at least about 16 ng/mL IL-12p70, at least about 18 ng/mL IL-12p70, at least about 20 ng/mL IL-12p70, at least about 22 ng/mL IL-12p70, or at least about 24 ng/mL IL-12p70. In some instances, DCs produced by methods described herein produce about 10 ng/mL to about 30 ng/mL. In some instances, DCs produced by methods described herein produce from about 10 ng/mL to about 25 ng/mL IL-12p70. In some instances, DCs produced by methods described herein produce from about 15 ng/mL to at least about 23 ng/mL IL-12p70. In some instances, DCs produced by methods described herein produce from about 6.5 ng/mL to at least about 23 ng/mL IL-12p70.

CTL Response

Methods for producing DCs described herein may comprise testing the ability of the DCs to induce a CTL response. Measuring the level of the CTL response may comprise measuring cytokines or inflammatory mediators in blood, serum or plasma from the subject. Measuring the level of the CTL response may comprise measuring a change in the level of a cytokine or inflammatory mediator in blood, serum or plasma from the subject. Measuring the level of the CTL response may comprise measuring the production of a cytokine or inflammatory mediator in vitro. Cytokines and inflammatory mediators may include interleukins, migration inhibitory proteins, monocyte chemotactic proteins, monocyte chemoattractant proteins, interferons, tumor necrosis factors, colony stimulating factors (CSFs), macrophage inflammatory proteins, monokines, chemokines, chemokine ligands (CCLs), and C-X-C motif chemokines (CXCL), and receptors thereof. Cytokines and inflammatory mediators include, but are certainly not limited to, interleukin 1 beta (IL-1b), interleukin 2 (IL-2), interleukin 4 (IL-4), interleukin 5 (IL-5), interleukin 7 (IL-7), interleukin 8 (IL-5), interleukin 10 (IL-10), interleukin 13 (IL-13), interleukin 6 (IL-6), interleukin 12 (IL-12), interleukin 15 (IL-15), interleukin 17 (IL-17), Rantes, Eotaxin, macrophage inflammatory protein 1 alpha (MIP-1a), macrophage inflammatory protein 1 beta (MIP-1b), granulocyte macrophage colony-stimulating factor (GM-CSF), monocyte chemoattractant protein-1 (MCP-1), interferon alpha (IFNa), interferon gamma (IFNg), interleukin 1 receptor alpha (IL-1Ra), interleukin 2 receptor (IL-2R), tumor necrosis factor alpha (TNFa), interferon gamma induced protein (IP-10), and monokine induced by gamma interferon (MIG). CTL response may be measured by expression of tumor response genes (MxA, etc.), enabling high cancer killing (turning "cold" tumors "hot"), and generating further tumor shrinkage in non-responder or low responders.

Hard Surface

Methods for DC preparation described herein may comprise culturing DCs on a hard surface. The term, "hard surface," as used herein, generally refers to a standard plastic tissue culture plate or flask (e.g. a polystyrene plate). The methods disclosed herein comprise culturing DCs on a hard surface to which the DCs can adhere. In some cases, the hard surface is coated with a protein, peptide, extracellular matrix molecule, polymer, or combinations thereof. In some cases, the hard surface is not coated (e.g., the DCs adhere directly to the hard plastic surface). The hard surface is contrasted to a soft tissue culture bag, also known as cell differentiation bags. Soft tissue culture bags may be bags comprising polymers or chemicals (e.g. phthalates) that reduce the DC's Type 1 response capability. Soft tissue culture bags may be bags comprising polymers or chemicals that evoke a neutral Type 0 response from the DCs, rendering the DCs functionally inert. Soft tissue culture bags may be bags comprising a polymer selected from polyethylene, fluorinated ethylene propylene (FEP), hexafluoropropylene, tetrafluoroethylene, polytetrafluoroethylene, and co-polymers thereof, and combinations thereof.

Methods for DC preparation described herein may comprise transferring the DCs to a storage unit. The storage unit may also be a shipping unit. The storage unit may be selected from a flexible or soft container or surface (e.g., a bag) or a hard container or surface (e.g., a flask or plate). The storage unit may comprise a hard plastic surface. The storage unit may consist essentially of a hard plastic surface. The storage unit may consist of a hard plastic surface. The storage unit may comprise a non-plastic surface (e.g., glass). The storage unit may consist essentially of a non-plastic surface. The storage unit may consist of a non-plastic surface.

The storage unit may be free of any polymers that would be taken up by, and/or induce a response in, cells stored within the storage unit. The storage unit may be free or essentially free of polymers that induce a neutral or Type 0 response in immature DCs. A neutral response may be characterized by low expression of IL-12p70. The storage unit may be essentially free of any polymers that would be taken up by, and/or induce a response in, cells stored within the storage unit. Essentially free may mean that the storage unit is at least 90%, at least 95%, at least 98%, or at least 99% free of any polymers that would be taken up by, and/or induce a response in, cells stored within the storage unit. Essentially free may mean that the storage unit is at least 99.5%, at least 99.6%, at least 99.7%, at least 99.8%, or at least 99.9% free of any polymers that would be taken up by, and/or induce a response in, cells stored within the storage unit.

Provided herein are storage units for storing DCs produced by methods described herein, wherein the storage units comprise an inner surface, wherein the inner surface is the surface of the storage unit that is in contact with cells stored therein. The inner surface may consist of a hard plastic surface. The inner surface may be glass. The inner surface may be absent of any polymers that would be taken up by, and/or induce a response in, cells stored within the storage unit. The inner surface may be constructed of polymers that are not taken up by immature DC or any cells stored within the storage unit. The inner surface may be free of any polymers that would be taken up by, and/or induce a response in, cells stored within the storage unit. The inner surface may be essentially free of any polymers that would be taken up by, and/or induce a response in, cells stored within the storage unit. The inner surface may be at least 90%, at least 95%, at least 98%, or at least 99% free of any polymers that would be taken up by, and/or induce a response in, cells stored within the storage unit following addition of cells and storage media. The inner surface may be at least 99.5%, at least 99.6%, at least 99.7%, at least 99.8%, or at least 99.9% free of any polymers that would be taken up by, and/or induce a response in, cells stored within the storage unit following addition of cells and storage media. The inner surface may be free or essentially free of polymers that induce a neutral or Type 0 response in immature DCs. A neutral response may be characterized by low expression of IL-12p70.

Provided herein are storage units for storing DCs produced by methods described herein, wherein the storage units are suitable for freezing at −70° C. in liquid N2, storage up to 1 year, and shipping to the clinic for use. The methods may comprise storing and/or shipping mature DCs, immature DCs, monocytes or blood in a storage unit. The methods may comprise shipping cells cool overnight. The methods may comprise thawing or warming cells to 37° C. (e.g., in a warm-water bath).

Methods of Isolating and Lysing Tumor Cells

Provided herein are methods for treating a subject, comprising administering the DCs disclosed herein to target tumor cells. In some instances, DCs are primed with tumor cells from a subject. In some instances, the tumor cells are isolated cells from a tumor microenvironment of the subject, referred to herein as tumor supporting cells. In some instances, dendritic cells are exposed to/pulsed with tumor cells, tumor supporting cells and/or peptides thereof, such that the dendritic cells will target tumor cells and/or tumor supporting cells that support tumor growth and metastasis (e.g. endothelial cells, vascular cells, immune cells, etc.). In some instances, peptides/antigens from tumor cells and tumor supporting cells induce dendritic cells or cytotoxic lymphocytes with receptors for peptides/antigens on both tumor cells and tumor supporting cells, resulting in targeting of the dendritic cells or cytotoxic lymphocytes to the tumor microenvironment rather than only the tumor cells. In some instances, tumor cells and/or tumor supporting cells are obtained from a biopsy of tumor tissue. In some instances, the biopsy comprises cells selected from tumor cells, adipocytes, fibroblasts, endothelial cells, infiltrating immune cells, and combinations thereof. In some cases, the methods comprise expanding tumor cells in order to have a sufficient number of tumor cells, tumor cell lysates or tumor cell antigens to effectively and optimally prime/pulse the DC. Expanding may comprise proliferating of the tumor cells in vitro.

Provided herein are methods for activating DCs disclosed herein to target tumor cells, wherein the DCs are activated with lysed tumor cells and/or tumor supporting cells and surrounding extracellular matrix. In some instances, lysing comprises contacting the tumor cells and/or tumor supporting cells with an NH4Cl enzyme solution to eliminate red blood cells. In some instances, the lysing comprises contacting the tumor cells and/or tumor supporting cells with hypochlorous acid solution to induce immunogenic cell death. In some instances, the cells are lysed gently enough to not destroy peptides. In some instances, the cells are lysed to produce apoptotic or necrotic bodies. In some instances, the methods comprise lysing the tumor cells and/or tumor supporting cells with an enzymatic solution. In some instances, the methods comprise lysing the tumor cells and/or tumor supporting cells with a peroxide-free solution or a low peroxide-containing solution.

Provided herein are methods for activating DCs disclosed herein comprising lysing the tumor cells with a hypochlorite solution (HOCL). In some instances, the hypochlorite solution comprises sodium chlorite. In some instances, the hypochlorite solution comprises calcium chlorite. In some instances, the concentration of the hypochlorite in a media in which the tumor cells are suspended is about 10 μM, about 20 μM, about 30 μM, about 40 μM, about 50 μM, about 60 μM, about 70 μM, about 80 μM, about 90 μM, or about 100 μM.

Provided herein are methods for methods activating DCs comprise lysing the tumor cells and/or tumor supporting cells with a detergent solution prior to contact with the DCs. In some instances, the detergent is selected from, but is not limited to, Triton X-100, Triton X-114, NP-40, Brij-35, Brij-58, Tween 20, Tween 80, octyl glucoside, octyl thioglucoside, SDS, CHAPS, and CHAPSO. In some instances, the detergent solution is purified of peroxides, and other impurities. In some instances, the detergent is about 0.1% to about 10% v/v of the detergent solution. In some instances, the detergent is about 0.1% to about 5% v/v of the detergent solution. In some instances, the detergent is about 0.5% to about 5% v/v of the detergent solution. In some instances, the detergent is about 1% to about 10% v/v of the detergent solution. In some instances, the detergent is about 1% to about 5% v/v of the detergent solution. In some instances, the methods comprise lysing cells without shaking, vortexing, freezing, thawing, shear pressure, sonicating and/or heating the cells.

In some instances, methods for cell lysis described herein further comprise stopping or neutralizing the lysing. For example, cells may be washed with a buffered saline solution (phospho-buffered saline solution or Hank's balanced salt solution) to neutralize the lysing.

Combination Therapy

Provided herein are combination therapies comprising therapeutic agents disclosed herein with other types of therapies in order to achieve an optimal result. For example, in some instances, combination approaches to cancer immunotherapy may be more successful than single-axis attacks which tumors can mutate to avoid. In some cases, the therapy is a cancer therapy. Cancer therapies include, but are not limited to, chemotherapy, radiation, small molecule inhibitors, and monoclonal antibodies.

Provided herein are compositions and methods wherein dendritic cell vaccination is combined with co-administration of an adjuvant effect of a virus to overcome tumor immune evasion mechanisms and deplete tumor cells and an effective amount of an immune checkpoint modulatory agent. In some instances, the immune checkpoint modulatory agent is administered with an Arbovirus. In some cases, the immune checkpoint modulatory agent is administered with DV. In some cases, the immune checkpoint modulatory agent is administered with an Alphavirus. In some instances, the immune checkpoint modulator agent is administered with CV. A schematic representation of the combination therapies disclosed herein is depicted in FIG. 1. Methods described here may be used to treat a subject for cancer by obtaining dendritic cells and tumor cells from the subject, exposing the dendritic cells to the tumor cells or tumor cell lysate, also referred to as "pulsing" the dendritic cells, to primed (or "activated") the dendritic cells, delivering the resulting primed and tumor-targeting dendritic cells to the subject after the subject has had his/her immune system stimulated with the virus (see, e.g., FIG. 1). A therapeutic effective amount of an immune checkpoint modulatory agent is co-administered with the virus. Optionally, a tumor antigen that is not from the subject can be used for pulsing the dendritic cells.

Provided herein are compositions and methods wherein dendritic cell vaccination is combined with co-administration of an adjuvant effect of a virus to overcome tumor immune evasion mechanisms and deplete tumor cells and an effective amount of an immune checkpoint modulatory agent. Provided herein are compositions wherein Dengue virus therapy is utilized as an adjuvant along with immune checkpoint inhibition. In some cases, an immune checkpoint modulatory agent is at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA.

Tumor immune evasion mechanisms are responsible for the lack of efficacy seen with most immunotherapy platforms. Compositions and methods described herein provide for a multi-pronged approach, combining physiological (hyperthermic reduction of tumor perfusion), immunological (activation of effector cells of the adaptive and innate immune system), and apoptosis-inducing pathways (sTRAIL) to destroy tumor cells. Using a virus, like Dengue virus (DV), as an adjuvant to activate many pathways working in synergy may support the eradication of mutated tumor cells, improving the clinical efficacy of the cancer immunotherapy. Methods described herein provide cancer immunotherapies based on multiple mechanisms of action in concert and result in a decline in the ability of the tumor cells to employ resistance methods compared to delivery of any single method along. Provided herein are compositions wherein Dengue virus therapy is utilized as an adjuvant along with immune checkpoint inhibition.

Provided herein are methods for treating a subject having a disease or condition, comprising: obtaining dendritic cells (DCs); incubating the DCs with at least one tumor cell antigen; co-administering a virus and a therapeutic effective amount of an immune checkpoint modulatory agent to the subject; and administering the DCs to the subject. In some instances, the dendritic cells are autologous dendritic cells. In some instances, the dendritic cells are allogeneic dendritic cells. In some instances, incubating the DCs with at least one tumor antigen comprises incubating the DCs with a tumor cell. In some instances, incubating the DCs with at least one tumor antigen comprises incubating the DCs with a tumor cell lysate. In some instances, incubating the DCs with at least one tumor antigen comprises incubating the DC with a peptide expressed by a tumor cell. In some cases, the condition or disease is cancer. In some cases, the virus is anArbovirus. In some cases, the virus is a Dengue virus. In some cases, the virus is an Alphavirus. In some instances, the virus is Chikungunya virus. In some cases, the immune checkpoint modulatory agent is at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA.

Disclosed herein are methods for treating cancer in a subject in need thereof, comprising: obtaining dendritic cells (DCs); incubating the DCs with at least one tumor cell antigen; co-administering a Dengue Virus Type 2 serotype strain to the subject and a therapeutic effective amount of an immune checkpoint modulatory agent; and administering the DCs to the subject. In some instances, the Dengue Virus Type 2 serotype strain is DENV-2 #1710. In some instances, the dendritic cells are autologous dendritic cells. In some instances, the dendritic cells are allogeneic dendritic cells. In some instances, incubating the DCs with at least one tumor antigen comprises incubating the DCs with a tumor cell. In some instances, incubating the DCs with at least one tumor antigen comprises incubating the DCs with a tumor cell lysate. In some instances, the immune checkpoint modulatory agent is at least one of CD244, A2aR, CD276, VTCN1, B7H6, B7RP1, BTLA, butyrophilin, CD103, CD122, CD137, CD137L, CD160, CD2, CD200R, CD226, CD26, CD27, CD28, CD30, CD39, CD40, CD48, CD70, CD73, CD80, CD86, CEACAM1, CGEN-15049, CTLA-4, DR3, GAL9, GITR, GITRL, HVEM, ICOS, ICOSL, IDO1, IDO2, ILT-2, ILT-4, KIR, KLRG1, LAG3, LAIR1, TNFSF14, MARCO, NKG2A, NKG2D, OX-40, OX-40L, PD-1, PDL-1, PDL-2, PS, SIRPalpha, SLAM, TGFR, TIGIT, TIM1, TIM3, TIM4, or VISTA.

Co-administering the primed DCs, the virus, and the immune checkpoint modulatory agent may increase cancer cell death or cancer cell lysis beyond that induced by DCs and the virus. Cancer cell death may be increased by at least about 10% to 25%, at least about 10% to about 50%, at least about 20% to about 100%, at least about at least about 20% to about 200%. Cancer cell death may be increased by at least 5%, at least 10%, at least 20%, at least 30%, at least 40%, at least 50%, at least 60%, at least 70%, at least 80%, at least 90%, or at least 95%. Co-administering the primed DCs, the virus, and the immune checkpoint modulatory agent may reduce the size of tumor lesions beyond that reduced by DCs and the virus. Tumor lesion size may decrease by at least about 10% to about 50%, at least about 10% to about 30%, at least about 15% to about 80%. Tumor lesion size may decrease by at least 5%, at least 10%, at least 20%, at least 30%, at least 40%, at least 50%, at least 60%, at least 70%, at least 80%, at least 90%, or at least 95%. Co-administering the primed DCs, the virus, and the immune checkpoint modulatory agent may reduce the number of myeloid-derived suppressor cells (MDSC) in the tumor microenvironment beyond that decreased by DCs and the virus. Co-administering the primed DCs, the virus, and the immune checkpoint modulatory agent may reduce the number of myeloid-derived suppressor cells (MDSC) in the tumor microenvironment by at least about 10% to about 65%, at least about 10% to about 85%, at least about 10% to about 100%, or at least about 10% to about 200%.

Co-administering the primed DCs, the virus, and the immune checkpoint modulatory agent may increase cancer cell death or cancer cell lysis similar to that induced by DCs and the virus. Cancer cell death may be increased by at least about 10% to 25%, at least about 10% to about 50%, at least about 20% to about 100%, at least about at least about 20% to about 200%. Cancer cell death may be increased by at least 5%, at least 10%, at least 20%, at least 30%, at least 40%, at least 50%, at least 60%, at least 70%, at least 80%, at least 90%, or at least 95%. Co-administering the primed DCs, the virus, and the immune checkpoint modulatory agent may reduce the size of tumor lesions similar to that reduced by DCs and the virus. Tumor lesion size may decrease by at least about 10% to about 50%, at least about 10% to about 30%, at least about 15% to about 80%. Tumor lesion size may decrease by at least 5%, at least 10%, at least 20%, at least 30%, at least 40%, at least 50%, at least 60%, at least 70%, at least 80%, at least 90%, or at least 95%. Co-administering the primed DCs, the virus, and the immune checkpoint modulatory agent may reduce the number of myeloid-derived suppressor cells (MDSC) in the tumor microenvironment similar to that decreased by DCs and the virus. Co-administering the primed DCs, the virus, and the immune checkpoint modulatory agent may reduce the number of myeloid-derived suppressor cells (MDSC) in the tumor microenvironment by at least about 10% to about 65%, at least about 10% to about 85%, at least about 10% to about 100%, or at least about 10% to about 200%. Co-administering the primed DCs, the virus, and the immune checkpoint modulatory agent may reduce the number of myeloid-derived suppressor cells (MDSC) in the tumor microenvironment by at least 5%, at least 10%, at least 20%, at least 30%, at least 40%, at least 50%, at least 60%, at least 70%, at least 80%, at least 90%, or at least 95%.

Co-administering the virus and the immune checkpoint modulatory agent may increase cancer cell death or cancer cell lysis beyond that induced by DCs alone. Cancer cell death may be increased by at least about 10% to 25%, at least about 10% to about 50%, at least about 20% to about 100%, at least about at least about 20% to about 200%. Cancer cell death may be increased by at least 5%, at least 10%, at least 20%, at least 30%, at least 40%, at least 50%, at least 60%, at least 70%, at least 80%, at least 90%, or at least 95%. Co-administering the virus and the immune checkpoint modulatory agent may reduce the size of tumor lesions beyond that reduced by DCs alone. Tumor lesion size may decrease by at least about 10% to about 50%, at least about 10% to about 30%, at least about 15% to about 80%. Tumor lesion size may decrease by at least 5%, at least 10%, at least 20%, at least 30%, at least 40%, at least 50%, at least 60%, at least 70%, at least 80%, at least 90%, or at least 95%. Co-administering the virus and the immune checkpoint modulatory agent may reduce the number of myeloid-derived suppressor cells (MDSC) in the tumor microenvironment beyond that decreased by DCs alone. Co-administering the virus and the immune checkpoint modulatory agent may reduce the number of myeloid-derived suppressor cells (MDSC) in the tumor microenvironment by at least about 10% to about 65%, at least about 10% to about 85%, at least about 10% to about 100%, or at least about 10% to about 200%. Co-administering the virus and the immune checkpoint modulatory agent may reduce the number of myeloid-derived suppressor cells (MDSC) in the tumor microenvironment by at least 5%, at least 10%, at least 20%, at least 30%, at least 40%, at least 50%, at least 60%, at least 70%, at least 80%, at least 90%, or at least 95%.

Co-administering the virus and the immune checkpoint modulatory agent may increase cancer cell death or cancer cell lysis similarly to that induced by DCs alone. Cancer cell death may be increased by at least about 10% to 25%, at least about 10% to about 50%, at least about 20% to about 100%, at least about at least about 20% to about 200%. Cancer cell death may be increased at least 5%, at least 10%, at least 20%, at least 30%, at least 40%, at least 50%, at least 60%, at least 70%, at least 80%, at least 90%, or at least 95%. Co-administering the virus and the immune checkpoint modulatory agent may reduce the size of tumor lesions similar to that reduced by DCs alone. Tumor lesion size may decrease by at least about 10% to about 50%, at least about 10% to about 30%, at least about 15% to about 80%. Tumor lesion size may decrease by at least 5%, at least 10%, at least 20%, at least 30%, at least 40%, at least 50%, at least 60%, at least 70%, at least 80%, at least 90%, or at least 95%. Co-administering the virus and the immune checkpoint modulatory agent may reduce the number of myeloid-derived suppressor cells (MDSC) in the tumor microenvironment similar to that decreased by DCs alone. Co-administering the virus and the immune checkpoint modulatory agent may reduce the number of myeloid-derived suppressor cells (MDSC) in the tumor microenvironment by at least about 10% to about 65%, at least about 10% to about 85%, at least about 10% to about 100%, or at least about 10% to about 200%. Co-administering the virus and the immune checkpoint modulatory agent may reduce the number of myeloid-derived suppressor cells (MDSC) in the tumor microenvironment by at least 5%, at least 10%, at least 20%, at least 30%, at least 40%, at least 50%, at least 60%, at least 70%, at least 80%, at least 90%, or at least 95%.

Reduction in cancer may be a decrease in tumor size. Tumor size may decrease by about 5-100, 10-90, 20-80, 30-70, 40-60, 50-95, 65-85, or 75-95%. The decrease in tumor size may by at least 2, 5, 10, 15, 20, 25, 30, 35, 40, 45, 50, 55, 60, 65, 70, 76, 80, 85, 90, 95, 99, or 100%. The decrease in tumor size may by at least 2%. The decrease in tumor size may by at least 5%. The decrease in tumor size may by at least 10%. The decrease in tumor size may by at least 30%. The decrease in tumor size may be by at least 50%.

Reduction in cancer may be an increase in long term survival compared to patients not treated with an immune checkpoint inhibitor alone or accompanying DV. Long term survival may be increased by about 5-100, 10-90, 20-80, 30-70, 40-60, 50-95, 65-85, or 75-95%. Long term survival may be increased by at least 2, 5, 10, 15, 20, 25, 30, 35, 40, 45, 50, 55, 60, 65, 70, 76, 80, 85, 90, 95, 99, or 100%. Long term survival may be increased by at least 2%. Long term survival may be increased by at least 5%. Long term survival may be increased by at least 10%. Long term survival may be increased by at least 30%. Long term survival may be increased by at least 50%.

In some instances, the reduction in cancer may be a decrease in cancer metastases. Cancer metastases may decrease by about 5-100, 10-90, 20-80, 30-70, 40-60, 50-95, 65-85, or 75-95%. The decrease in cancer metastases may by at least 5, 10, 15, 20, 25, 30, 35, 40, 45, 50, 55, 60, 65, 70, 76, 80, 85, 90, 95, 99, or 100%. The decrease in cancer metastases may by at least 2%. The decrease in cancer metastases may by at least 5%. The decrease in cancer metastases may by at least 10%. The decrease in cancer metastases may by at least 30%. The decrease in cancer metastases may be by at least 50%.

Dengue Viruses

Provided herein are compositions for the treatment of cancer, wherein the composition comprises a Dengue virus in an effective amount for depletion or reduction of cancer in a subject in need thereof. Also provided herein are methods for treatment of cancer, comprising administering to a subject in need thereof, an effective amount of a Dengue virus for depletion or reduction of a cancer. Also provided herein are methods for the stabilization of cancer, comprising administering to a subject in need thereof, an effective amount of a Dengue virus for stabilizing or controlling growth of a cancer. Dengue viruses are Arboviruses, and are transmitted exclusively by mosquitoes of the *Aedes aegypti* and *albopictus* species. The virus has a complex life cycle involving an unidentified forest-dwelling mammalian reservoir (possibly primates), and human hosts. The female mosquito takes a blood meal from an infected person, the virus replicates to a high infectious titer ($10^5$/ml) in gut epithelial cells, then is transmitted to another person when the mosquito withdraws its stylet using back pressure after another blood meal. Dengue epidemics infect 50 million persons annually, with several thousand deaths, usually children with inadequate treatment of secondary infection-related shock.

Provided herein are methods for combination therapy comprising administering a Dengue virus (DV) and activated DCs disclosed herein to target tumor cells, wherein the DV is administered to a subject. As used herein, the term "Dengue virus" includes any serotype of Dengue virus serotypes 1, 2, 3, 4, or 5. The term Dengue virus may also encompass genetically modified DV, in vitro mutated DV, and combinations of DV or proteins/peptides thereof. The DV may be alive, dead, recombinant or a protein/peptide thereof.

In primary infections, the death rate from DV is very low (1 in 61,000 per Manson's Tropical Diseases). The virus infects, but does not kill APC of the monocyte-macrophage and Dendritic Cell lineage. These infected APC then begin a cytokine cascade of the pro-inflammatory (TNF-alpha and IL-1 beta), and TH1 (IL-2, IL-7, IL-12, IL-15, and IL-21) types. These cytokines may result in strong activation of both the adaptive (CTL) and innate (NK) immune systems. After a 3-5 day incubation period, the fever rises to 39.5-40.5° C., and remains elevated for 4-5 days. The subject experiences intense headache, joint pain, malaise, and sensitivity to light. A rash covering the chest, back, and sometimes legs and arms, may develop by day 3 of fever. Clinically, dengue infections result in lowered platelet counts leading to hemorrhage, which ranges from minor to life-threatening in case of shock syndrome. With proper supportive care based on judicious fluid management, recovery is complete in 99% of cases.

Dengue viruses are Arboviruses, and are transmitted exclusively by mosquitoes of the *Aedes aegypti* and *albopictus* species. The virus has a complex life cycle involving an unidentified forest-dwelling mammalian reservoir (possibly primates), and human hosts. The female mosquito takes a blood meal from an infected person, the virus replicates to a high infectious titer ($10^5$/ml), in gut epithelial cells, then is transmitted to another person when the mosquito withdraws its stylet using back pressure after another blood meal. Dengue epidemics infect 50 million persons annually, with several thousand deaths, usually children with inadequate treatment of secondary infection-related shock.

The Dengue virus genome encodes structural proteins, capsid protein C, membrane protein M, envelope protein E, and nonstructural proteins, NS1, NS2a, NS2b, NS3, NS4a, NS4b and NS5. In some instances, the Dengue virus is a live strain of the Dengue virus. In some instances, the Dengue virus is a non-attenuated strain of the Dengue virus. In some instances, the Dengue virus is an attenuated strain of the Dengue virus. In some instances, the Dengue virus is a weakened strain of the Dengue virus. In some instances, the Dengue virus is selected the following serotypes of dengue virus: DENV-1, DENV-2, DENV-3, DENV-4, and DENV-5, and combinations thereof.

Dengue Viruses are positive-strand RNA viruses of the Togavirus Family, sub-family Flaviviridae, (Group B). The virus has an icosahedral geometry and is approximately 40-45 nanometers in diameter. The 11,000 base genome codes for a nucleocapsid (NC), protein, a prM membrane fusion protein, an envelope glycoprotein (E), and 5 nonstructural proteins NS1-NS5. The NC protein forms the viral core, with the envelope spikes attached via the prM complex. The E glycoprotein is the main target of neutralizing antibodies, and the NS-3 and NS-4 proteins make up the main targets for CD4+ and CD8+CTL.

The Dengue viruses make up five distinct serotypes, DENV-1 through DENV-5. The serotypes 2 and 4 are cross-neutralizing for IgG, and types 1 and 3 are also cross-neutralizing. Immunity is not complete, however, and dengue is unique among viral infections in that a subsequent infection by a non-cross-neutralizing serotype carries an increased risk of mortality due to shock syndrome from immune hyper-activation. In some cases, a non-lethal form of a Dengue virus can be utilized. Exemplary non-lethal Dengue viruses can be of serotype 1, 2, 3, 4, or 5. For example, a non-lethal Dengue virus can be selected from Table 2. In some cases, a non-lethal Dengue Virus can be substantially similar to any strain of Table 2. For example a Dengue Virus can be from about 50%, 60%, 70%, 80%, 90%, 95%, 96%, 97%, 98%, 99%, or up to about 100% identical in sequence homology or structural homology to any strain of Table 2.

TABLE 2

Non-lethal Dengue Virus Strains

| Serotype | Strain |
|---|---|
| I | 45AZ5 |
| II | 1710 |
| II | S16803 |
| II | HON 1991 C |
| II | HON 1991 D |
| II | HON 1991 B |
| II | HON 1991 A |
| II | SAL 1987 |
| II | TRI 1981 |
| II | PR 1969 |
| II | IND 1957 |
| II | TRI 1953 |
| II | TSV01 |
| II | DS09-280106 |
| II | DS31-291005 |
| II | 1349 |
| II | GD01/03 |
| II | 44 |
| II | 43 |
| II | China 04 |
| II | FJ11/99 |
| II | FJ-10 |
| II | QHD13CAIQ |
| II | CO/BID-V3358 |
| II | FJ/UH21/1971 |
| II | GU/BID-V2950 |
| II | American Asian |
| II | GWL18 |
| II | IN/BID-V2961 |
| II | Od2112 |
| II | RR44 |
| II | 1392 |
| II | 1016DN |
| II | 1017DN |
| II | 1070DN |
| II | 98900663DHF |
| II | BA05i |
| II | 1022DN |
| II | NGC |
| II | Pak-L-2011 |
| II | Pak-K-2009 |
| II | Pak-M-2011 |
| II | PakL-2013 |
| II | Pak—L-2011 |
| II | Pak-L-2010 |
| II | Pak-L-2008 |
| II | PE/NFI1159 |
| II | PE/IQA 2080 |
| II | SG/D2Y98P-PP1 |
| II | SG/05K3295DK1 |
| II | LK/BID/V2421 |
| II | LK/BID-V2422 |
| II | LK/BID-V2416 |
| II | 1222-DF-06 |
| II | TW/BID-V5056 |
| II | TH/BID-V3357 |
| II | US/BID-V5412 |
| II | US/BID-V5055 |
| II | IQT1797 |
| II | VN/BID-V735 |
| II | US/Hawaii/1944 |
| III | CH53489 |
| IV | 341750 |

Provided herein are compositions and method using such compositions, wherein the composition comprises Dengue virus serotype 1, 2, 3, 4, or 5. In some instances, the DV is serotype 2. In some instances the DV serotype 2 is DENV-2 strain #1710. DENV-2 strain #1710 may be advantageous over other DV strains because it is milder at infecting subjects, and are therefore safer. Other more virulent strains may have a stronger anti-tumor effect, but they may not be suitable due to safety concerns. A more virulent strain, by way of non-limiting example, is DENV-2 strain #1584. The DENV-2 strain #1710 is from a sample taken from Puerto Rico in 1985 and characterized as type A from a restriction site specific RT-PCR analysis using 4 primers (see Table 3) specific to the envelope gene region. Restriction site specific RT-PCR with these primers produces amplification products of 582 base pairs, 754 base pairs, and possibly 676 base pairs. The DENV-2 strain #1710 is recorded in a CDC database as entry number 555. The DENV-2 strain #1710 was isolated during a Puerto Rican epidemic. This outbreak had 9,540 suspected cases of DV, with one suspected, but no confirmed deaths due to the virus, which indicates the toxicity of DEN-2 strain #1710 is very low and therefore suitable for the methods disclosed herein.

TABLE 3

Sequence and Position of Primers to Amplify DENV-2 #1710 Virus

| Primer | Sequence | Genome Position | Strand |
|---|---|---|---|
| RSS1 | 5'-GGATCCCAAGAAGGGGCCAT-3' (SEQ ID NO: 31) | 1696-1715 | + |
| RSS2 | 5'-GGCAGCTCCATAGATTGCT-3 (SEQ ID NO: 32) | 2277-2259 | − |
| RSS3 | 5'-GGTGTTGCTGCAGATGGAA-3' (SEQ ID NO: 33) | 1524-1542 | + |
| RSS4 | 5'-GTGTCACAGACAGTGAGGT-3' (SEQ ID NO: 34) | 2371-2353 | − |

Certain characteristics of DV and DV infection may make this virus particularly useful for the methods disclosed herein. For example, a unique feature of DV is that primary infections result in activation of a TH1-type response of CD4+ and CD8+ helper-inducer and cytotoxic-effector CTL. By infecting, but not killing the antigen presenting cell (APC), (e.g. dendritic cell), DV up-regulates CD80 and CD83 expression on the APC, resulting in a pro-inflammatory TH1 cytokine profile. Primary DV infections induce a TH1 type response with activated CD4+ and CD8+ effector T cells as well as lymphokine-activated killer cells. This may increase the likelihood of a complete response to a cancer immunotherapy, such as therapies utilizing the primed dendritic cells disclosed herein.

In some cases, Dengue viruses can provide a counter attack to a tumor immune evasion mechanism. The tumor immune evasion mechanism, by way of non-limiting example, may be low levels of MHC on the tumor cell to prevent CTL recognition, and the counter attack may be high Interferon-γ raising MHC levels by up-regulating MHC gene expression. The tumor immune evasion mechanism, also by way of non-limiting example, may be one or more point mutations in a tumor peptide to prevent TCR binding, and the counter attack may be stimulating lymphokine-activated killer cells or cytokine-induced killer cells to target "escaped" tumor cells expressing aberrant peptides or MHC. In some instances, the tumor immune evasion mechanism is tumor vessels lacking factors for CTL attachment and trafficking, and the counter attack is high TNF-α restores gaps by altering PECAM-1, restores ICAM-1/VCAM-1 expression and P and E-selectins. In some instances, the tumor immune evasion mechanism is FasL killing of Fas+ CTL by triggering apoptosis, and the counter attack is high IL-6 and/or IL-15] protects Fas+ CTL by up-regulating FLIP ligand. In some instances, the tumor immune evasion mechanism is HLA-G protects from NK Cells, and the counter attack may be high IL-2, IL-7, IL-12, and/or IL-15 raise activation of NK. The tumor immune evasion mechanism may be stromal barriers inhibit CTL and the counter attack may be high IFN-γ activates macrophages to M1. The tumor immune evasion mechanism may be Myeloid-Derived Suppressor Cells, (MDSC) and the counter attack may be iNKT Cells decrease MDSC. The tumor immune evasion mechanism may be CTL inactivated by TGF-β and the counter attack may be TH1 cytokines reactivate tolerant CTL. The tumor immune evasion mechanism may be Tumor PI-9 blocks CTL killing and the counter attack may be high CD8 & ICAM-1 expression restores low-avidity CTL recognition and lysis by stabilizing weak interactions between TCR and MHC+self-peptide. The tumor immune evasion mechanism may be T-regulatory cells block CTL and the counter attack may be high CD4 Helper cells overcome CD4 T Reg cells.

In some instances, the methods comprise activating or enhancing the subject's immune response by administering Dengue virus to the subject. Activating or enhancing may comprise inducing or increasing expression of cytokines and inflammatory mediators. Expression of genes in cells of the subject that may be increased by DV infection, include, but are not limited to, IL-1 beta, IL-2, IL-7, IL-12, IL-15, IFN-alpha, IFN-gamma, ICAM-1, TNF-alpha, TNF-beta, GM-CSF, CD8 antigen, ICOSLG, CCL3, CCL5, TRAIL, IP10, GNLY, MHC, HLA, GZMA, HLA-DRA, HLA-DP alpha1, HLA-DP beta 1, and ZAP70. In some instances, ICAM-1 up-regulation is mediated by TNFα, and can be utilized for cell-to-cell contact, i.e., CTL-to-tumor cell. This change is significant because ICAM-1 can be utilized for close CTL-to-tumor contact and lysis. ICAM-1 can increase the "stickiness" of tumor cells, to allow CTL to adhere to them and kill them. For example when a tumor cell is exposed to Dengue virus supernatant or Dengue virus, the tumor cell can up-regulate its ICAM-1 expression. Lack or low expression of ICAM-1 in immunosuppressed tumors is one of the challenges in CTL-based checkpoint inhibitors such as Ipilimumab and Nivolumab. Therefore, combination therapy utilizing Dengue virus in subjects having immunosuppressed tumors can improve therapy efficacy. In some cases, the use of Dengue virus can increase an ICAM-1 expression on a tumor by about 5%, 10%, 20%, 30%, 40%, 50%, 60%, 70%, 80%, 90% or up to about 100%. In some cases, the use of Dengue virus can increase an ICAM-1 expression on a tumor by about 5% to 20%, 25% to 35%, 30% to 55%, 40% to 65%, 50% to 75%, 60% to 85%, or 70% to 95%.

In some instances, the methods comprise activating or enhancing a subject's immune response by administering Dengue virus to a subject. A Dengue virus or Dengue virus supernatant can increase MHC or HLA expression on a tumor. MHC expressions are critical for CTL-based checkpoint inhibitors such as Ipilimumab and Nivolumab to establish CTL-to-tumor contact. For example, Dengue virus infection can increase Class I expression on resistant tumor cells, enabling CTL immunotherapy. Checkpoint inhibitors can work by delaying the "off" or "die" signals like CTLA-4 or PD-1 on CTLs. CTLs can utilize Class I MHC expression in order to identify and destroy tumor cells. Raising MHC expression on tumor targets allows the CTL to kill more effectively. This is especially important for activating anergic CTL clones, as the combination of increased CTL activation and restoration of Class I MHC expression is promising for clinical response potential. In some cases, the use of Dengue virus can increase an MHC or HLA expression on a tumor by about 5%, 10%, 20%, 30%, 40%, 50%, 60%, 70%, 80%, 90% or up to about 100%. In some cases, the use of Dengue virus can increase an MHC or HLA expression on a tumor by about 5% to 20%, 25% to 35%, 30% to 55%, 40% to 65%, 50% to 75%, 60% to 85%, or 70% to 95%.

Advantageous DV characteristics for use as a potent immune-stimulant in cancer immunotherapies are described herein. DV has affinity for immature B-lymphocytes and antigen-presenting cells (APC) of monocyte/macrophage and dendritic cell (DC) lineage. A unique feature of DV is that primary infections result in activation of a $T_H1$-type response of CD4+ and CD8+ helper-inducer and cytotoxic-effector CTL. By infecting, but not killing the APC, DV up-regulates their CD80 and CD83 expression, resulting in a pro-inflammatory $T_H1$ cytokine profile. Primary DV infections induce a $T_H1$ type response with activated $CD4^+$ and $CD8^+$ effector T cells as well as LAK cells. This type of response is seen in patients having complete responses to cancer immunotherapies (see Table 4).

TABLE 4

Tumor immune evasion mechanisms and DV infection

| Immune evasion | Dengue counter-attack |
|---|---|
| Low levels of MHC on tumor cell prevent CTL recognition | High Interferon-γ raises MHC levels by up-regulating MHC gene expression |
| Point mutations in Tumor Peptides prevent TCR binding | LAK/CIK cells target "escaped" tumor cells expressing aberrant peptides or MHC |
| Tumor vessels lack factors for CTL attachment and trafficking | Hi [TNF-α] restores gaps by altering PECAM-1, restores ICAM-1/VCAM-1 expression and P and E-selectins |
| FasL can kill $Fas^+$ CTL by triggering apoptosis | Hi [IL-6, 15] protects $Fas^+$ CTL by up-regulating FLIP ligand |
| HLA-G protects from NK Cells | Hi [IL-2, 7, 12, 15] raise activation of NK |
| Stromal barriers inhibit CTL | Hi [IFN-γ] activates Macrophages to $M_1$ |
| Myeloid-Derived Suppressor Cells, (MDSC) | iNKT Cells can decrease MDSC |

TABLE 4-continued Tumor immune evasion mechanisms and DV infection

| Immune evasion | Dengue counter-attack |
| --- | --- |
| CTL inactivated by TGF-β | $T_H 1$ cytokines reactivate tolerant CTL |
| Tumor PI-9 blocks CTL killing | Hi [CD8] & ICAM-1 expression can restore low-avidity CTL recognition and lysis by stabilizing weak interactions between TCR and MHC + self-peptide |
| T-regulatory cells block CTL | Hi $CD4^{Helper}$ cells overcome $CD4^{Reg}$ cells |

In some instances, the methods disclosed herein comprise administering DV to the subject, wherein the administering results in the release of TNF-α by the immune system. TNFα is an inflammatory cytokine with pleiotropic effects, including direct killing of tumor cells via TRAIL (TNF-Apoptosis-Inducing-Ligand). Increased levels of proteins corresponding to these genes may be observed in tissues and circulating fluids of the subject as well. Levels may be increased at least 2-fold. Levels may be increased between 2-fold and 1000-fold. Levels may be increased between 2-fold, 10-fold, 40-fold, 80-fold, 100-fold, 200-fold, 300-fold, 400-fold, 500-fold, 600-fold, 700-fold, 800-fold, 900-fold, and 1000-fold. Levels may be increased between 2-fold and 10-fold.

In some instances, administering DV induces high levels of soluble TRAIL (sTRAIL) from a variety of cells including γδCTL, activated M1 macrophages and plasmacytoid DC (pDC). In some instances, DV activates IFNβ, a multifunctional cytokine with a 10-fold higher affinity for the same receptor as IFNα. IFNβ has similar antiviral properties in suppressing transcription of viral RNA, but is much more potent than IFNα in inducing apoptosis in tumor cells. Nitric oxide and IFNβ could act in a synergistic fashion during dengue infection. These molecules may work in tandem to overcome resistance to apoptosis mediated by the high levels of sTRAIL induced by M1 macrophages, pDC, and δγ CTL.

Activating or enhancing the immune system of the subject may comprise inducing or increasing cell types present in the subject. These cell types include, but are not limited to, CD8+CD44+62L− cells, CD4+CD44+CD62Llo cells, HLA-DR+CD8+ cells, Tia-1 CD8+ cells, VLA-4 CD8+ cells, ICAM-1 CD8+ cells, and LFA-1 CD8+ cells.

Chikungunya Virus

Provided herein are methods for treating a condition or disease in a subject in need thereof comprising administering a Chikungunya virus to the subject. Chikungunya virus may be abbreviated herein as "CHK" or "CV," Chikungunya virus belongs to the alphavirus genus, and Togaviridae family. It is an RNA virus. Chikungunya virus may be related to Ross River virus, O'nyong'nyong virus, and Semliki Forest virus, which may provide alternative viruses used in methods provided herein. Chikungunya virus has a very low mortality rate, approximately 1:1000, the elderly being most likely to have severe complications. Further provided herein are methods for treating a subject in need thereof, comprising observing the subject for symptoms of a successful administration (e.g., infection). Symptoms may include onset of fever two to four days after exposure, headache, fatigue, digestive complaints, conjunctivitis, joint pains, abdominal pain, nausea, vomiting, diarrhea, and combinations thereof. Further provided herein are methods, wherein the CV induces a fever that is between 39° C. (102° F.) and 40° C. (104° F.). Symptoms may include a rash. In some cases, the rash may be a maculopapular rash. Further provided herein are methods comprising RT-PCR of CV specific nucleic acid sequences, or measurement of IgM levels in the blood serum (e.g., via ELISA) of the subject in order to ascertain an infection sufficient to have adjuvant effects with DC administration.

Further provided herein are methods for treating a condition or disease in a subject in need thereof, wherein the Chikungunya virus is an attenuated Chikungunya virus. The methods may comprise attenuating the Chikungunya virus. Attenuation of the original virus strain may be desirable or necessary, as a wild-type CHK strain may cause unacceptable toxicity: fever, hepatic and splenic lesions, internal hemorrhage, and most critical: crippling joint pain, which persists for months or years in up to 30% of CV infection cases. Attenuation is a process where an original virus strain is passaged in various cell lines, then progeny are analyzed for signs of attenuation: lower growth characteristics, less severe disease symptoms in mice, etc.

Further provided herein are methods, wherein the Chikungunya virus (CV) is attenuated to a strength capable of inducing a systemic immune response without severe symptoms. Severe symptoms may include fever, hepatic and splenic lesions, internal hemorrhage, and crippling joint pain. Attenuation may be carried out by serial passage of said virus in permissive cell lines. Attenuation may also be carried out by selective passage in live animals. Attenuation may result in a virus strain with desired properties for a systemic infection without overt Chikungunya symptoms. Systemic infection may be produced by injecting virus into a cancer patient. Systemic infection may be induced by injecting sufficient said virus into the patient to produce an immune activation. Immune activation of sufficient power may be required to activate CTL induced by aforementioned Dendritic Cells to overcome tumor immune evasions and kill tumor cells.

Provided herein are methods for administering a CV as part of a combination therapy, wherein the CV strain is an Asian strain, a West African strain or an East/Central/South African (ECSA) strain. The CV strain may be of the Indian Ocean Lineage (IOL). The CV strain may be found in or originate in Brazil. The Asian strain may be a strain found in patient sera from an Indonesia, Malaysia, Philippines, India, or Thailand epidemic. The West African strain may be a strain found in patient sera from a Nigeria, Senegal, or Cote d'Ivoire epidemic. The ECSA strain may be a strain found in patient sera from a South Africa, Tanzania, Congo, Angola, Reunion, Sri-Lanka, Central Africa, or Uganda epidemic. The CV strain may be CHK/SBY8/10 (Accession number AB678677). The CV strain may be TSI-GSD-218 (181/clone 25 V-181, Accession number L37661). The CV strain may be AF15561 (Accession number EF452493). The CV strain may be about 10% to about 90% less virulent than a strain selected from CHK/SBY8/10, TSI-GSD-218, and AF15561, as measured by plaque assay. The CV strain may be about 10% to about 90% more virulent than a strain selected from CHK/SBY8/10, TSI-GSD-218, and AF15561, as measured by plaque assay. Several CV strains have been isolated and sequenced. GenBank sequence accession numbers for genomes of known CV strains include HM045792, HM045795, HM045805, AF490259, HM045821, HM045806, HM045809, HM045822, JQ067624, HM045812, HM045784 and HM045823. GenBank sequence accession numbers for genomes of known Asian strains include HM045803, EF027140, HM045813, HM045788, EF027141, HM045810, HM045814, HM045808, HM045789, HM045802, HM045796, HM045787, HM045797, HM045791, HM045800, HM045790, HE806461, FN295483, FN295484, EU703762, EU703759, EU703760, EU703761, FJ807897, KF318729, KJ451623, KJ451622, CNR20236, CNR20235, and KJ451624. GenBank sequence accession for genomes of known IOL strains include: JF274082, EU372006, GU908223, FR717336, GQ428213, KJ796852, KJ796851, KJ796845, KC862329, FN295485, FN295487, GU189061, HQ456255, HQ456254, HQ456253, HQ456252, HQ456251. West African genotype: HM045816, HM045815, HM045798, HM045785, HM045786, HM045807, AY726732, HM045817, HM045820, HM045819, and HM045818. CV strains described herein may be assayed for cytopathic effects and further screened to confirm non-lethality prior to selection for a combination therapy described herein. In some instances, CV strains described herein are attenuated to a strength capable of inducing a systemic immune response without severe symptoms.

Cancer

Provided herein are methods for cancer therapy comprising administration of therapeutic agents disclosed herein. Methods described herein also provide for clearing cancer cells. In some instances, administering DV to the subject induces an immune response. In some instances, the immune response is potent as compared to a common virus, such as a common cold virus. In some instances, the immune response results in tumor regression. The methods disclosed herein may comprise developing DCs capable of inducing an immune response that results in eliminating all tumor cells in a subject's body.

DNA microarray analyses have revealed that hundreds of genetically distinct tumor clones may exist in a single subject with advanced tumor. There is a pattern of negative correlation between 02 supply and genetic mutation rates. The majority of agents such as cytotoxic drugs, antibodies, and small molecules, are nearly always blood-borne, exerting a Darwinian selective pressure to tumor clones that evade therapeutic mechanisms. Clones with the lowest perfusion rates have both low drug exposure and high capacity to evade immune system detection, making them resistant to conventional therapies. Provided herein are methods for cancer cell targeting, comprising inducing fever hyperthermia by administering DV to the subject with cancer, starving low-flow, resistant clones with mutated phenotypes, leaving more genetically stable clones for elimination by activated lymphocytes and other arms of the immune system. In some instances, the methods comprise combining fever with activation of CTL and lymphokine-activated killer cells (LAK) by administering pulsed DCs, lead to higher response rates than with conventional cancer therapies (e.g. antibody drug conjugates, kinase inhibitors, small molecules, etc.) or CTLs alone. The immune suppression seen in subjects with advanced cancer is a complex and dynamic process. It involves tolerance to the tumor antigens themselves, which are usually recognized as "self" by CTL. In some instances, methods described herein comprise breaking this tolerance and achieving high levels of TH1 cytokines, which DV infection induces.

Cancers targeted herein may be a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, sarcomas, carcinomas, lymphomas or leukemias. In some instances, the cancer is a solid tumor or a liposarcoma.

In some instances, the cancer is a sarcoma. The sarcomas may be a cancer of the bone, cartilage, fat, muscle, blood vessels, or other connective or supportive tissue. In some instances, sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma). The sarcoma may comprise a Ewing's sarcoma.

In some instances, the cancer is a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. In some instances, the cancer is bladder cancer.

In some instances, the cancer is a neuroendocrine cancer. In some instances, the cancer is a pancreatic cancer. In some instances, the cancer is thyroid cancer. In some instances, the cancer is an epithelial cancer, breast cancer, endometrial cancer, ovarian cancer, stromal ovarian cancer, or cervical cancer. In some instances, the cancer is prostate cancer. In some instances, the cancer is a skin cancer. In some instances, the cancer is a neo-angiogenic skin cancer. In some instances, the cancer is a melanoma. In some instances, the cancer is a kidney cancer, a lung cancer. Exemplary lung cancers include, without limitation, a small cell lung cancer or a non-small cell lung cancer. In some instances, the cancer is a colorectal cancer, e.g., a gastric cancer or a colon cancer. In some instance, the cancer is a brain cancer. In some instances, the cancer is a brain tumor. In some instances, the cancer is a glioblastoma or an astrocytoma.

In some instances, the cancer is breast cancer. In some cases, the breast cancer is a triple negative breast cancer (negative for estrogen receptor, progesterone receptor and Her2). In some cases, the breast cancer is estrogen receptor positive (ER+).

In some instances, the cancer is a lung cancer. In some instances, the lung cancer is a non-small cell lung carcinoma (NSCLC), small cell lung carcinoma, or mesotheliomia. Examples of NSCLC include squamous cell carcinoma, adenocarcinoma, and large cell carcinoma. In some instances, the mesothelioma is a cancerous tumor of the lining of the lung and chest cavity (pleura) or lining of the abdomen (peritoneum). In some instances, the mesothelioma is due to asbestos exposure.

In some instances, the cancer is a central nervous system (CNS) tumor. In some instances, the CNS tumor is classified as a glioma or nonglioma. In some instances, the glioma is malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

In some instances, the cancer is a blood cancer. In some instances, the cancer is leukemia. In some instances, the cancer is a myeloid leukemia. In some instances, the cancer is a lymphoma. In some instances, the cancer is a non-Hodgkin's lymphoma. In some instances, the cancer is selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. In some instance, the cancer is a hematological malignancy. In some instance, the hematological malignancy is a B cell malignancy. In some instance, the cancer is a chronic lymphocytic leukemia. In some instance, the cancer is an acute lymphoblastic leukemia. In some instance, the cancer is a CD19-positive Burkitt's lymphoma. In some instance, the leukemia is an acute lymphocytic leukemia, acute myelocytic leukemia, chronic lymphocytic leukemia, or chronic myelocytic leukemia. Additional types of leukemias include, but are not limited to, hairy cell leukemia, chronic myelomonocytic leukemia, and juvenile myelomonocytic leukemia.

In some instances, the lymphoma develops from a B lymphocyte or T lymphocyte. Two major types of lymphoma are Hodgkin's lymphoma, previously known as Hodgkin's disease, and non-Hodgkin's lymphoma. In some instance, the Non-Hodgkin lymphoma is indolent. In some instance, the Non-Hodgkin lymphoma is aggressive. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Methods of Administration

Provided herein are methods for treatment of a condition in a subject comprising administering cells disclosed herein. The methods may comprise administering DC. The methods may comprise administering DCs after pulsing the DCs, without storing or shipping the DCs. The methods may comprise administering the DCs after storing or shipping the DCs. The methods may comprise administering DCs at a time point selected from about 1 hour to about 24 hours after pulsing the DC. The methods may comprise administering the DCs at a time point selected from about 1 day to about 30 days after pulsing the DCs. The methods may comprise administering the DCs at a time point selected from about 1 week to about 12 weeks after pulsing the DCs.

Provided herein are methods for treatment of a condition in a subject comprising administering DCs to a subject in need thereof. In some instances, the DCs are provided in a solution. In some instances, the DCs are administered by a route selected from subcutaneous injection, intramuscular injection, intradermal injection, percutaneous administration, intravenous ("i.v.") administration, intranasal administration, intralymphatic injection, and oral administration. In some cases, iv administration is preferable, eliciting a more desirable response than other forms of administration (e.g. subcutaneous injection). In some instances, the subject is infused with the DC by an intralymphatic microcatheter.

Methods described herein may comprise suspending or mixing cells in a solution for intravenous (i.v.) administration (e.g., a 0.9% NaCL solution). The i.v. DCs may traffic to the lungs, where some will be trapped, but the majority may pass to secondary lymphatic organs such as liver and spleen white pulp T-cell zones to prime the CTL.

In some instances, the Dengue virus is initially administered at least 24 hours before administering the dendritic cells. In some instances, the Dengue virus is initially administered between about 12 hours and about 96 hours before administering the dendritic cells. In some instances, the Dengue virus is initially administered between about 24 hours and about 72 hours before administering the primed dendritic cells. In some instances, the Dengue virus is initially administered between 1 day and 4 days before administering the primed dendritic cells. In some instances, the Dengue virus is administered only once. In some instances, the Dengue virus is administered more than once. In some instances, the Dengue virus is administered only before receiving dendritic cells. In some instances, the Dengue virus is administered after receiving the primed dendritic cells. In some instances, the Dengue virus is administered before and after receiving the primed dendritic cells.

The methods may comprise administering primed DCs on Day 0, followed by two injection of virus, such that the entire treatment is conducted in a week or less. In some instances, the subject will only receive the entire treatment once. In some instances, the entire treatment is repeated not more than once. In some cases, the entire treatment is repeated not more than twice. In some instances, the entire treatment is repeated not more than three times. In some cases, the entire treatment is repeated not more than ten times.

In some cases, the methods comprise administering the Dengue virus at a dose of about 0.5 ml of $10^6$ pfu/ml. In some instances, the dose is between about $10^3$ pfu/ml and about $10^8$ pfu/ml. In some instances, the dose is between about $10^3$ pfu/ml and about $10^6$ pfu/ml. In some instances, the dose is between about $10^3$ pfu/ml to about $10^4$ pfu/ml, between about $10^4$ pfu/ml to about $10^6$ pfu/ml, between about $10^6$ pfu/ml to about $10^8$ pfu/ml, or between about $10^8$ pfu/ml to about $10^{10}$ pfu/ml. In some instances, the dose is from about $10^1$ pfu/ml, $10^2$ pfu/ml, $10^3$ pfu/ml, $10^4$ pfu/ml, $10^5$ pfu/ml, $10^6$ pfu/ml, $10^7$ pfu/ml, $10^8$ pfu/ml, or up to about $10^9$ pfu/ml. In some instances, a dose described herein is in a volume of about 0.01, 0.02, 0.03, 0.04, 0.05, 0.1, 0.2 ml or 0.3 ml. In some instances, a dose is in a volume of about 0.01 ml to about 0.03 ml, 0.03 ml to about 0.05 ml, 0.05 ml to about 0.07 ml, 0.07 ml to about 0.09 ml, 0.1 ml to about 0.2 ml, 0.2 ml to about 0.4 ml, 0.4 ml to about 0.6 ml.

In some instances, the methods disclosed herein comprise administering Dengue virus at a dose of about 0.5 ml of $10^6$ pfu/ml per day. In some instances, the dose is between about $10^3$ pfu/ml/day and about $10^8$ pfu/ml/day. In some instances, the dose is between about $10^3$ pfu/ml/day and about $10^6$ pfu/ml/day. In some instances, the methods disclosed herein comprise administering Dengue virus at more than one dose of about 0.5 ml of $10^6$ pfu/ml per day. In some instances, methods comprise administering a dose between about $10^3$ pfu/ml and about $10^8$ pfu/ml more than once per day. In some instances, methods comprise administering a dose between about $10^3$ pfu/ml and about $10^6$ pfu/ml more than once per day. In some instances, methods comprise administering a dose between about $10^3$ pfu/ml and about $10^8$ pfu/ml one to five times per day. In some instances, methods comprise administering a dose between about $10^3$ pfu/ml and about $10^6$ pfu/ml one to five times per day. In some instances, methods comprise administering a dose between about $10^3$ pfu/ml and about $10^8$ pfu/ml one to three times per day. In some instances, methods comprise administering a dose between about $10^3$ pfu/ml and about $10^6$ pfu/ml one to three times per day.

In some instances, the methods disclosed herein comprise administering Dengue virus at a dose of about 0.5 ml of $10^6$ pfu/ml per day. In some instances, the dose is between about $10^3$ pfu/ml/day and about $10^8$ pfu/ml/day. In some instances, the dose is between about $10^3$ pfu/ml/day and about $10^6$ pfu/ml/day. In some instances, the methods disclosed herein comprise administering Dengue virus at more than one dose of about 0.5 ml of $10^6$ pfu/ml per day. In some instances, methods comprise administering a dose between about $10^3$ pfu/ml and about $10^8$ pfu/ml more than once per day. In some instances, methods comprise administering a dose between about $10^3$ pfu/ml and about $10^6$ pfu/ml more than once per day. In some instances, methods comprise administering a dose between about $10^3$ pfu/ml and about $10^8$ pfu/ml one to five times per day. In some instances, methods comprise administering a dose between about $10^3$ pfu/ml and about $10^6$ pfu/ml one to five times per day. In some instances, methods comprise administering a dose between about $10^3$ pfu/ml and about $10^8$ pfu/ml one to three times per day. In some instances, methods comprise administering a dose between about $10^3$ pfu/ml and about $10^6$ pfu/ml one to three times per day.

Provided herein are methods comprising administering a composition comprising Dengue virus to a subject in need thereof. In some instances, the composition comprises a sugar. In some instances, the composition comprises a surfactant. In some instances, the composition comprises a protein. In some instances, the composition comprises a salt. In some instances, the composition comprises a non-ionic surfactant, a non-reducing sugar, a salt, a carrier protein, or a combination thereof. In some instances, the composition comprises a non-ionic surfactant. In some instances, the non-ionic surfactant is a non-ionic detergent. In some instances, the non-ionic surfactant is an agent comprising a hydrophobic chain. In some instances, the non-ionic surfactant is an agent comprising polyoxyethylene. In some instances, the non-ionic surfactant is an agent comprising polyoxypropylene. In some instances, the non-ionic surfactant is an agent comprising a polyoxyethylene-polyoxypropylene block copolymer. In some instances, the non-ionic surfactant is an agent that acts as a stabilizer of a cell membrane. In some instances, the non-ionic surfactant is an agent that protects from cell membrane shearing. In some instances, the non-ionic surfactant is an agent that acts as an anti-foaming agent. In some instances, the non-ionic surfactant comprises pluronic F-68. In some instances, the non-ionic surfactant consists essentially of pluronic F-68. Additional non-limiting examples of non-ionic surfactants contemplated for use in the compositions disclosed herein include alkyl polyglycoside, cetomacrogol 1000, cetostearyl alcohol, cetyl alcohol, cocamide DEA, cocamide MEA, decyl glucoside, decyl polyglucose, glycerol monostearate, IGEPAL CA-630, isoceteth-20, lauryl glucoside, maltosides, monolaurin, mycosubtilin, narrow-range ethoxylate, nonidet P-40, nonoxynol-9, nonoxynols, NP-40, octaethylene glycol monododecyl ether, N-octyl beta-d-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80, and combinations thereof. In some instances, the non-ionic surfactant is present in the composition at a concentration of about 0.01% w/v to about 10% w/v. In some instances, the non-ionic surfactant is present in the composition at a concentration of about 0.1% w/v to about 5% w/v. In some instances, the non-ionic surfactant is present in the composition at a concentration of about 1% w/v to about 5% w/v. In some instances, the non-ionic surfactant is present in the composition at a concentration of about 2% w/v.

Provided herein are methods comprising administering a composition comprising Dengue virus to a subject in need thereof. In some instances, the composition comprises a non-reducing sugar. In some instances, the non-reducing sugar is a sugar capable of trapping water molecules. In some instances, the non-reducing sugar acts as a cryoprotectant, protecting the viability of the Dengue virus during freezing and thawing. In some instances, the non-reducing sugar comprises a disaccharide. In some instances, the non-reducing sugar comprises an alpha, alpha-1, 1-glucoside bond between two alpha glucose units. In some instances, the non-reducing sugar consists essentially of a disaccharide. In some instances, the non-reducing sugar comprises a trehalose. Trehalose is also known as α-D-glucopyranosyl-(1→1)-α-D-glucopyranoside, mycose, and tremalose. In some embodiments, the non-reducing sugar consists essentially of a trehalose. In some instances, the trehalose is alpha-trehalose. In some instances, the trehalose is D-(+)-Trehalose dehydrate. In some instances, the trehalose has the chemical formula of $C_{12}H_{22}O_{11}\cdot 2H_2O$. In some instances, the non-reducing sugar is present in the composition at a concentration of about 5% w/v to about 25% w/v. In some instances, the non-reducing sugar is present in the composition at a concentration of about 1% w/v to about 10% w/v. In some instances, the non-reducing sugar is present in the composition at a concentration of about 10% w/v to about 20% w/v. In some instances, the non-reducing sugar is present in the composition at a concentration of about 15% w/v.

Provided herein are methods comprising administering a composition comprising Dengue virus to a subject in need thereof. In some instances, the composition comprises a carrier protein. Carrier proteins may function as a carrier or stabilizer for steroids, fatty acids, or hormones. In some instances, the carrier protein is a protein capable of stabilizing a virus envelope in storage conditions (e.g., below room temperature). In some instances, the carrier protein is a soluble monomeric protein. In some instances, the carrier protein is albumin. In some instances, the carrier protein is a human protein ensuring compositions disclosed herein are compliant with good manufacturing protocol (GMP) standard. In some instances the carrier protein is human albumin. In some instances, the carrier protein is present in the composition at a concentration of about 0.1% w/v to about 10% w/v. In some instances, the carrier protein is present in the composition at a concentration of about 1% w/v to about 5% w/v. In some instances, the carrier protein is present in the composition at a concentration of about 2% w/v.

Provided herein are methods comprising administering a composition comprising Dengue virus to a subject in need thereof. In some instances, the salt comprises calcium, magnesium, potassium, sodium, boron. In some instances, the salt is a phosphate salt, a chloride salt, a sulfate salt or a dichromate salt. In some instances, the salt is calcium chloride. In some instances, the salt is magnesium chloride. In some instances, compositions comprise calcium chloride and magnesium chloride. In some instances, the salt is present in the composition at a concentration of about 0.1 mM to about 10 mM. In some instances, the salt is present in the composition at a concentration of about 0.1 mM to about 5 mM. In some instances, the salt is present in the composition at a concentration of about 0.1 mM to about 2 mM. In some instances, the salt is present in the composition at a concentration of about 1 mM. In some instances, compositions comprise calcium chloride and magnesium chloride wherein calcium chloride is present in the composition at about 0.1 mM to about 10 mM, and magnesium chloride is present in the composition at about 0.1 mM to about 10 mM. In some instances, compositions comprise calcium chloride and magnesium chloride wherein calcium chloride is present in the composition at about 1 mM, and magnesium chloride is present in the composition at about 1 mM.

Provided herein are methods comprising administering an effective amount of Dengue virus disclosed herein to a subject in need thereof. In some instances, the effective amount is an amount sufficient to increase a level of at least one cytokine in the subject. In some instances, the effective amount is an amount sufficient to increase a level of at least one cytokine in the blood of the subject. In some instances, the effective amount is an amount sufficient to increase a level of at least one cytokine in a serum sample of the subject. In some instances, the effective amount is an amount sufficient to significantly increase the level of the at least one cytokine. In some instances, the effective amount is an amount sufficient to increase the level of the at least one cytokine by about 2% to about 20,000%. In some instances, the effective amount is an amount sufficient to increase the level of the at least one cytokine by about 50% to about 20,000%. In some instances, the effective amount is an amount sufficient to increase the level of the at least one cytokine by about 100% to about 20,000%. In some instances, the effective amount is an amount sufficient to increase the level of the at least one cytokine by about 100% to about 15,000%. In some instances, the effective amount is an amount sufficient to increase the level of the at least one cytokine by about 100% to about $1^4$,000%. In some instances, the effective amount is an amount sufficient to increase the level of the at least one cytokine by about 50% to about 15,000%. In some instances, the effective amount is an amount sufficient to increase the level of the at least one cytokine by about 50% to about 14,000%.

Provided herein are methods comprising administering an effective amount of Dengue virus disclosed herein to a subject in need thereof. In some instances, the effective amount is an amount sufficient to increase a level of at least one cytokine in the subject. In some instances, the at least one cytokine is an interleukin (IL). In some instances, the at least one cytokine is an interferon (IFN). In some instances, the at least one cytokine is an interleukin. In some instances, the at least one cytokine is selected from tumor necrosis factor (TNF) alpha, IFN alpha, IFN beta, IFN gamma, interferon gamma induced protein 10 (IP-10), IL-12, IL-2R, IL-7, IL-15, granulocyte macrophage colony stimulating factor (GM-CSF), and a combination thereof. In some instances the level of TNF alpha is increased from about 50% to about 500%. In some instances the level of TNF alpha is increased from about 50% to about 300%. In some instances the level of TNF alpha is increased from about 50% to about 240%. In some instances the level of IFN alpha is increased from about 50% to about 800%. In some instances the level of IFN alpha is increased from about 50% to about 500%. In some instances the level of IFN alpha is increased from about 50% to about 420%. In some instances the level of IFN beta is increased from about 50% to about 20,000%. In some instances the level of IFN beta is increased from about 50% to about 14,000%. In some instances the level of IFN gamma is increased from about 50% to about 200%. In some instances the level of IFN gamma is increased from about 50% to about 100%. In some instances the level of IP-10 is increased from about 50% to about 8000%. In some instances the level of IP-10 is increased from about 50% to about 5000%. In some instances the level of IP-10 is increased from about 50% to about 4000%. In some instances the level of IL-12 is increased from about 20% to about 200%. In some instances the level of IL-12 is increased from about 20% to about 100%. In some instances the level of IL-12 is increased from about 20% to about 80%. In some instances the level of IL-15 is increased from about 20% to about 200%. In some instances the level of IL-15 is increased from about 20% to about 200%. In some instances the level of IL-15 is increased from about 20% to about 100%. In some instances the level of IL-7 is increased from about 50% to about 1000%. In some instances the level of IL-7 is increased from about 50% to about 1000%. In some instances the level of IL-7 is increased from about 50% to about 500%. In some instances the level of GM-CSF is increased from about 50% to about 1000%. In some instances the level of GM-CSF is increased from about 50% to about 400%. In some instances the level of GM-CSF is increased from about 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, to about 350%. In some instances the level of IL-12R is increased from about 20%, 30%, 40%, 50%, 60%, 70%, 80%, 90%, 100%, 110%, 120%, 130%, 140%, 150%, 160%, 170%, 180%, 190%, to about 200%. In some instances the level of IL-12R is increased from about 20%, 30%, 40%, 50%, 60%, 70%, 80%, 90%, 100%, 110%, 120%, 130%, 140%, 150%, 160%, 170%, 180%, 190%, up to about 200% Provided herein are methods comprising administering an effective amount of Dengue virus disclosed herein to a subject in need thereof. In some instances, the effective amount is an amount sufficient to increase a level of at least one cytokine in the subject.

In some instances, successful infection or inoculation of the subject with the Dengue virus is confirmed by the development of hyperthermia or fever. In some instances, successful infection or inoculation of the subject with the Dengue virus is confirmed by the presence or increase of circulating cytokines in the blood/plasma of the subject. Cytokines may include, but are not limited to, interleukin-2 and interferon-gamma.

In some instances, methods described herein comprise administering primed dendritic cells to a subject in need thereof only once. In some instances, the primed dendritic cells are administered more than once. In some instances, the primed dendritic cells are administered a first time and a second time, wherein the first time and the second time are separated by about 1 day, about 2 days, about 3 days, about 4 days, about 5 days, or about 6 days, about 8 days, about 10 days, about 12 days, or about 18 days. In some instances, the first time and the second time are separated by about 1 week, about 2 weeks, about 3 weeks, or about a month. In some instances, the first time and the second time are separated by more than a month. In some instances, the first time and the second time are separated by less than 12 months. In some instances, the first time and the second time are separated by more than 12 months.

In some instances, methods described herein provide for administering primed dendritic cells to a subject when the subject is hyperthermic. In some instances, primed dendritic cells are administered after the subject has spiked a fever. In some instances, primed dendritic cells are administered after the subject's temperature has risen to between about 37.5° C. and about 42° C. In some instances, the primed dendritic cells are administered after the subject's temperature has risen to between about 38° C. and about 42° C. In some instances, the primed dendritic cells are administered after the subject's temperature has risen to at least about 38.5° C. In some instances, the primed dendritic cells are administered after the subject's temperature has risen to 38.5° C. In some instances, the primed dendritic cells are administered to the subject after the subject's temperature reaches 38 degrees Celsius or higher. In some instances, the subject's temperature is measured by a tympanic or oral method.

Methods for producing primed DC described herein may comprise activating T cells in vitro with the DCs produced by the methods disclosed herein. In some instances, the subject is incapable of mounting an effective immune response. For example, the subject may be immunocompromised. The subject may have received a therapy that renders them immunocompromised. The subject may have a disease that renders them immunocompromised. In this case, the methods may comprise contacting T cells from an HLA-matched subject with the DCs. Contacting the T cells with the DCs in vitro may induce a CTL response. Contacting the T cells with the DCs in vitro may also induce proliferation of the T cells.

Provided herein are pharmaceutical compositions comprising more than one strain of Dengue virus. In some instances, the pharmaceutical compositions comprise at least a portion of a Dengue virus. The portion of the Dengue virus may be a portion sufficient to generate an immune response in a subject receiving the pharmaceutical composition. The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

In some instances, the carriers disclosed herein comprise neutral buffered saline. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5.

Provided herein are compositions that comprise a Dengue virus, wherein the composition is in liquid form, lyophilized form or freeze-dried form and may include one or more lyoprotectants, excipients, surfactants, high molecular weight structural additives and/or bulking agents. In some instances, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the virus upon lyophilization. Exemplary lyoprotectant concentrations for sugars (e.g., sucrose, lactose, trehalose) in the pre-lyophilized formulation are from about 10 mM to about 400 mM.

Provided herein are compositions that comprise a Dengue virus disclosed herein, wherein the compositions are suitable for injection or infusion. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Devices for injection of a Dengue Virus described herein may be configured for subcutaneous injection. In some instances, the device is not configured for intradermal injection. The device may have a needle gauge size of 30 to 19 G on an ISO scale. The device may have a needle gauge size of 27 to 19 G on an ISO scale. The device may have a needle gauge size of 24 to 19 G on an ISO scale. The device may have a needle gauge size of 23 to 19 G on an ISO scale. The device may have a needle gauge size of 22 to 19 G on an ISO scale. The device may have a needle gauge size of 21 to 19 G on an ISO scale. The device may have a needle length of ⅜ inches to ¾ inches. The device may have a needle length of ½ inches to ⅝ inches. The needle may be injected at an angle of 45 degrees to 90 degrees for subcutaneous injection. The injection site may be in the deltoid muscle of arm, or vastus lateralis muscle of thigh.

Disclosed herein, are methods of manufacturing and storing the DV. In some instances, the DV is stored in a 0.5 ml container. In some instances, the DV is stored in a 1.0 ml container. In some instances, the DV is stored in a 1.5 ml container. In some instances, the DV is stored in a 2.0 ml container. In some instances, the DV is stored in a 2.5 ml container. In some instances, the DV is stored in a 3.0 ml container. In some instances, the DV is stored in a 3.5 ml container. In some instances, the DV is stored in a 4.0 ml container. In some instances, the DV is stored in a 4.5 ml container. In some instances, the DV is stored in a 5.0 ml container. In some instances, the DV is stored in a 5.5 ml container. In some instances, the DV is stored in a 6.0 ml container. In some instances, the DV is stored in a 6.5 ml container. In some instances, the DV is stored in a 7.0 ml container. In some instances, the DV is stored in a 7.5 ml container. In some instances, the DV is stored in an 8.0 ml container. In some instances, the DV is stored in an 8.5 ml container. In some instances, the DV is stored in a 9.0 ml container. In some instances, the DV is stored in a 9.5 ml container. In some instances, the DV is stored in a 10 ml container. Exemplary containers include, without limitation, a bottle, vial, can, or syringe.

Provided herein are pharmaceutical compositions that comprise a Dengue virus disclosed herein, and a non-aqueous solvent. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like.

Provided herein are pharmaceutical compositions that comprise a Dengue virus disclosed herein, wherein the pharmaceutical composition is formulated for inhalation, such as for example, as a dry powder. Suitable and/or preferred pharmaceutical formulations may be determined in view of the present disclosure and general knowledge of formulation technology, depending upon the intended route of administration, delivery format, and desired dosage.

Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

Kits

Disclosed herein can be kits comprising Dengue Virus compositions. Disclosed herein can also be kits for the treatment or prevention of a cancer, pathogen infection, or immune disorder. In some cases, a kit can include a therapeutic or prophylactic composition containing an effective amount of a composition of Dengue virus in unit dosage form and/or an effective amount of a checkpoint inhibitor. In some cases, a kit comprises a sterile container which can contain a therapeutic composition of Dengue virus; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some cases, a kit can include cells, such as dendritic cells, from about $1 \times 10^4$ cells to about $1 \times 10^{12}$ cells. In some cases a kit can include at least about $1 \times 10^5$ cells, at least about $1 \times 10^6$ cells, at least about $1 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^1$ cells, at least about $3 \times 10^{11}$ cells, at least about $4 \times 10^1$ cells, at least about $5 \times 10^{11}$ cells, at least about $6 \times 10^{11}$ cells, at least about $6 \times 10^1$ cells, at least about $8 \times 10^{11}$ cells, at least about $9 \times 10^1$ cells, or at least about $1 \times 10^{12}$ cells. For example, about $5 \times 10^{10}$ cells can be included in a kit. In another example, a kit can include $3 \times 10^6$ cells; the cells can be expanded to about $5 \times 10^{10}$ cells and administered to a subject. Such kits can further comprise instructions for use thereof.

Definitions

As used herein, the term "effective amount" or "therapeutic effective amount" refers to the amount of a compound described herein that is sufficient to effect the intended application including but not limited to disease treatment, as defined below. The therapeutically effective amount may vary depending upon the intended application (in vitro or in vivo), or the subject being treated, e.g., the weight and age of the subject, the severity of the disease condition, the manner of administration and the like, which can readily be determined by one of ordinary skill in the art. The specific dose will vary depending on the particular compounds chosen, the dosing regimen to be followed, whether it is administered in combination with Dengue virus, timing of administration, or the physical delivery system in which it is carried.

As used herein, "treatment" or "treating" is used interchangeably herein. These terms refer to an approach for obtaining beneficial or desired results including but not limited to therapeutic benefit and/or a prophylactic benefit. By therapeutic benefit is meant reduction, eradication or amelioration of the underlying disorder being treated. Also, a therapeutic benefit is achieved with the reduction eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "co-administration," "administered in combination with," and their grammatical equivalents, as used herein, encompass administration of two or more agents to an animal so that both agents are present in the animal at the same time. Co-administration includes simultaneous administration in separate compositions, administration at different times in separate compositions, or administration in a composition in which both agents are present.

The term "inhibitor" refers to a compound having the ability to inhibit a biological function of a target protein, whether by inhibiting the activity or expression of the target protein. Accordingly, the term "inhibitor" is defined in the context of the biological role of the target protein.

As used herein, "agent" or "therapeutic agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

As used herein, the term "antibody" is an immunoglobulin molecule capable of specific binding to a target, such as a carbohydrate, polynucleotide, lipid, and polypeptide through at least one antigen recognition site, located in the variable region of the immunoglobulin molecule. As used herein, the term encompasses not only intact polyclonal or monoclonal antibodies but also fragments thereof (such as Fab, Fab', F(ab')2, Fv), single chain (ScFv), mutants thereof, fusion proteins comprising an antibody portion (such as domain antibodies), synthetic antibodies, multi-specific antibodies, human antibodies, humanized antibodies, chimeric antibodies, single chain antibodies, and any other modified configuration of the immunoglobulin molecule that comprises an antigen recognition site. An antibody includes an antibody of any type of class, such as IgG, IgA, or IgM (or sub-class thereof), and the antibody need not be of any particular class. An antibody can be from any animal origin.

The term "subject" as used herein includes to mammals. Mammals include rats, mice, non-human primates, and primates, including humans.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

EXAMPLES

Example 1. Generation and Pulsing of Murine Dendritic Cells (DC)

A method as described by Lutz M., et. al. (J. Immunol. Methods 223:77-92, 1999), was employed to generate mature DCs form mouse bone marrow. Bone marrow suspensions were incubated in petri dishes in medium supplemented with recombinant murine GM-CSF for 10 days. Non-adherent cells were collected, centrifuged and resuspended in medium containing GM-CSF and lipopolysaccharide. Two days later, the DCs were harvested and their viability was determined by trypan-blue exclusion. Purity of the DCs was determined by flow cytometry analysis. DCs were pulsed with the synthetic peptides at 10 µg/ml for 18 hours. After 18 hours of incubation, DCs were harvested, washed twice in HBSS, and resuspended in HESS for additional studies (see Example 2 and 3).

Example 2. Dengue Virus and Dendritic Cells for the Treatment of Melanoma in a First Mouse Model A mouse model assay was performed to observe results from combination targeting of cancer cells using a Dengue virus (DV) strain and tumor antigen primed dendritic cells (DCs). DV C57BL/6 mice were inoculated with 0.05 ml of Dengue virus (DEN-2 strain #1710) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 (rIL-2) and 500 1U (rIFN-gamma) on days 5, 10, 15, and 20 following administration of Dengue virus (DEN-2 strain #1710, CDC database entry number 555, provided by Dr. Duane Gubler). Seven days after the Dengue virus administration, C57BL/6 mice were immunized with mouse DCs incubated with the 2 peptides separately and injected intravenously. Peptides were synthesized. The H-2b-restricted peptide from Ovalbumin (OVA-8), SIINFEKL (SEQ ID NO: 30), was used as a control. B16 melanoma-associated H-2b-restricted peptides derived from the antigens gp100/pme117 (EGSRNQDWL (SEQ ID NO: 28)) and from TRP-1/75 (TAYRYHLL (SEQ ID NO: 29)) were used to pulse murine DCs (see Example 1 for details). Two additional immunizations with DCs were given at 14-day intervals. Three days after the last DC infusion, mice were challenged with $5\times10^4$ viable B16 melanoma cells intravenously in the lateral tail vein and then followed for survival, which was recorded as the percentage of surviving animals over time (in days) after tumor injection. Data was recorded from five or more mice/group (see Table 5).

Example 3. Dengue Virus and Dendritic Cells for the Treatment of Melanoma in a Second Mouse Model A mouse model assay was performed to observe results from combination targeting of cancer cells using a Dengue virus (DV) strain and tumor antigen primed dendritic cells (DCs). Mice were administered cytokines to parallel the response to DV observed in humans.

Tumors were established in mice using the H-2b-restricted B16 murine melanoma cells line (ATCC #CRL-6322). Peptides (B16 melanoma associated H-2b-restricted peptides derived from antigens gp100/pme117 and from TRP-1/gp75) used for pulsing the dendritic cells were synthesized. Dendritic cells were generated from mouse bone marrow according to methods as described in Lutz et al. (J. Immunol. Methods 223:77-92, 1999).

On day 0, mice received $5\times10^4$ viable B16 melanoma cells intravenously in the lateral tail vein to establish pulmonary metastases. On day 7, the mice were inoculated with 0.05 ml of Dengue virus (DEN-2 strain #1710, CDC database entry number 555) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 1U (rIL-2) and 500 1U (rIFN-gamma) at 5-day intervals following administration of Dengue virus (DEN-2 strain #1710). On days 21, 35 and 49, the mouse DCs were incubated with the 2 peptides separately and injected intravenously in 2 sequential administrations on the same day to match the route and schedule of administration in subjects (see Example 2 for additional details). Control groups of mice received no Dengue virus or mice in Group 1, administered the tumor peptide primed DCs without the Dengue virus.

TABLE 5

Conditions for Dengue virus and dendritic cells for the treatment of melanoma

| Condition | Group | MOUSE ID | NO. OF LUNG METASTASES | Mean |
|---|---|---|---|---|
| $DV10^6$ pfu/ml + $2 \times 10^6$ DCs pulsed with gp100/TRP2 | 2 | II-2-1 | 55 | |
| $DV10^6$ pfu/ml + $2 \times 10^6$ DCs pulsed with gp100/TRP2 | 2 | II-2-2 | 68 | |
| $DV10^6$ pfu/ml + $2 \times 10^6$ DCs pulsed with gp100/TRP2 | 2 | II-2-3 | 57 | |
| $DV10^6$ pfu/ml + $2 \times 10^6$ DCs pulsed with gp100/TRP2 | 2 | II-2-4 | 62 | |
| $DV10^6$ pfu/ml + $2 \times 10^6$ DCs pulsed with gp100/TRP2 | 2 | II-2-5 | 52 | 58.8 |
| No DV + $2 \times 10^6$ DCs pulsed with gp100/TRP2 | 1 | II-1-1 | 58 | |
| No DV + $2 \times 10^6$ D DCs C pulsed with gp100/TRP2 | 1 | II-1-2 | 62 | |
| No DV + $2 \times 10^6$ DCs pulsed with gp100/TRP2 | 1 | II-1-3 | 66 | |
| No DV + $2 \times 10^6$ DCs pulsed with gp100/TRP2 | 1 | II-1-4 | 72 | |
| No DV + $2 \times 10^6$ DCs pulsed with gp100/TRP2 | 1 | II-1-5 | 60 | 63.6 |

The number of lung metastases observed in mice administered in Group 2 (Dengue Virus serotype 2 strain #1710 and tumor peptide primed DCs) was 7.5% lower than control dendritic cells pulsed with H-2b-restricted peptide from ovalbumin (OVA-8), SIINFEKL. Treatment and control groups are shown in Table 6.

TABLE 6

Conditions for Dengue virus and dendritic cells for the treatment of melanoma

| Condition | Group | MOUSE ID | NO. OF LUNG METASTASES | Mean |
|---|---|---|---|---|
| DV$10^6$ pfu/ml + 2 × $10^6$ DCs pulsed with gp100/TRP2 | 2 | II-2-1 | 55 | |
| DV$10^6$ pfu/ml + 2 × $10^6$ DCs pulsed with gp100/TRP2 | 2 | II-2-2 | 68 | |
| DV$10^6$ pfu/ml + 2 × $10^6$ DCs pulsed with gp100/TRP2 | 2 | II-2-3 | 57 | |
| DV$10^6$ pfu/ml + 2 × $10^6$ DCs pulsed with gp100/TRP2 | 2 | II-2-4 | 62 | |
| DV$10^6$ pfu/ml + 2 × $10^6$ DCs pulsed with gp100/TRP2 | 2 | II-2-5 | 52 | 58.8 |
| No DV + 2 × $10^6$ DCs pulsed with gp100/TRP2 | 1 | II-1-1 | 58 | |
| No DV + 2 × $10^6$ D DCs C pulsed with gp100/TRP2 | 1 | II-1-2 | 62 | |
| No DV + 2 × $10^6$ DCs pulsed with gp100/TRP2 | 1 | II-1-3 | 66 | |
| No DV + 2 × $10^6$ DCs pulsed with gp100/TRP2 | 1 | II-1-4 | 72 | |
| No DV + 2 × $10^6$ DCs pulsed with gp100/TRP2 | 1 | II-1-5 | 60 | 63.6 |

TABLE 7

Murine treatment groups

Group A

| Dengue Virus | # of dendritic cells and type of peptide |
|---|---|
| $10^6$ pfu/ml | $10^6$ DCs pulsed with gp100/pme117 (EGSRNQDWL)(SEQ ID NO: 28) |
| | $10^6$ DCs pulsed with TRP-1/gp75 (TAYRYHLL)(SEQ ID NO: 29) |
| Total | 2 × $10^6$ DCs pulsed with peptide/mouse |

Group B

| Dengue Virus | # of dendritic cells and type of peptide |
|---|---|
| $10^6$ pfu/ml | $10^7$ DCs pulsed with gp100/pme117 (EGSRNQDWL)(SEQ ID NO: 28) |
| | $10^7$ DCs pulsed with TRP-1/gp75 (TAYRYHLL)(SEQ ID NO: 29) |
| Total | 2 × $10^7$ DCs pulsed with peptide/mouse |

Group C- Control

| Dengue Virus | # of dendritic cells and type of peptide |
|---|---|
| None | $10^6$ DCs pulsed with gp100/pme117 (EGSRNQDWL)(SEQ ID NO: 28) |
| | $10^6$ DCs pulsed with TRP-1/gp75 (TAYRYHLL)(SEQ ID NO: 29) |
| Total | 2 × $10^6$ DCs pulsed with peptide/mouse |

Group D - Control

| Dengue Virus | # of dendritic cells and type of peptide |
|---|---|
| $10^6$ pfu/ml | $10^6$ DCs pulsed with OVA (SIINFEKL)(SEQ ID NO: 30) |
| | $10^6$ DCs pulsed with OVA (SIINFEKL)(SEQ ID NO: 30) |
| Total | 2 × $10^6$ DCs pulsed with peptide/mouse |

On day 90, animals were sacrificed and lung tumor colonies were counted. Pulmonary metastases were enumerated in a blinded, coded fashion after insufflation and fixation of the lungs with Fekette's solution. Data were reported as the mean number of metastases; four mice/group (see Table 8). Histopathology of the following major organ systems were performed: brain, heart, lungs, liver, kidneys, spleen and gonads (data not shown).

TABLE 8

Murine histopathology

| Condition | Group | MOUSE ID | NO. OF LUNG METASTASES | Mean |
|---|---|---|---|---|
| DV$10^6$ pfu/ml + 2 × $10^6$ DC pulsed with gp100/TRP2 | A | III-1-1 | 82 | |

TABLE 8-continued

Murine histopathology

| Condition | Group | MOUSE ID | NO. OF LUNG METASTASES | Mean |
|---|---|---|---|---|
| DV$10^6$ pfu/ml + 2 × $10^6$ DC pulsed with gp100/TRP2 | A | III-1-2 | 87 | |
| DV$10^6$ pfu/ml + 2 × $10^6$ DC pulsed with gp100/TRP2 | A | III-1-3 | 78 | |
| DV$10^6$ pfu/ml + 2 × $10^6$ DC pulsed with gp100/TRP2 | A | III-1-4 | 72 | |
| | | | | 79.75 |
| DV$10^7$ pfu/ml + 2 × $10^6$ DC pulsed with gp100/TRP2 | B | III-2-1 | 87 | |
| DV$10^7$ pfu/ml + 2 × $10^6$ DC pulsed with gp100/TRP2 | B | III-2-2 | 77 | |
| DV$10^7$ pfu/ml + 2 × $10^6$ DC pulsed with gp100/TRP2 | B | III-2-3 | 92 | |
| DV$10^7$ pfu/ml + 2 × $10^6$ DC pulsed with gp100/TRP2 | B | III-2-4 | 85 | |
| | | | | 85.25 |
| No dengue virus + 2 × $10^6$ DC pulsed with gp100/TRP2 | C | III-3-1 | 97 | |
| No dengue virus + 2 × $10^6$ DC pulsed with gp100/TRP2 | C | III-3-2 | 94 | |
| No dengue virus + 2 × $10^6$ DC pulsed with gp100/TRP2 | C | III-3-3 | 88 | |
| No dengue virus + 2 × $10^6$ DC pulsed with gp100/TRP2 | C | III-3-4 | 91 | |
| | | | | 92.5 |
| DV$10^6$ pfu/ml + 2 × $10^6$ DC pulsed with OV | D | III-4-1 | 180 | |
| DV$10^6$ pfu/ml + 2 × $10^6$ DC pulsed with OV | D | III-4-2 | 174 | |
| DV$10^6$ pfu/ml + 2 × $10^6$ DC pulsed with OV | D | III-4-3 | 165 | |
| DV$10^6$ pfu/ml + 2 × $10^6$ DC pulsed with OV | D | III-4-4 | 177 | |
| | | | | 174 |

The number of lung metastases observed in mice in Group C (administered tumor antigen primed DCs and no virus) was 47% less than control Group D (administered DENV-2 #1710 and DCs exposed to a control peptide). The number of lung metastases observed in mice in Group A (administered DENV-2 #1710 and tumor antigen primed DCs) was 54% less than control Group D (administered DENV-2 #1710 and DCs exposed to a control peptide). The number of lung metastases observed in mice in Group B (administered DENV-2 #1710 and tumor antigen primed DCs) was 51% less than control Group D (administered DENV-2 #1710 and DCs exposed to a control peptide). The average reduction in Group A and B compared to Group D was 52.8%.

Example 4. Manufacture and Screening of Less Pathogenic Dengue Virus

A Master Cell Bank with validated and certified cell lines from Vero (African Green Monkey Kidney Cells) was generated and tested for absence of any contaminants and adventitious organisms. Vero lines are used by the World Health Organizations to produce a variety of viral vaccines. Dengue virus was passaged in a validated Vero Line derived from the Master Cell Bank and established as a Working Cell Bank according to guidelines established by the FDA Center for Biologics (CBER). Two Dengue Virus Type 2 strains (DNV-2 #1584 and DENV-2 #1710) from initial seed stocks were added to the Vero Cells of the WCB at a MOI of $10^{-5}$.

The first 4-ml overlay medium—containing 1% SeaKem LE agarose (FMC BioProducts, Rockland, Me.) in nutrient medium (0.165% lactalbumin hydrolysate [Difco Laboratories, Detroit, Mich.]), 0.033% yeast extract [Difco], Earle's balanced salt solution, 25 mg of gentamicin sulfate [Bio-Whittaker, Walkersville, Md.] and 1.0 mg of amphotericin B [Fungizone; E. R. Squibb & Sons, Princeton, N.J.], per liter and 2% FBS)—was added after adsorption of the 200-ml virus inoculum for 1.5 h at 37° C. Following incubation at 37° C. for 7 days, a second 2-ml overlay containing additional 80 mg of neutral red vital stain (GIBCO-BRL, Gaithersburg, Md.) per ml was added. Plaques were counted 8 to 11 days after infection.

A plaque assay on final virus cultures was performed. The titer of DNV-2 #1584 was about 5E+06 PFU/ml, and the titer of DENV-2 #1710 was 3.5E+06 pfu/mL as estimated from plaque assays. Dengue virus 2 (DNV-2; #1584) from ATCC showed a clear cytopathic effect in Vero cells 5 days post infection, whereas Vero cells appears to have a morphology change 11 days post infection of the blind passage #2 (#1710 virus). (Data not shown.) The results showed that the DENV-2 #1710 virus is far less cytopathic than the DNV-2 #1584 strain.

Example 5. Cancer Killing Assay with Pulsed DC, with and without DV

In a control arm, normal human tumor infiltrating lymphocytes (TILs) were directly applied to human melanoma FEMX cells. T-cell receptors were matched to FEMX melanoma cell line via HLA A2.1+. In a treatment arm human TILs were exposed to DV supernatants containing interferons and interleukins. Exposed TILs+DV supernatants were placed in culture with FEMX tumor cells. Both arms were left to kill cancer cells for 4 hours at a ratio of 5-to-1 T-cell to tumor cell (100,000 cells to 20,000 cells). Surviving tumor cells were then counted as % of starting cells by flow cytometry. Results, shown in Table 9, demonstrate that DV induces 35% additional cancer cell killing beyond the pulsed DC anti-cancer response.

TABLE 9

DV enhancement of pulsed DC anti-cancer activity

|  | % FL2-A− | % FL2-A+ (% Apoptotic Cells) |
|---|---|---|
| CTL | 86.1% | 13.9% |
| CTL + DV Sups | 81.2% | 18.8% |

Example 6. Human Dendritic Cell Isolation and Pulse with Melanoma Lysate Antigens The following example demonstrates generation of a highly pure CD11a+ mature DC population expressing high levels of human IL-12p70 from pure, isolated CD14+ monocytes, as well as priming of the DC with melanoma cell lysate, the entire process being completed in less than one week. Cells were cultured on hard plastic plates and not exposed to soft plastic bags.

CD14+ monocytes were isolated and analyzed for expression of CD14, CD15, CD45 and 7AAD. Post-prodigy run, 90.25% of input cells were CD14+. CD14+ cells were treated with GM-CSF and IL-4 24 hours post plating to generate immature dendritic cells.

RPMI-7951 melanoma cells from ATCC arrived on the day of the prodigy run and were re-suspended, counted and plated. Melanoma cells were than treated with a calcium hypochlorite solution. Alternatively, cells were treated with sodium chlorite solution. The melanoma cell lysate was added to the immature DC, and maturing agents IFN gamma (1000U/mL), R848 (5 g/mL) and LPS (10 ng/mL) were added.

Supernatant from mature DCs were collected and examined for mycoplasma and endotoxin 22 hours after pulsing with melanoma cell lysate and 18 hours after addition of maturing agents. No pathogenic organisms were observed. An ELISA assay was performed to measure IL-12p70 levels, using supernatant from the DC culture medium. The concentration of IL-12p70 was 19+/−4 ng/mL in a first batch of cells, as opposed to the industry standard of 4-6 ng/mL. Various batches of cells produced by the same protocol showed concentrations of 15-23 ng/mL IL-12p70. A viability assay was conducted and average viability was recorded at 79.2% after cells were frozen, thawed and cultured (compared to a comparator which showed 70%). DC IL-12p70 production relative to that of several comparators was determined. These comparators methods include exposing cells to soft plastic bags, lysing cells with solutions other than a chlorite solution, and do not use the combination of LPS, IFN gamma and R848 to mature cells.

Cells were further frozen and then thawed at 4° C. to test cell counts and viability after freezing and thawing. These were measured at approximately 16 h, 18 h, 20 h and 22 h after beginning of thaw. See Table 10 for results. An extra harvest of non-pulsed DCs were tested in a cryopreservation study, and showed greater than 70% viability. Pre-cryopreservation viability ranged from 85-89%.

TABLE 10

Pulsed DC viability after freeze-thaw

| Time post start thaw | Viability | Total Live Cells in 30 ml |
|---|---|---|
| 16 h | 68.9% | 8.52 × 10^6 |
| 18 h | 67.9% | 8.25 × 10^6 |
| 20 h | 66.3% | 7.23 × 10^6 |
| 22 h | 70.3% | 11.4610^6 |

Switch from these slow thaws (16 h to 22 h, shown in Table 10) to a rapid thaw (37° C. water bath for about 30 sec to about 5 minutes), resulted in viability from 71-79%. Cells not pulsed were used as a cryopreservation study. Viability ranged from 71.4% to 79.2%.

Example 7. Inducing Cytokines in Human White Blood Cells with Dengue Virus

Human white blood cells (WBC), including monocytes, dendritic cells and T lymphocytes, were infected with either mock virus or Dengue virus at three different multiplicities of infection (MOI), MOI of 0.1, MOI of 0.5 and MOI of 2 at time=0. Levels (pg/mL) of various cytokines were measured at 48 h, 72 h and 96 h, post-infection. Treatments were performed in triplicate. Results are shown for each time point in Tables 11-14. (M=mock. 0.1, 0.5 and 2 are MOI). Triplicate average of changes between mock and Dengue virus at the assessed MOIs was calculated and shown as a percentage in Table 11.

TABLE 11

Cytokine levels produced by human WBC, 48 h post- Dengue virus infection

|  | M | M | M | 0.1 | 0.1 | 0.1 |
|---|---|---|---|---|---|---|
| IL-1b | 15 | 6 | 6 | 6 | 6 | 6 |
| IL-10 | 4 | 4 | 4 | 4 | 4 | 4 |
| IL-13 | 11 | 11 | 11 | 11 | 11 | 11 |
| IL-6 | 12 | 7 | 9 | 941 | 874 | 788 |
| IL-12 | 19 | 12 | 13 | 14 | 15 | 15 |
| Rantes | 12 | 11 | 11 | 14 | 16 | 18 |
| CCL-11 | 3 | 3 | 3 | 3 | 3 | 3 |
| IL-17 | 18 | 18 | 18 | 18 | 18 | 18 |
| MIP-1a | 123 | 110 | 109 | 183 | 166 | 219 |
| GM-CSF | 5 | 5 | 5 | 5 | 5 | 5 |
| MIP-1b | 83 | 78 | 82 | 123 | 111 | 118 |
| MCP-1 | 1.77e+03 | 1.48e+03 | 1.87e+03 | 12.6e+03 | 10.4e+03 | 9.95e+03 |
| IL-15 | 33 | 33 | 33 | 33 | 33 | 33 |
| IL-5 | 8 | 8 | 8 | 8 | 8 | 8 |
| IFN-g | 5 | 5 | 5 | 6 | 6 | 6 |
| IFN-a | 16 | 12 | 12 | 37 | 35 | 33 |

TABLE 11-continued

Cytokine levels produced by human WBC, 48 h post- Dengue virus infection

| | | | | | | |
|---|---|---|---|---|---|---|
| IL-1Ra | 3.37e+03 | 2.84e+03 | 3.59e+03 | 4.99e+03 | 4.39e+03 | 4.30e+03 |
| TNF-a | 6 | 6 | 6 | 8 | 8 | 8 |
| IL-2 | 9 | 9 | 9 | 9 | 9 | 9 |
| IL-7 | 16 | 8 | 11 | 31 | 27 | 26 |
| IP-10 | 4 | 4 | 4 | 23 | 15 | 18 |
| IL-2R | 31 | 31 | 31 | 54 | 47 | 52 |
| MIG | 38 | 32 | 39 | 29 | 26 | 26 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |

| | 0.5 | 0.5 | 0.5 | 2 | 2 | 2 |
|---|---|---|---|---|---|---|
| IL-1b | 6 | 6 | 6 | 7 | 7 | 7 |
| IL-10 | 4 | 4 | 5 | 5 | 4 | 4 |
| IL-13 | 11 | 11 | 11 | 11 | 11 | 11 |
| IL-6 | 8.08e+03 | 8.64e+03 | 10.0e+03 | 11.2e+03 | 11.2e+03 | 11.2e+03 |
| IL-12 | 17 | 20 | 19 | 28 | 25 | 25 |
| Rantes | 32 | 56 | 64 | 152 | 135 | 148 |
| CCL-11 | 3 | 3 | 3 | 3 | 3 | 3 |
| IL-17 | 18 | 18 | 18 | 18 | 18 | 18 |
| MIP-1a | 212 | 309 | 328 | 261 | 264 | 259 |
| GM-CSF | 5 | 6 | 7 | 22 | 20 | 21 |
| MIP-1b | 145 | 152 | 142 | 163 | 149 | 155 |
| MCP-1 | 21.8e+03 | 23.4e+03 | 24.2e+03 | 32.0e+03 | 32.0e+03 | 32.0e+03 |
| IL-15 | 33 | 33 | 33 | 68 | 63 | 60 |
| IL-5 | 16 | 18 | 18 | 21 | 21 | 20 |
| IFN-g | 8 | 8 | 8 | 10 | 9 | 10 |
| IFN-a | 47 | 50 | 47 | 67 | 68 | 71 |
| IL-1Ra | 4.55e+03 | 4.88e+03 | 5.14e+03 | 4.13e+03 | 3.42e+03 | 3.82e+03 |
| TNF-a | 16 | 13 | 11 | 21 | 21 | 19 |
| IL-2 | 9 | 9 | 9 | 9 | 9 | 9 |
| IL-7 | 51 | 49 | 47 | 53 | 55 | 54 |
| IP-10 | 39 | 46 | 39 | 218 | 128 | 147 |
| IL-2R | 57 | 69 | 69 | 79 | 76 | 79 |
| MIG | 26 | 31 | 28 | 23 | 22 | 27 |
| IL-4 | 27 | 27 | 27 | 30 | 29 | 30 |
| IL-8 | 17.8e+03 | 17.8e+03 | 17.8e+03 | 17.8e+03 | 17.8e+03 | 17.8e+03 |

TABLE 12

Cytokine levels produced by human WBC, 72 h post- Dengue virus infection

| | M | M | M | 0.1 | 0.1 | 0.1 |
|---|---|---|---|---|---|---|
| IL-1b | 6 | 6 | 6 | 6 | 6 | 6 |
| IL-10 | 4 | 4 | 4 | 4 | 4 | 4 |
| IL-13 | 11 | 11 | 11 | 11 | 11 | 11 |
| IL-6 | 7 | 7 | 7 | 637 | 690 | 737 |
| IL-12 | 12 | 11 | 11 | 12 | 12 | 14 |
| Rantes | 11 | 11 | 11 | 11 | 11 | 11 |
| CCL-11 | 3 | 3 | 3 | 3 | 3 | 3 |
| IL-17 | 18 | 18 | 18 | 18 | 18 | 18 |
| MIP-1a | 96 | 88 | 88 | 84 | 97 | 118 |
| GM-CSF | 5 | 5 | 5 | 5 | 5 | 5 |
| MIP-1b | 83 | 78 | 80 | 85 | 90 | 101 |
| MCP-1 | 5.51e+03 | 5.02e+03 | 4.87e+03 | 21.5e+03 | 22.4e+03 | 21.7e+03 |
| IL-15 | 33 | 33 | 33 | 33 | 33 | 33 |
| IL-5 | 8 | 8 | 8 | 8 | 8 | 8 |
| IFN-g | 5 | 5 | 5 | 6 | 6 | 6 |
| IFN-a | 26 | 23 | 24 | 43 | 46 | 46 |
| IL-1Ra | 6.30e+03 | 5.97e+03 | 6.02e+03 | 6.36e+03 | 6.89e+03 | 6.36e+03 |
| TNF-a | 6 | 6 | 6 | 6 | 6 | 6 |
| IL-2 | 9 | 9 | 9 | 9 | 9 | 9 |
| IL-7 | 8 | 8 | 8 | 23 | 25 | 21 |
| IP-10 | 4 | 4 | 4 | 18 | 14 | 17 |
| IL-2R | 31 | 28 | 20 | 42 | 44 | 42 |
| MIG | 40 | 35 | 35 | 32 | 28 | 27 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |

| | 0.5 | 0.5 | 0.5 | 2 | 2 | 2 |
|---|---|---|---|---|---|---|
| IL-1b | 6 | 6 | 6 | 6 | 7 | 7 |
| IL-10 | 5 | 5 | 4 | 4 | 5 | 5 |
| IL-13 | 11 | 11 | 11 | 11 | 11 | 11 |

TABLE 12-continued

Cytokine levels produced by human WBC, 72 h post- Dengue virus infection

| | | | | | | |
|---|---|---|---|---|---|---|
| IL-6 | 5518 | 8803 | 6841 | 11.2e+03 | 11.2e+03 | 11.2e+03 |
| IL-12 | 15 | 17 | 16 | 17 | 20 | 22 |
| Rantes | 11 | 16 | 15 | 21 | 88 | 68 |
| CCL-11 | 3 | 3 | 3 | 3 | 3 | 3 |
| IL-17 | 18 | 18 | 18 | 18 | 18 | 18 |
| MIP-1a | 91 | 118 | 106 | 54 | 133 | 87 |
| GM-CSF | 5 | 5 | 5 | 8 | 15 | 15 |
| MIP-1b | 104 | 112 | 101 | 84 | 98 | 101 |
| MCP-1 | 32.0e+03 | 32.0e+03 | 32.0e+03 | 32.0e+03 | 32.0e+03 | 32.0e+03 |
| IL-15 | 33 | 33 | 33 | 33 | 38 | 67 |
| IL-5 | 14 | 15 | 14 | 17 | 19 | 20 |
| IFN-g | 8 | 8 | 7 | 6 | 8 | 8 |
| IFN-a | 62 | 56 | 52 | 61 | 66 | 67 |
| IL-1Ra | 6.90e+03 | 6.76e+03 | 6.01e+03 | 4.33e+03 | 3.89e+03 | 4.39e+03 |
| TNF-a | 6 | 6 | 6 | 6 | 6 | 6 |
| IL-2 | 9 | 9 | 9 | 9 | 9 | 9 |
| IL-7 | 42 | 40 | 40 | 45 | 50 | 48 |
| IP-10 | 42 | 38 | 38 | 104 | 143 | 169 |
| IL-2R | 42 | 47 | 47 | 44 | 56 | 60 |
| MIG | 27 | 25 | 22 | 24 | 19 | 25 |
| IL-4 | 27 | 25 | 24 | 26 | 27 | 29 |
| IL-8 | 17.8e+03 | 17.8e+03 | 17.8e+03 | 17.8e+03 | 17.8e+03 | 17.8e+03 |

TABLE 13

Cytokine levels produced by human WBC, 96 h post- Dengue virus infection

| | M | M | M | 0.1 | 0.1 | 0.1 |
|---|---|---|---|---|---|---|
| IL-1b | 6 | 6 | 6 | 6 | 6 | 6 |
| IL-10 | 4 | 4 | 4 | 5 | 4 | 4 |
| IL-13 | 11 | 11 | 11 | 11 | 11 | 11 |
| IL-6 | 9 | 9 | 9 | 834 | 734 | 771 |
| IL-12 | 14 | 13 | 13 | 16 | 14 | 14 |
| Rantes | 11 | 11 | 11 | 11 | 11 | 11 |
| CCL-11 | 3 | 3 | 3 | 3 | 3 | 3 |
| IL-17 | 18 | 18 | 18 | 18 | 18 | 18 |
| MIP-1a | 98 | 89 | 119 | 73 | 103 | 122 |
| GM-CSF | 5 | 5 | 5 | 5 | 5 | 5 |
| MIP-1b | 82 | 78 | 99 | 63 | 89 | 99 |
| MCP-1 | 8.19e+03 | 7.61e+03 | 7.10e+03 | 32.0e+03 | 25.3e+03 | 25.6e+03 |
| IL-15 | 33 | 33 | 33 | 33 | 33 | 33 |
| IL-5 | 8 | 8 | 8 | 8 | 8 | 8 |
| IFN-g | 6 | 6 | 7 | 8 | 7 | 6 |
| IFN-a | 27 | 29 | 27 | 52 | 47 | 44 |
| IL-1Ra | 10.9e+03 | 10.9e+03 | 10.2e+03 | 11.0e+03 | 9.57e+03 | 9.56e+03 |
| TNF-a | 6 | 6 | 6 | 6 | 6 | 6 |
| IL-2 | 9 | 9 | 9 | 9 | 9 | 9 |
| IL-7 | 8 | 8 | 8 | 21 | 18 | 14 |
| IP-10 | 4 | 4 | 4 | 29 | 11 | 11 |
| IL-2R | 25 | 23 | 28 | 39 | 36 | 42 |
| MIG | 39 | 40 | 39 | 39 | 24 | 26 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
| | 0.5 | 0.5 | 0.5 | 2 | 2 | 2 |
| IL-1b | 6 | 6 | 7 | 7 | 6 | 7 |
| IL-10 | 5 | 6 | 6 | 5 | 5 | 5 |
| IL-13 | 11 | 11 | 11 | 11 | 11 | 11 |
| IL-6 | 7026 | 7.47e+03 | 7.65e+03 | 11.2e+03 | 11.2e+03 | 11.2e+03 |
| IL-12 | 16 | 14 | 16 | 16 | 20 | 20 |
| Rantes | 11 | 11 | 11 | 37 | 70 | 68 |
| CCL-11 | 3 | 3 | 3 | 3 | 3 | 3 |
| IL-17 | 18 | 18 | 18 | 18 | 18 | 18 |
| MIP-1a | 79 | 77 | 85 | 60 | 108 | 106 |
| GM-CSF | 5 | 5 | 5 | 12 | 14 | 15 |
| MIP-1b | 85 | 83 | 89 | 67 | 72 | 76 |
| MCP-1 | 32.0e+03 | 32.0e+03 | 32.0e+03 | 32.0e+03 | 32.0e+03 | 32.0e+03 |
| IL-15 | 33 | 33 | 33 | 49 | 43 | 52 |
| IL-5 | 15 | 16 | 16 | 20 | 19 | 18 |
| IFN-g | 7 | 7 | 7 | 7 | 7 | 7 |
| IFN-a | 56 | 58 | 65 | 64 | 64 | 67 |
| IL-1Ra | 7.63e+03 | 7.80e+03 | 8.27e+03 | 5.49e+03 | 4.22e+03 | 4.45e+03 |
| TNF-a | 6 | 6 | 6 | 6 | 6 | 6 |

TABLE 13-continued

Cytokine levels produced by human WBC, 96 h post- Dengue virus infection

| IL-2 | 9 | 9 | 9 | 9 | 9 | 9 |
|---|---|---|---|---|---|---|
| IL-7 | 33 | 37 | 48 | 50 | 45 | 44 |
| IP-10 | 29 | 28 | 33 | 134 | 101 | 104 |
| IL-2R | 39 | 42 | 59 | 52 | 49 | 57 |
| MIG | 19 | 22 | 24 | 20 | 17 | 18 |
| IL-4 | 25 | 24 | 25 | 27 | 27 | 28 |
| IL-8 | 17.8e+03 | 17.8e+03 | 17.8e+03 | 17.8e+03 | 17.8e+03 | 17.8e+03 |

TABLE 14

Relative changes in WBC cytokine levels between mock and Dengue infections

| | MOI 0.1 | | | MOI 0.5 | |
|---|---|---|---|---|---|
| | 48 h | 72 h | 96 h | 48 h | 72 h |
| IL-1b | −33% | 0% | 0% | −33% | 0% |
| IL-10 | 0% | 0% | 8% | 8% | 17% |
| IL-13 | 0% | 0% | 0% | 0% | 0% |
| IL-6 | 9.20E+03% | 9.73E+03% | 8.56E+03% | 95.4E+03% | 10.1E+04% |
| IL-12 | 0% | 12% | 10% | 27% | 41% |
| Rantes | 41% | 0% | 0% | 347% | 27% |
| CCL-11 | 0% | 0% | 0% | 0% | 0% |
| IL-17 | 0% | 0% | 0% | 0% | 0% |
| MIP-1a | 66% | 10% | −3% | 148% | 16% |
| GM-CSF | 0% | 0% | 0% | 20% | 0% |
| MIP-1b | 45% | 15% | −3% | 81% | 32% |
| MCP-1 | 543% | 325% | 262% | 1255% | 523% |
| IL-15 | 0% | 0% | 0% | 0% | 0% |
| IL-5 | 0% | 0% | 0% | 117% | 79% |
| IFN-g | 20% | 20% | 11% | 60% | 53% |
| IFN-a | 163% | 85% | 72% | 260% | 133% |
| IL-1Ra | 39% | 7% | −6% | 49% | 7% |
| TNF-a | 33% | 0% | 0% | 122% | 0% |
| IL-2 | 0% | 0% | 0% | 0% | 0% |
| IL-7 | 140% | 188% | 121% | 320% | 408% |
| IP-10 | 367% | 308% | 325% | 933% | 883% |
| IL-2R | 65% | 62% | 54% | 110% | 72% |
| MIG | −26% | −21% | −25% | −22% | −33% |
| IL-4 | 0% | 0% | 0% | 17% | 10% |
| IL-8 | 0% | 0% | 0% | 0% | 0% |

| | MOI 0.5 | MOI 2 | | |
|---|---|---|---|---|
| | 96 h | 48 h | 72 h | 96 h |
| IL-1b | 6% | −22% | 11% | 11% |
| IL-10 | 42% | 8% | 17% | 25% |
| IL-13 | 0% | 0% | 0% | 0% |
| IL-6 | 8.19E+03% | 12.02E+04% | 16.04E+04% | 12.46E+04% |
| IL-12 | 15% | 77% | 74% | 40% |
| Rantes | 0% | 1179% | 436% | 430% |
| CCL-11 | 0% | 0% | 0% | 0% |
| IL-17 | 0% | 0% | 0% | 0% |
| MIP-1a | −21% | 129% | 1% | −10% |
| GM-CSF | 0% | 320% | 153% | 173% |
| MIP-1b | −1% | 92% | 17% | −17% |
| MCP-1 | 319% | 1774% | 523% | 319% |
| IL-15 | 0% | 93% | 39% | 45% |
| IL-5 | 96% | 158% | 133% | 138% |
| IFN-g | 11% | 93% | 47% | 11% |
| IFN-a | 116% | 415% | 166% | 135% |
| IL-1Ra | −26% | 16% | −31% | −56% |
| TNF-a | 0% | 239% | 0% | 0% |
| IL-2 | 0% | 0% | 0% | 0% |
| IL-7 | 392% | 363% | 496% | 479% |
| IP-10 | 650% | 4008% | 3367% | 2725% |
| IL-2R | 84% | 152% | 103% | 108% |
| MIG | −45% | −34% | −38% | −53% |
| IL-4 | 7% | 29% | 19% | 19% |
| IL-8 | 0% | 0% | 0% | 0% |

Example 8. Additional Virus Manufacturing Protocols

In addition to methods of Example 4, both Vero and FRhL cells are infected using dilutions of the supernatant from blind passage #2, DENV-2 #1710 and DNV-2 #1584, respectively. In order to increase the detection sensitivity, an immunofluorescence staining is developed to detect virus in the cells infected with supernatant from blind passage #2.

Ultracentrifugation is used to concentrate virus when necessary. Following confirmation of virus titer, final product is filtered to remove any cellular debris, assessed for absence of any adventitious organisms, and upon final lot released, bottled in 5 ml bottles, and stored at 4° C. until ready for shipment and administration.

Example 8: Dengue Virus Supernatant Increases ICAM-1 Expression on Tumor Cells

To determine if Dengue virus supernatant increases ICAM-1 expression on tumor cells flow cytometric analysis was carried out on a 96 well plate containing 30 μl of Dengue virus supernatant. The 30 uLs of Dengue virus supernatant was from human PBMCs infected at $10^6$ plaque forming units per mL. These supernatants were exposed to A549 cells for 6 hours, afterwhich mouse monoclonal G-class antibody ($I_gG$) to ICAM-1 was applied at 100,000 A549 cells per well. Dengue virus supernatant of human PBMC was collected at 72 hrs at a Multiplicity of infection (MOI) of 2 (MOI:2), and 72 hrs. mock (no virus) after 6 hrs. of incubation. All MOI:2 and mock well conditions utilized A549 cells. All conditions were performed in duplicate. The changes in ICAM-1 expression were measured by flow cytometry using $I_gG$ to ICAM-1 to label human lung adenocarcinoma A549 cells, Table 15.

TABLE 15

| Well conditions | |
|---|---|
| Well | Condition |
| B1.2.fcs, B2.2.fcs | A549 cell line alone |
| B3.2.fcs, B4.2.fcs | A549 with dengue virus MOCK supernatants (no dengue proteins, but with a mock control protein) |
| B5.2.fcs, B6.2.fcs | A549 with dengue virus supernatant proteins at multiplicity of infection of 2 |

Dengue-induced TNFα resulted in an ICAM-1 increase in lung cancer (A549) cell lines of either doubling or tripling. The aim of this experiment was to test MHC I expression on A549 lung cancer, an immunoresistant and difficult-to-kill tumor cell line, in the absence and presence of dengue virus supernatant. This was completed via in-vitro assays over 72 hours.

All results were measured graphically via flow cytometry as defined by geometric mean. Shown in FIG. 3A and FIG. 3B, the geometric mean of the dengue virus supernatant well-condition (B05 B5.2.fcs and B06 B6.2.fcs in Set1 and Set 2 respectively) showed an approximate doubling or tripling of ICAM-1 up-regulation compared to the control A549 cells without supernatant. Dengue infected PBMC increased the "stickiness" factor involved in CTL-to-tumor interaction, from B01 to B05. The geometric mean of 1857 increase to 3670 in the fluorescent measure of ICAM-1, Table 16.

TABLE 16

| Flow cytometric count of CD54 expression in Set 1 and Set 2 of FIG. 3A and FIG. 3B | | | |
|---|---|---|---|
| Sample | Sample Type | Count | Geometric Mean: Comp-FL4-A |
| 1 | Tumor-Set1 | 4507 | 1857 |
| 2 | Tumor-Set 1 | 3552 | 1174 |
| 3 | Tumor-Set 1 | 3632 | 3670 |
| 1 | Tumor-Set 2 | 3770 | 1320 |
| 2 | Tumor-Set 2 | 3634 | 1039 |
| 3 | Tumor-Set 2 | 3490 | 3929 |

Example 9: Dengue Virus Supernatant Increases Human Leukocyte Antigen (HLA) Expression on Melanoma Tumor Cells To determine if Dengue virus supernatant increases MHC expression on the melanoma tumor cell lines FEMX (a mixture of HLA-A2.1$^+$ cells) and 624.28 (cell line missing HLA A2.1 at the gene level) tumor cell lines were incubated with 30 uL of Dengue virus supernatant from human PBMCs infected at $10^6$ plaque forming units per mL as in Table 17. HLA-A, HLA-B, and HLA-C expression was measured by flow cytometry using the W6/A32 pan-HLA antibody, which reacts to all HLA gene products.

TABLE 17

| Well conditions | |
|---|---|
| Well | Condition |
| B01.E1.fcs | 624.28 cell line alone |
| B01.E3.fcs | 624.28 with dengue virus supernatant proteins at multiplicity of infection of 2 |

A 1.6-fold increase in the MFI (Mean Fluorescence Intensity or geometric mean) was detected of MHC class I, (HLA-A, B, C.) from 72383 up to 117343 in fluorescence when detecting MHC-I on the 624.28 tumor cell line, FIG. 4A and Table 18. This effect is indicative of the up-regulation of HLA-A2. All conditions were performed in duplicates. When 624.28 cells are exposed to Dengue supernatant, MHC expressions was upregulated. Similarly, when Dengue virus supernatant was incubated with a high HLA-expression tumor cell line, FEMX, the HLA expression was increased by 1.32 over control, FIG. 4B.

TABLE 18

| HLA surface expression 624.28 | | | |
|---|---|---|---|
| Sample | Subset | Count | Geometric Mean: Comp-FL2-H |
| 1 | ME (E1 vs E3) | 13134 | 117343 |
| 2 | ME (E1 vs E3) | 13726 | 72383 |
| 3 | ME (E1 vs E5) | 18088 | 76916 |
| 4 | ME (E1 vs E5) | 13726 | 72383 |

Dengue virus supernatant was incubated with melanoma tumor cell lines FEMX (a mixture of HLA-A2.1$^+$ cells) and 624.28 (cell line missing HLA A2.1 at the gene level) tumor cell lines. Cell lines were incubated with 30 uL of Dengue virus supernatant from human PBMCs infected at $10^6$ plaque forming units per mL as in Table 19.

TABLE 19

Plate Template and FACs counts

|   | 1 | 2 | 3 | 4 | 5 | 6 |
|---|---|---|---|---|---|---|
| A |   |   |   |   |   |   |
| B |   |   |   |   |   |   |
| C |   |   |   |   |   |   |
| D | FEMX Count: 10688 Mean: 115824 | FEMX Count: 10448 Mean: 96794 | FEMX + 30 µL DV supernatant MOI: 2 Count: 10070 Mean: 122967 | FEMX + 30 µL DV supernatant MOI: 2 Count: 14808 Mean: 107219 | FEMX + 30 µL DV supernatant Mock Count: 14074 Mean: 82106 | FEMX + 30 µL DV supernatant Mock Count: 14487 Mean: 89359 |
| E | 624.28 Count: 13726 Mean: 72383 | 624.28 Count: 14390 Mean: 74874 | 624.28 + 30 µL DV supernatant MOI: 2 Count: 13134 Mean: 117343 | 624.28 + 30 µL DV supernatant MOI: 2 Count: 12809 Mean: 118423 | 624.28 + 30 µL DV supernatant Mock Count: 18088 Mean: 76916 | 624.28 + 30 µL DV supernatant Mock Count: 19881 Mean: 64761 |

HLA-A, HLA-B, and HLA-C expression was measured by flow cytometry using the W6/A32 pan-HLA antibody, which reacts to all HLA gene products, FIGS. 5A-5L.

Example 10: Cytokine-Induced Dengue Virus Impact for Checkpoint Inhibitors

In order to determine which cytokines were induced by Dengue virus, peripheral blood monocytes (PBMC; human white blood cells) were infected with Dengue virus. Leukopaks derived from apheresis were utilized to isolate PBMC. The PBMC, containing monocytes, DCs, NK, T and B cells, were placed in complete cell media at 37° C. and 5% FBS. Dengue virus was expanded to $10^6$ pfu/ml in Vero (African Green Monkey) kidney cells. The virus titer was calculated to $3.5 \times 10^6$ PFU/mL in Vero cells using standard growth conditions. PBMC was infected at escalating doses of multiplicities of infection (MOI). The following MOI were used: Mock (PBMC with no virus), 0.1 (a ratio of 1 virus particle to 10 PBMC cells), 0.5 (a ratio of 5 virus particles to 10 PBMC cells), and 2.0 (a ratio of 20 virus particles to 10 PBMC cells). The supernatants were collected and frozen at −80° C. Resulting supernatants were used to measure the cytokines using a multiplex ELISA panel and compared against supernatant collected before infection. Comparison of mock infections to the changes across MOI 0.1, 0.5, and 2.0 confirmed a virus-concentration and time-dependence of activation. Original measures were done in triplicates, in pg/mL, expressed as a % of baseline pre- and post-infection by dengue virus as shown in Table 20. Some values may exceed instrument measurements; such data points were set to the measurement maximums as a means of calculating % increases.

Results show that Dengue virus infection of PBMCs results in up-regulation of Class I MHC to allow the CTL to recognize their targets (IFNγ, IFNα), increase in CTL proliferation and cytotoxic capability (IL-2), preventing apoptosis of activated CTL (IL-7, IL-15). A point to be made is that PBMC is not completely representative of in vivo conditions. The lack of soluble or somatic receptors can influence cytokine levels. For example, contact activation, even without Dengue virus, induced levels of IL-8 above detection limits. IL-6 was also very high, and IL-2 was reduced/absent as the lack of concentrated dendritic cells (DCs) in the PBMC allowed the virus-mediated IL-2 block to remain. In vivo, the clustering of infected, activated DCs in lymphatics can overcome the virus IL-2 block, supporting the CTL proliferation.

A brief summary of some of the cytokines and their anti-tumor benefits follows: IFN-α—pro-inflammatory cytokine that promotes Class I MHC expression, starting both the innate and adaptive immune response. Data shows an increase of 415% above baseline. IFN-γ—produced typically by activated NK and CTL, IFN-γ up-regulates Class I MHC and activates macrophages to Type 1 polarity. Data shows an increase of 93% above baseline. IP-10—a macrophage-supportive chemokine, IP-10 is an independent predictor of clinical response in renal cell carcinoma. Data shows an increase of 4008% above baseline. IL-6—one of the early cytokines expected of dengue infection; while its increase acts as both an inflammatory and anti-inflammatory cytokine. It has inflammatory properties when applied to immune cells, but all somatic cells carry the low-affinity receptor, gp130. Binding to gp130 activates anti-inflammatory genes to protect from immune-mediated damage. Data shows an increase of >120000%, but this experiment was not under homeostatic control. In dengue cases with IL-6 receptor activity, levels are much lower, between 3.1-80.1 pg/mL, and are not definitively correlated with disease severity. These levels are well below the 10,000-fold IL-6 rise seen in cytokine release syndrome such as with CAR-T therapy. IL-12—as it functions as "signal 3", to license CTL to become effector-capable. DCs pulsed with self-peptide in the absence of IL-12 induce $T^{Reg}$ $CD4^+$ $CD25^+$ cells, lower the immune response. Data shows an increase of 77% above baseline. IL-8—a pro-inflammatory cytokine that restores critical adhesion points along tumor epithelial cells which lead to further tumor microenvironment infiltration by CTL; Data shows a constant heighted stimulation, far beyond data measures. IL-8 is important to help open gap junctions in tumor blood vessels. The levels of IL-8 in dengue patients are moderate and increases are not associated with higher toxicity. IL-15—an adaptive cytokine of the IL-2 family, IL-15 increases cytolytic function of CTL and NK cells and slows CTL apoptosis. Data shows an increase of 93% above baseline. IL-7—an adaptive cytokine of the IL-2 family, IL-7 stimulates CTL and NK cells to effector status, making them better at killing their targets. It also induces a switch from glycolysis to fatty acid metabolism, allowing transition of CTL to central memory and memory/effector T cells data shows an increase of 363% above baseline. IL-2—the prototypical TH1 cytokine; IL-2 induces CTL proliferation; data shows an increase of 152% in the IL-2 receptor, but IL-2 was not detected. A review with dengue experts confirmed that the likely cause was a viral-contact-mediated block of IL-2 production on T cells. In human infections, infected, activated DCs with high expression of co-stimulatory markers CD80/83/86, are clustered in lymph nodes. This clustering effect overcomes the temporary block, allowing high CTL proliferation mediated by increased IL-2. This effect would be challenging to duplicate in vitro, as it requires enrichment of DCs and CTL, then construction of a 3-D tissue scaffolding system.

phils). This is accomplished with immuno-magnetic selection or, alternatively, by adherence properties. Immuno-magnetic selection involves pouring the white blood cells into a sterile plastic column with plastic beads coated with antibodies for immune cell CD surface proteins: (CD4/CD8/CD56, etc.).

TABLE 20

Cytokine Detection by ELISA. Mean of triplicate values, some values may exceed instrument measurements; such data points were set to the measurement maximums.

| | TNF-a | IFN-a | IFN-g | IL-6 | IL-12 | IL-8 | IP-10 | RANTES | MIP-1a | MIP-1b | MCP-1 | IL-1b | IL-1RA |
|---|---|---|---|---|---|---|---|---|---|---|---|---|---|
| 48 hr | 11.92 | 41.25 | 7.17 | 5253.58 | 18.50 | 17781.00 | 57.08 | 55.75 | 211.92 | 125.08 | 16964.75 | 7.00 | 4118.83 |
| MOCK | 6.00 | 13.33 | 5.00 | 9.33 | 14.67 | 17781.00 | 4.00 | 11.33 | 114.00 | 81.00 | 1708.67 | 9.00 | 3268.33 |
| MOI 0.1 | 8.00 | 35.00 | 6.00 | 867.67 | 14.67 | 17781.00 | 18.67 | 16.00 | 189.33 | 117.33 | 10990.33 | 6.00 | 4559.00 |
| MOI 0.5 | 13.33 | 48.00 | 8.00 | 8911.33 | 18.67 | 17781.00 | 41.33 | 50.67 | 283.00 | 146.33 | 23148.00 | 6.00 | 4859.00 |
| MOI 2.0 | 20.33 | 68.67 | 9.67 | 11226.00 | 26.00 | 17781.00 | 164.33 | 145.00 | 261.33 | 155.67 | 32012.00 | 7.00 | 3789.00 |
| 72 hr | 6.00 | 47.67 | 6.50 | 4743.75 | 14.92 | 17781.00 | 49.58 | 23.75 | 96.67 | 93.08 | 22751.08 | 6.17 | 5844.42 |
| MOCK | 6.00 | 24.33 | 5.00 | 7.00 | 11.33 | 17781.00 | 4.00 | 11.00 | 90.67 | 80.33 | 5136.00 | 6.00 | 6096.00 |
| MOI 0.1 | 6.00 | 45.00 | 6.00 | 688.00 | 12.67 | 17781.00 | 16.33 | 11.00 | 99.67 | 92.00 | 21844.33 | 6.00 | 6536.67 |
| MOI 0.5 | 6.00 | 56.67 | 7.67 | 7054.00 | 16.00 | 17781.00 | 39.33 | 14.00 | 105.00 | 105.67 | 32012.00 | 6.00 | 6545.00 |
| MOI 2.0 | 6.00 | 64.67 | 7.33 | 11226.00 | 19.67 | 17781.00 | 138.67 | 59.00 | 91.33 | 94.33 | 32012.00 | 6.67 | 4200.00 |
| 96 hr | 6.00 | 50.00 | 6.83 | 4849.08 | 15.50 | 17781.00 | 41.00 | 22.83 | 93.25 | 81.83 | 24818.33 | 6.25 | 8346.08 |
| MOCK | 6.00 | 27.67 | 6.33 | 9.00 | 13.33 | 17781.00 | 4.00 | 11.00 | 102.00 | 86.33 | 7632.67 | 6.00 | 10719.67 |
| MOI 0.1 | 6.00 | 47.67 | 7.00 | 779.67 | 14.67 | 17781.00 | 17.00 | 11.00 | 99.33 | 83.67 | 27616.67 | 6.00 | 10047.00 |
| MOI 0.5 | 6.00 | 59.67 | 7.00 | 7381.67 | 15.33 | 17781.00 | 30.00 | 11.00 | 80.33 | 85.67 | 32012.00 | 6.33 | 7899.00 |
| MOI 2.0 | 6.00 | 65.00 | 7.00 | 11226.00 | 18.67 | 17781.00 | 113.00 | 58.33 | 91.33 | 71.67 | 32012.00 | 6.67 | 4718.67 |
| Average Change | 80% | 204% | 47% | 132839% | 64% | 0% | 3367% | 687% | 45% | 30% | 563% | −3% | −37% |

| | Eotaxin | MIG | IL-15 | IL-7 | IL-2 | IL-2R | IL-13 | IL-17 | IL-4 | IL-5 | IL-10 | GM-CSF |
|---|---|---|---|---|---|---|---|---|---|---|---|---|
| 48 hr | 3.00 | 28.92 | 40.67 | 35.67 | 9.00 | 56.25 | 11.00 | 18.00 | 25.67 | 13.50 | 4.17 | 9.25 |
| MOCK | 3.00 | 36.33 | 33.00 | 11.67 | 9.00 | 31.00 | 11.00 | 18.00 | 23.00 | 8.00 | 4.00 | 5.00 |
| MOI 0.1 | 3.00 | 27.00 | 33.00 | 28.00 | 9.00 | 51.00 | 11.00 | 18.00 | 23.00 | 8.00 | 4.00 | 5.00 |
| MOI 0.5 | 3.00 | 28.33 | 33.00 | 49.00 | 9.00 | 65.00 | 11.00 | 18.00 | 27.00 | 17.33 | 4.33 | 6.00 |
| MOI 2.0 | 3.00 | 24.00 | 63.67 | 54.00 | 9.00 | 78.00 | 11.00 | 18.00 | 29.67 | 20.67 | 4.33 | 21.00 |
| 72 hr | 3.00 | 28.25 | 36.25 | 29.83 | 9.00 | 41.92 | 11.00 | 18.00 | 24.67 | 12.25 | 4.33 | 6.92 |
| MOCK | 3.00 | 36.67 | 33.00 | 8.00 | 9.00 | 26.33 | 11.00 | 18.00 | 23.00 | 8.00 | 4.00 | 5.00 |
| MOI 0.1 | 3.00 | 29.00 | 33.00 | 23.00 | 9.00 | 42.67 | 11.00 | 18.00 | 23.00 | 8.00 | 4.00 | 5.00 |
| MOI 0.5 | 3.00 | 24.67 | 33.00 | 40.67 | 9.00 | 45.33 | 11.00 | 18.00 | 25.33 | 14.33 | 4.67 | 5.00 |
| MOI 2.0 | 3.00 | 22.67 | 46.00 | 47.67 | 9.00 | 53.33 | 11.00 | 18.00 | 27.33 | 18.67 | 4.67 | 12.67 |
| 96 hr | 3.00 | 27.25 | 36.75 | 27.83 | 9.00 | 40.92 | 11.00 | 18.00 | 24.50 | 12.67 | 4.75 | 7.17 |
| MOCK | 3.00 | 39.33 | 33.00 | 8.00 | 9.00 | 25.33 | 11.00 | 18.00 | 23.00 | 8.00 | 4.00 | 5.00 |
| MOI 0.1 | 3.00 | 29.67 | 33.00 | 17.67 | 9.00 | 39.00 | 11.00 | 18.00 | 23.00 | 8.00 | 4.33 | 5.00 |
| MOI 0.5 | 3.00 | 21.67 | 33.00 | 39.33 | 9.00 | 46.67 | 11.00 | 18.00 | 24.67 | 15.67 | 5.67 | 5.00 |
| MOI 2.0 | 3.00 | 18.33 | 48.00 | 46.33 | 9.00 | 52.67 | 11.00 | 18.00 | 27.33 | 19.00 | 5.00 | 13.67 |
| Average Change | 0% | −42% | 59% | 435% | 0% | 123% | 0% | 0% | 22% | 143% | 17% | 216% |

Example 11. Collection of PBMC from Donors

Donors (either autologous or HLA-matched allogenic) have a leukapheresis procedure performed at a facility with trained personnel and proper equipment. After the apheresis is complete, the red cells, platelets, and plasma proteins are returned to the donor. The apheresis product is assessed at the site (Gram Stain test and Limulus Amoeba Lysis [LAL]) for presence of bacterial contamination. After passing, the collection container (with small testing sample container attached), is barcoded with donor-specific information and placed in an approved shipping container conforming to both FDA and DOT regulations for storage and shipping of non-infectious biological materials. The shipping container is packaged with a cooling element (e.g., solid $CO_2$, Liquid $N_2$), and temperature monitors. The shipping container is a hard plastic flask. A courier transports the container within 24 hours to the GMP manufacturing facility.

Example 12. Manufacture and Use of Dendritic Cells Pulsed with Tumor Antigens

Monocytes are separated from other collected white blood cells (e.g. T cells. B cells, NK cells, eosinophils and baso- An example of immunomagnetic selection is the EasySep Monocyte Enrichment kit available from Stem Cell Technologies (Vancouver, B.C, Canada, www.stemcell.com). To use the EasySep kit, the apheresis product is suspended in sterile PBS and poured into the EasySep plastic column containing Tetrameric antibody complexes with murine antibodies for: human CD2, CD3, CD16, CD19, CD20, CD56, CD66b, CD123, and Glycophorin A. After incubation for 10 minutes, EasySep magnetic particles are added. The cells adhering to the beads removed an electromagnet sorting. The magnet is inverted, and the desired cell fraction (monocytes), is poured into a sterile polystyrene flask for additional processing. Alternately, in a positive adherence selection assay, magnetic beads coated with CD1+/CD14+ antibodies is mixed with monocytes, a magnet is placed against the column, and non-binding cells are flushed out of the column with PBS solution. The monocytes are then washed off the beads. In positive adherence selection, the properties of monocytes to stick to certain surfaces are used to separate them by running the apheresis product down a slanted column.

Alternatively, bone marrow cells are depleted for lymphocytes and MHC Class positive cells by Fluorescent Activated Cell Sorting (FACS) with monoclonal antibodies for CD3, CD4, and CD8. Remaining cells are cultured overnight at 37° C. in a 5% $CO_2$ atmosphere in a basal cell culture medium supplemented with human AB serum. Human AB serum is chosen because it grows cells at a faster rate than other serum types, and serum free media produces DCs with much lower T-cell stimulation capability. After 24 hours, the cells are replated and cultured in the presence of Granulocyte-Macrophage Colony Stimulation Factor (GM-CSF), and recombinant IL-4 at 900 U/ml. After 3 to 4 days, media to be exchanged for fresh cytokine media.

Alternatively, dermal dendritic cells (DDCs) are prepared using the following methods: Keratomes from healthy human volunteers are incubated in a solution of the bacterial proteases Dispase type 2 at a final concentration of 1.2 U/ml in RPMI 1640 for 1 hour at 37° C. After the incubation period, epidermis and dermis are easily separated. Epidermal and dermal sheets are then cut into small (1-10 mm) pieces after several washing with PBS, and placed in RPMI 1640 supplemented with 10% Fetal Bovine Serum (FBS), and placed in 10-cm tissue culture plates. After 2-3 days, pieces of tissue are removed, and the medium collected. Cells migrating out of the tissue sections into the medium are spun down, resuspended in 1-2 ml fresh medium and stained with trypan blue. Further enrichment is achieved by separation on a metrizamide gradient. Cells are layered onto 3-ml columns of hypertonic 14.5% metrizamide and sedimented at 650 g for 10 minutes at room temperature. Low density interphase cells are collected and washed in two successively less hypertonic washes (RPMI 1640 with 10% FBS and 40 mM NaCl) to return cells to isotonicity.

When the monocytes are collected, they may number only a few thousand. The recombinant human growth factors rhuInterleukin-4 (IL-4), and rhuGranulocyte-Macrophage-Colony-Stimulation Factor (GM-CSF), are used in a multi-step protocol to accomplish the expansion of DC numbers to the range of 50 million. After the addition of IL-4 and GM-CSF, cells are assessed for and expansion in number and the development of mature-DC markers: ($CD11^+$, $CD80^+$, $CD83^+$), as well as increased expression of both Class I (for presentation of short peptides to $CD8^+$, and Class II MHC complexes (for presentation of longer peptides to $CD4^+$Helper-Inducer T lymphocytes). After approximately 3-4 days, the number of mature DCs will be measured. For example, the monocyte-enriched fraction is placed in Nuclon-coated Cell Factory (Thermoscientific), with serum-free DC media (CellGro, Inc.), supplemented with GMP-2% human AB serum, 500 IU/ml (about 50 ng/ml) rhuIL-4 (CellGenix), with 500 IU/ml (about 50 ng/ml) rhuGM-CSF (CellGenix), added after the first 24 hours. Final product is approximately about 1L of total media volume. After about 72 hours of culture, a population of immature DCs are assessed for the following markers: $CD1^+$ $CD11^+$ $CD14^+$.

Example 13. Pulsing the Dendritic Cells

A variety of tumor antigen sources are used for high-quality DCs: peptides, lysate from autologous tumors, whole tumor cells, and RNA coding for specific tumor antigens. An excisional biopsy or blood sample containing leukemic or lymphoma cells are obtained by surgery or blood draw followed by a magnetic selection to obtain leukemia/lymphoma cells. Once the tumor cells are obtained, they are barcoded and shipped in approved containers similar to those described for apheresis previously to the GMP facility. Samples may be frozen at −70° C. after passing bacterial contamination tests.

Whole autologous tumor cell lysate is prepared by several methods. To prepare the lysate, the tumor sample may be rewarmed to approximately 35° C. using a water bath or other procedure. The development of automated cell processors like the Miltenyi GentleMACS system allows the sample to be manually minced, suspended in PBS solution, then a pre-selected tissue-specific software-controlled rotor system separates the tumor cells. Cells are added to an enzyme mixture before being transferred to the Miltenyi GentleMACS dissociator. The single-cell suspension can be membrane-lysed with minimal damage to tumor peptides, using a hypochlorite solution, which will kill any residual tumor cells, neutralize $dT_H2$ cytokines, and increase immunogenicity for superior CTL affinity, avidity and activation. After adding hypochlorite, culture plates are incubated at 37 degrees Celsius, 5% $CO_2$, for 1 hour, with gentle manual agitation at 30 min to disperse hypochlorite. Cells are washed two time to neutralize the lysis reaction (e.g. with HBSS). Hypochlorite-treated cells may be subjected to subsequent freeze-thaw cycles. Alternatively, the sample does not separate the tumor cells. Instead the sample is left to contain tumor cells and supporting cells (e.g. cells from the tumor microenvironment). Cells are lysed with calcium hypochlorite to eliminate red blood cells and produce apoptotic and necrotic bodies without destroying peptides needed for CTL induction.

Lysate from the GentleMACS is added on the third day of immature DCs production. Immature DCs are co-cultured with tumor lysate for about 16 hours. The final step is maturation with an inflammatory signal. Clinical-Grade LPS (60 EU/ml) (R & D Invivogen), and Interferon-gamma (2000 IU/ml, about 100 ng/ml) (R&D Systems) are added to the flask and incubated for about 12 hours to mature the pulsed DC. After exposure to LPS, the DCs are assessed for up-regulation of $CD80/CD83^+$ activation markers, and increase production of IL-12p70. In process testing at this stage includes sterility (as previously described), viability (% viable cells by Trypan Blue dye exclusion), and specificity (% DC measured by CD11c flow cytometry).

After final sterility, specificity, and viability assessment, the DCs are transferred to hard plastic containers suitable for freezing at −70° C. in liquid $N_2$, storage up to 1 year, and shipping to the clinic for use. The containers are shipped cool overnight, then re-warmed to 37° C. in a warm-water bath before intravenous administration with a 0.9% NaCl solution concurrent over 30 minutes. The DCs are administered intravenously.

Example 14. Combination Delivery for Treatment of Cancer

Administration of the Dengue Virus is similar to that of other viral vaccine injections. A subject has an area of skin in the shoulder (deltoid) region cleaned with alcohol, then 0.5 ml of the virus is injected under the skin to mimic a mosquito bite. Once the subject has a fever the reaches 38.5° C., after 2-5 days from DV injection, the subject is infused by intravenous line concurrent with 0.9% NaCl solution with pulsed (primed) dendritic cells. Infusions are repeated until the subject is negative for disease. DC infusions will use cells as manufactured in Example 6.

Example 15: Co-Administration of an Immune Checkpoint Inhibitor with Dengue Virus for the Treatment of Cancer in a Mouse Model One or more immune checkpoint inhibitory agents are administered to mice in a mouse model for cancer. On day 0, mice receive 5×10⁴ of cultured tumor cells intravenously into the lateral tail vein. On day 7, the mice are inoculated with 0.05 mL of Dengue virus at 1×10⁶ or 1×10⁷ pfu/mL by injection in the base of the tail. Recombinant murine IL-2 (Genzyme) and IFN-gamma (Sigma Pharmaceuticals) are administered by intravenous infusion at 2,000 1U (rIL-2) and 500 1U (rIFN-gamma) at 5-day intervals following administration of Dengue virus and an effective amount of at least one of Pembrolizumab, Ipilimumab (e.g., BMS-734016, MDX-010), Enoblituzumab (e.g., MGA271), Lirilumab (e.g., BMS-986015, IPH2102), BMS986016, Atezolizumab (e.g., MPDL3280A, RG7446, RO5541267), or Bavituximab. Exemplary amino acid sequences for immune checkpoint modulatory agents are provided in Table 21. On days 21, 35 and 49, the mouse DC are incubated with peptides and injected intravenously. Two groups of control mice are used. One group of mice receives no Dengue virus and no dendritic cells. A group of control mice receives Dengue virus and dendritic cells but no immune checkpoint inhibitor. Histopathology and biochemical analyses of organs including brain, heart, liver, kidneys, spleen, and gonads are performed.

Mice that are treated with either Pembrolizumab, Ipilimumab (e.g., BMS-734016, MDX-010), Enoblituzumab (e.g., MGA271), Lirilumab (e.g., BMS-986015, IPH2102), BMS986016, Atezolizumab (e.g., MPDL3280A, RG7446, RO5541267), Bavituximab, or combinations thereof, are compared to mice that are not treated with an immune checkpoint inhibitor. Tumor size, migration, biochemical markers for cancer, and increased long term survival are recorded.

TABLE 21

Immunoglobulin heavy and light chain amino acid sequence

| Target | SEQ. ID | Drug | Amino Acid Sequence |
|---|---|---|---|
| PD-1 | 10 | Pembrolizumab (MK-3475, SCH 900475) | Heavy Chain Sequence QVQLVQSGVEVKKPGASVKVSCKASGYTFTNYYMYW VRQAPGQGLEWMGGINPSNGGTNFNEKFKNRVTLTTD SSTTTAYMELKSLQFDDTAVYYCARRDYRFDMGFDYW GQGTTVTVSSASTKGPSVFPLAPCSRSTSESTAALGCLV KDYFPEPVTVSWNSGALTSGVHTFPAVLQSSGLYSLSSV VTVPSSSLGTKTYTCNVDHKPSNTKVDKRVESKYGPPC PPCPAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLTCLVKGFYPSDIAVE WESNGQPENNYKTTPPVLDSDGSFFLYSRLTVDKSRWQ QGNVFSCSVMHEALHNHYTQKSLSLS |
| PD-1 | 11 | Pembrolizumab (MK-3475, SCH 900475) | Light Chain Sequence EIVLTQSPATLSLSPGERATLSCRASKGVSTSGYSYLHW YQQKPGQAPRLLIYLASYLESGVPARFSGSGSGTDFTLTI SSLEPEDFAVYYCQHSRDLPLTFGGGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC |
| | 12 | Nivolumab (BMS-936558, MDX-1106, ONO-4538) | Heavy Chain Sequence QVQLVESGGGVVQPGRSLRLDCKASGITFSNSGMHWV RQAPGKGLEWVAVIWYDGSKRYYADSVKGRFTISRDN SKNTLFLQMNSLRAEDTAVYYCATNDDYWGQGTLVTV SSASTKGPSVFPLAPCSRSTSESTAALGCLVKDYFPEPVT VSWNSGALTSGVHTFPAVLQSSGLYSLSSVVTVPSSSLG TKTYTCNVDHKPSNTKVDKRVESKYGPPCPPCPAPEFL GGPSVFLFPPKPKDTLMISRTPEVTCVVVDVSQEDPEVQ FNWYVDGVEVHNAKTKPREEQFNSTYRVVSVLTVLHQ DWLNGKEYKCKVSNKGLPSSIEKTISKAKGQPREPQVY TLPPSQEEMTKNQVSLTCLVKGFYPSDIAVEWESNGQPE NNYKTTPPVLDSDGSFFLYSRLTVDKSRWQEGNVFSCS VMHEALHNHYTQKSLSLSLGK |
| | 13 | Nivolumab (BMS-936558, MDX-1106, ONO-4538) | Light Chain Sequence EIVLTQSPATLSLSPGERATLSCRASQSVSSYLAWYQQK PGQAPRLLIYDASNRATGIPARFSGSGSGTDFTLTISSLEP EDFAVYYCQQSSNWPRTFGQGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC |
| PDL-1 | 14 | Atezolizumab (MPDL3280A, RG7446, RO5541267) | Heavy Chain Sequence EVQLVESGGGLVQPGGSLRLSCAASGFTFSDSWIHWVR QAPGKGLEWVAWISPYGGSTYYADSVKGRFTISADTSK NTAYLQMNSLRAEDTAVYYCARRHWPGGFDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKKVEPKSCDKTHTCPP CPAPELLGGPSVFLFPPKPKDTLMISRTPEVTCVVVDVS HEDPEVKFNWYVDGVEVHNAKTKPREEQYAST YRVVSVLTVLHQDWLNGKEYKCKVSNKALPAPIEKTIS |

TABLE 21-continued

Immunoglobulin heavy and light chain amino acid sequence

| Target | SEQ. ID | Drug | Amino Acid Sequence |
|---|---|---|---|
| | | | KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPGK |
| PDL-1 | 15 | Atezolizumab (MPDL3280A, RG7446, RO5541267) | Light Chain Sequence DIQMTQSPSSLSASVGDRVTITCRASQDVSTAVAWYQQKPGKAPKL LIYSASFLYSGVPSRFSGSGSGTDFTLTISSLQPEDFATYYCQQYLYH PATFGQGTKVEIKRTVAAPSVFIFPPSDEQLKSGTASVVCLLNNFYP REAKVQWKVDNALQSGNSQESVTEQDSKDSTYSLSSTLTLSKADY EKHKVYACEVTHQGLSSPVTKSFNRGEC |
| CTLA-4 | 16 | Ipilimumab (BMS-734016, MDX-010) | Heavy Chain Sequence QVQLVESGGGVVQPGRSLRLSCAASGFTFSSYTMHWV RQAPGKGLEWVTFISYDGNNKYYADSVKGRFTISRDNS KNTLYLQMNSLRAEDTAIYYCARTGWLGPFDYWGQGT LVTVSSASTKGPSVFPLAPSSKSTSGGTAALGCLVKDYF PEPVTVSWNSGALTSGVHTFPAVLQSSGLYSLSSVVTVP SSSLGTQTYICNVNHKPSNTKVDKRVEPKSCDKTHTCPP CPAPELLGGPSVFLFPPKPKDTLMISRTPEVTCVVVDVS HEDPEVKFNWYVDGVEVHNAKTKPREEQYNSTYRVVS VLTVLHQDWLNGKEYKCKVSNKALPAPIEKTISKAKGQ PREPQVYTLPPSRDELTKNQVSLTCLVKGFYPSDIAVEW ESNGQPENNYKTTPPVLDSDGSFFLYSKLTVDKSRWQQ GNVFSCSVMHEALHNHYTQKSLSLSPGK |
| CTLA-4 | 17 | Ipilimumab (BMS-734016, MDX-010) | Light Chain Sequence EIVLTQSPGTLSLSPGERATLSCRASQSVGSSYLAWYQQ KPGQAPRLLIYGAFSRATGIPDRFSGSGSGTDFTLTISRLE PEDFAVYYCQQYGSSPWTFGQGTKVEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| | 18 | Tremelimumab (CP-675, CP-675, 206) | Heavy Chain Sequence QVQLVESGGGVVQPGRSLRLSCAASGFTFSSYGMHWV RQAPGKGLEWVAVIWYDGSNKYYADSVKGRFTISRDN SKNTLYLQMNSLRAEDTAVYYCARDPRGATLYYYYG MDVWGQGTTVTVSSASTKGPSVFPLAPCSRSTSESTAA LGCLVKDYFPEPVTVSWNSGALTSGVHTFPAVLQSSGL YSLSSVVTVPSSNFGTQTYTCNVDHKPSNTKVDKTVER KCCVECPPCPAPPVAGPSVFLFPPKPKDTLMISRTPEVTC VVVDVSHEDPEVQFNWYVDGVEVHNAKTKPREEQFNS TFRVVSVLTVVHQDWLNGKEYKCKVSNKGLPAPIEKTI SKTKGQPREPQVYTLPPSREEMTKNQVSLTCLVKGFYPS DIAVEWESNGQPENNYKTTPPMLDSDGSFFLYSKLTVD KSRWQQGNVFSCSVMHEALHNHYTQKSLSLSPGK |
| | 19 | Tremelimumab (CP-675, CP-675, 206) | Light Chain Sequence DIQMTQSPSSLSASVGDRVTITCRASQSINSYLDWYQQK PGKAPKLLIYAASSLQSGVPSRFSGSGSGTDFTLTISSLQP EDFATYYCQQYYSTPFTFGPGTKVEIKRTVAAPSVFIFPP SDEQLKSGTASVVCLLNNFYPREAKVQWKVDNALQSG NSQESVTEQDSKDSTYSLSSTLTLSKADYEKHKVYACE VTHQGLSSPVTKSFNRGEC |
| PS | 20 | Bavituximab | Heavy Chain Sequence EVQLQQSGPELEKPGASVKLSCKASGYSFTGYNMNWV KQSHGKSLEWIGHIDPYYGDTSYNQKFRGKATLTVDKS SSTAYMQLKSLTSEDSAVYYCVKGGYYGHWYFDVWG AGTTVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKKVEPKSCDKTH TCPPCPAPELLGGPSVFLFPPKPKDTLMISRTPEVTCVVV DVSHEDPEVKFNWYVDGVEVHNAKTKPREEQYNSTYR VVSVLTVLHQDWLNGKEYKCKVSNKALPAPIEKTISKA KGQPREPQVYTLPPSRDELTKNQVSLTCLVKGFYPSDIA VEWESNGQPENNYKTTPPVLDSDGSFFLYSKLTVDKSR WQQGNVFSCSVMHEALHNHYTQKSLSLSPGK |
| PS | 21 | Bavituximab | Light Chain Sequence DIQMTQSPSSLSASLGERVSLTCRASQDIGSSLNWLQQGPDGTIKRLI YATSSLDSGVPKRFSGSRSGDYSLTISSLESEDFVDYYCLQYVSSPP TFGAGTKLELKRADAAPSVFIFPPSDEQLKSGTASVVCLLNNFYPRE AKVQWKVDNALQSGNSQESVTEQDSKDSTYSLSSTLTLSKADYEK HKVYACEVTHQGLSSPVTKSFNRGEC |

TABLE 21-continued

Immunoglobulin heavy and light chain amino acid sequence

| Target | SEQ. ID | Drug | Amino Acid Sequence |
|---|---|---|---|
| KIR | 22 | Lirilumab (BMS-986015, IPH2102) | Heavy Chain Sequence<br>QVQLVQSGAEVKKPGSSVKVSCKASGGTFSFYAISWVR<br>QAPGQGLEWMGGFIPIFGAANYAQKFQGRVTITADEST<br>STAYMELSSLRSDDTAVYYCARIPSGSYYYDYDMDVW<br>GQGTTVTVSSASTKGPSVFPLAPCSRSTSESTAALGCLV<br>KDYFPEPVTVSWNSGALTSGVHTFPAVLQSSGLYSLSSV<br>VTVPSSSLGTKTYTCNVDHKPSNTKVDKRVESKYGPPC<br>PPCPAPEFLGGPSVFLFPPKPKDTLMISRTPEVTCVVVDV<br>SQEDPEVQFNWYVDGVEVHNAKTKPREEQFNSTYRVV<br>SVLTVLHQDWLNGKEYKCKVSNKGLPSSIEKTISKAKG<br>QPREPQVYTLPPSQEEMTKNQVSLTCLVKGFYPSDIAVE<br>WESNGQPENNYKTTPPVLDSDGSFFLYSRLTVDKSRWQ<br>EGNVFSCSVMHEALHNHYTQKSLSLSLGK |
| KIR | 23 | Lirilumab (BMS-986015, IPH2102) | Light Chain Sequence<br>EIVLTQSPVTLSLSPGERATLSCRASQSVSSYLAWYQQK<br>PGQAPRLLIYDASNRATGIPARFSGSGSGTDFTLTISSLEP<br>EDFAVYYCQQRSNWMYTFGQGTKLEIKRTVAAPSVFIF<br>PPSDEQLKSGTASVVCLLNNFYPREAKVQWKVDNALQ<br>SGNSQESVTEQDSKDSTYSLSSTLTLSKADYEKHKVYA<br>CEVTHQGLSSPVTKSFNRGEC |
| CD137 | 24 | Urelumab (BMS-663513) | Heavy Chain Sequence<br>QVQLQQWGAGLLKPSETLSLTCAVYGGSFSGYYWSWI<br>RQSPEKGLEWIGEINHGGYVTYNPSLESRVTISVDTSKN<br>QFSLKLSSVTAADTAVYYCARDYGPGNYDWYFDLWG<br>RGTLVTVSSASTKGPSVFPLAPCSRSTSESTAALGCLVK<br>DYFPEPVTVSWNSGALTSGVHTFPAVLQSSGLYSLSSVV<br>TVPSSSLGTKTYTCNVDHKPSNTKVDKRVESKYGPPCPP<br>CPAPEFLGGPSVFLFPPKPKDTLMISRTPEVTCVVVDVS<br>QEDPEVQFNWYVDGVEVHNAKTKPREEQFNSTYRVVS<br>VLTVLHQDWLNGKEYKCKVSNKGLPSSIEKTISKAKGQ<br>PREPQVYTLPPSQEEMTKNQVSLTCLVKGFYPSDIAVE<br>WESNGQPENNYKTTPPVLDSDGSFFLYSRLTVDKSRWQ<br>EGNVFSCSVMHEALHNHYTQKSLSLSLGK |
| CD137 | 25 | Urelumab (BMS-663513) | Light Chain Sequence<br>EIVLTQSPATLSLSPGERATLSCRASQSVSSYLAWYQQK<br>PGQAPRLLIYDASNRATGIPARFSGSGSGTDFTLTISSLEP<br>EDFAVYYCQQRSNWPPALTFCGGTKVEIKRTVAAPSVFI<br>FPPSDEQLKSGTASVVCLLNNFYPREAKVQWKVDNAL<br>QSGNSQESVTEQDSKDSTYSLSSTLTLSKADYEKHKVY<br>ACEVTHQGLSSPVTKSFNRGEC |
| CD27 | 26 | Varlilumab CDX-1127) | Heavy Chain Sequence<br>QVQLVESGGGVVQPGRSLRLSCAASGFTFSSYDMHWV<br>RQAPGKGLEWVAVIWYDGSNKYYADSVKGRFTISRDN<br>SKNTLYLQMNSLRAEDTAVYYCARGSGNWGFFDYWG<br>QGTLVTVSSASTKGPSVFPLAPSSKSTSGGTAALGCLVK<br>DYFPEPVTVSWNSGALTSGVHTFPAVLQSSGLYSLSSVV<br>TVPSSSLGTQTYICNVNHKPSNTKVDKKVEPKSCDKTH<br>TCPPCPAPELLGGPSVFLFPPKPKDTLMISRTPEVTCVVV<br>DVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSRDELTKNQVSLTCLVKGFYPSDIA<br>VEWESNGQPENNYKTTPPVLDSDGSFFLYSKLTVDKSR<br>WQ |
| CD27 | 27 | Varlilumab CDX-1127) | Light Chain Sequence<br>DIQMTQSPSSLSASVGDRVTITCRASQGISRWLAWYQQ<br>KPEKAPKSLIYAASSLQSGVPSRFSGSGSGTDFTLTISSLQ<br>PEDFATYYCQQYNTYPRTFGQGTKVEIKRTVAAPSVFIF<br>PPSDEQLKSGTASVVCLLNNFYPREAKVQWKVDNALQ<br>SGNSQESVTEQDSKDSTYSLSSTLTLSKADYEKHKVYA<br>CEVTHQGLSSPVTKSFNRGEC |

Example 16: Co-Administration of an Immune Modulatory Agent that Activates an Immune Checkpoint with Dengue Virus for the Treatment of Cancer in a Mouse Model One or more immune checkpoint activating agents are administered to mice in a mouse model for cancer. On day 0, mice receive $5 \times 10^4$ of cultured tumor cells intravenously into the lateral tail vein. On day 7, the mice are inoculated with 0.05 mL of Dengue virus at $1 \times 10^6$ or $1 \times 10^7$ pfu/mL by injection in the base of the tail. Recombinant murine IL-2 (Genzyme) and IFN-gamma (Sigma Pharmaceuticals) are administered by intravenous infusion at 2,000 1U (rIL-2) and 500 1U (rIFN-gamma) at 5-day intervals following administration of Dengue virus and an effective amount of at least one of Urelumab (e.g., BMS-663513), Varlilumab (e.g., CDX-1127), or TRX518. Exemplary amino acid sequences for immune checkpoint modulatory agents are seen in Table 15. On days 21, 35 and 49, the mouse DCs are incubated with peptides and injected intravenously. Two groups of control mice are used. One group of mice receives no Dengue virus and no dendritic cells. Another group of control mice receive Dengue virus and dendritic cells but no immune checkpoint modulatory agent. Histopathology and biochemical analyses of organs including brain, heart, liver, kidneys, spleen, and gonads are performed. In one example assay, the immune checkpoint activating agent is Urelumab (e.g., BMS-663513), Varlilumab (e.g., CDX-1127), TRX518, or combinations thereof.

Example 17: Dengue Virus and DCs Paired with Other Dendritic Cells

A patient with cancer is treated with autologous dendritic cells that are pulsed with a tumor cell lysate containing antigens expressed on the patient's cancer cells. In some cases, the cancer is metastatic melanoma. The autologous dendritic cells are cultured and stored in soft plastic bags according to standard industry protocols. A subsequent CAT-SCAN or measure of cancer markers in the bloodstream of the patient reveals that the dendritic cells have had little to no effect on tumor size or cancer growth. The autologous dendritic cells are administered again, along with Dengue virus and dendritic cells that have been cultured and stored on a hard surface and pulsed with the same tumor lysate.

Example 18: Dengue Virus and DCs Paired with Oncolytic Viruses

A patient with cancer is treated with an oncolytic virus (a virus that targets and lyses cancer cells), along with Dengue virus and primed dendritic cells. The dendritic cells are cultured and stored on a hard surface and pulsed with a tumor lysate containing antigens expressed on the cancer cells of the patient.

Example 19: Dengue Virus and DCs Paired with CTLA4/PD-1/PD-L1 Therapy

A patient with metastatic melanoma is treated with a checkpoint inhibitor. The checkpoint inhibitor is Ipilimumab, a monoclonal antibody inhibitor of cytotoxic T-lymphocyte-associated antigen 4 (CTLA-4). Alternatively, the checkpoint inhibitor is Nivolumab, a monoclonal antibody inhibitor of programmed death 1 (PD-1). The patient also receives Dengue virus and primed dendritic cells. The dendritic cells are cultured and stored on a hard surface and pulsed with a tumor lysate containing antigens expressed on the cancer cells of the patient. Dengue virus and dendritic cells paired with the checkpoint inhibitor stimulates the immune system of the patient. Treatment is continued with the checkpoint inhibitor to achieve a complete response or near complete response.

Example 20: Dengue Virus and DCs Paired with CAR-T Cells

A patient with cancer is treated with chimeric antigen receptor T cells (CAR-T cells) programmed to target antigens on the cancer cells of the patient, along with Dengue virus and primed dendritic cells. The dendritic cells are cultured and stored on a hard surface and pulsed with a tumor lysate containing antigens expressed on the cancer cells of the patient. Dengue virus and dendritic cells paired with the checkpoint inhibitor stimulates the immune system of the patient.

Example 21: Dengue Virus and DCs Paired with IL-2 Therapy

A patient with cancer is treated with high-dose interleukin-2 (IL-2, Proleukin), along with Dengue virus and primed dendritic cells. The dendritic cells are cultured and stored on a hard surface and pulsed with a tumor lysate containing antigens expressed on the cancer cells of the patient. Dengue virus and dendritic cells paired with IL-2 stimulates the immune system of the patient.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treatment of cancer, comprising administering a Dengue virus to a subject having received an immune checkpoint modulatory agent, wherein the immune checkpoint modulatory agent is an antibody against PD1.

2. The method of claim 1, wherein the Dengue virus is present in an amount of about $10^2$ to about $10^8$ plaque-forming units (PFU)/mL.

3. The method of claim 1, wherein the Dengue virus is in a volume of about 0.01 mL to about 0.1 mL.

4. The method of claim 1, wherein the Dengue virus is 45AZ5.

5. The method of claim 1, wherein the Dengue virus is DENV-2 strain #1710.

6. The method of claim 1, wherein the cancer is a carcinoma.

7. The method of claim 1, wherein the cancer is lung cancer.

8. The method of claim 1, wherein the cancer is selected from the group consisting of: small cell lung cancer, non-small cell lung cancer (NSCLC), mesothelioma, squamous cell carcinoma, adenocarcinoma, and large cell carcinoma.

9. The method of claim 1, wherein the cancer is metastatic.

* * * * *